US009347937B2

(12) United States Patent
Larche et al.

(10) Patent No.: US 9,347,937 B2
(45) Date of Patent: May 24, 2016

(54) VACCINE COMPRISING AMB A 1 PEPTIDES FOR USE IN THE TREATMENT OF RAGWEED ALLERGY

(71) Applicant: Circassia Limited, Oxford (GB)

(72) Inventors: Mark Larche, Ontario (CA); Roderick Peter Hafner, Oxford (GB); Paul Laidler, Oxford (GB)

(73) Assignee: Circassia Limited, Oxford (GB)

( * ) Notice: Subject to any disclaimer, the term of this patent is extended or adjusted under 35 U.S.C. 154(b) by 0 days.

(21) Appl. No.: 13/917,756

(22) Filed: Jun. 14, 2013

(65) Prior Publication Data

US 2013/0295123 A1 Nov. 7, 2013

Related U.S. Application Data

(62) Division of application No. 13/057,386, filed as application No. PCT/GB2009/001986 on Aug. 14, 2009, now Pat. No. 8,491,910.

(30) Foreign Application Priority Data

| Aug. 15, 2008 | (GB) | .................................... 0814986.6 |
| Aug. 15, 2008 | (WO) | ................ PCT/GB2008/002779 |
| Aug. 15, 2008 | (WO) | ................ PCT/GB2008/002781 |
| Aug. 20, 2008 | (GB) | .................................... 0815218.3 |
| May 1, 2009 | (EP) | .................................... 09251252 |

(51) Int. Cl.

| *A61K 38/00* | (2006.01) |
| *A61K 38/04* | (2006.01) |
| *A61K 39/00* | (2006.01) |
| *A61K 39/35* | (2006.01) |
| *A61K 39/36* | (2006.01) |
| *A61K 39/38* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *G01N 33/50* | (2006.01) |
| *C07K 7/06* | (2006.01) |
| *C07K 7/08* | (2006.01) |
| *C07K 14/415* | (2006.01) |
| *G01N 33/569* | (2006.01) |

(52) U.S. Cl.
CPC ............ *G01N 33/5094* (2013.01); *A61K 38/04* (2013.01); *A61K 39/36* (2013.01); *C07K 7/06* (2013.01); *C07K 7/08* (2013.01); *C07K 14/415* (2013.01); *G01N 33/505* (2013.01); *G01N 33/56972* (2013.01); *G01N 2800/24* (2013.01)

(58) Field of Classification Search
None
See application file for complete search history.

(56) References Cited

U.S. PATENT DOCUMENTS

| 5,736,507 | A | 4/1998 | Boots et al. |
| 5,820,862 | A | 10/1998 | Garman et al. |
| 6,335,019 | B1 | 1/2002 | Rogers et al. |
| 8,491,910 | B2 * | 7/2013 | Larche et al. ............... 424/184.1 |
| 2002/0146759 | A1 | 10/2002 | Albani et al. |
| 2004/0265342 | A1 | 12/2004 | Larche et al. |
| 2006/0024334 | A1 | 2/2006 | Larche et al. |
| 2007/0092532 | A1 | 4/2007 | Root-Bernstein |

FOREIGN PATENT DOCUMENTS

| EP | 1958645 A1 | 8/2008 |
| JP | 7-507924 | 9/1995 |
| WO | 90/11293 A1 | 10/1990 |
| WO | 93/21321 A2 | 10/1993 |
| WO | 94/01560 A1 | 1/1994 |
| WO | 96/13589 A1 | 5/1996 |
| WO | 99/34826 A1 | 7/1999 |
| WO | 03/088997 A2 | 10/2003 |
| WO | 03/094957 A2 | 11/2003 |
| WO | 2004/092210 A2 | 10/2004 |
| WO | 2006/075253 A2 | 7/2006 |
| WO | 2006/132607 A1 | 12/2006 |
| WO | 2007/063075 A | 6/2007 |
| WO | 2008/098749 A2 | 8/2008 |
| WO | 2008/139163 A1 | 11/2008 |
| WO | 2008/145998 A1 | 12/2008 |
| WO | 2009/022154 A2 | 2/2009 |
| WO | 2009/022156 A2 | 2/2009 |
| WO | 20209/022157 A2 | 2/2009 |

OTHER PUBLICATIONS

U.S. Appl. No. 13/057,386, filed May 27, 2011, Mark Larche.
U.S. Appl. No. 13/057,386, May 20, 2013.
U.S. Appl. No. 13/057,386, Dec. 18, 2012.
U.S. Appl. No. 13/057,386, Sep. 12, 2012.
Akdis, Cezmi A. et al., "Role of Interleukin 10 in Specific Immunotherapy," J. Clin. Invest., vol. 102(1):98-106 (1998).
Alexander, Clare et al., "Peptide-based Vaccines in the Treatment of Specific Allergy," Current Drug Targets—Inflammation & Allergy, vol. 1(4):353-361 (2002).

(Continued)

*Primary Examiner* — Nora Rooney
(74) *Attorney, Agent, or Firm* — Nelson Mullins Riley & Scarborough LLP; Jane E. Remillard, Esq.; Jeanne M. DiGiorgio, Esq.

(57) ABSTRACT

The present invention relates to compositions for preventing or treating allergy to ragweed by tolerization. The compositions are based on combinations of peptide fragments derived from the major allergen in ragweed pollen, Amb a 1. The invention also relates to products, vectors and formulations which may be used to provide polypeptides of the invention in combination. The invention further relates to in vitro methods for determining whether T cells recognize a polypeptide of the invention, and for determining whether an individual has or is at risk of a condition characterized by allergic symptoms in response to a ragweed allergen.

11 Claims, 3 Drawing Sheets

(56) References Cited

OTHER PUBLICATIONS

Blumenthal, Malcolm H. et al., "Definition of an Allergen (Immunobiology)," Allergens and Allergen Immunotherapy, Third Edition, Richard F. Lockey (Ed.), Marcek Dekker, Inc., New York, pp. 37-50 (2004).
Campbell, John D. et al., "Peptide immunotherapy in allergic asthma generates IL-10-dependent immunological tolerance associated with linked epitope suppression," J. Exp. Med., vol. 206(7):1535-1547 (2009).
Cardinale, Elizabeth J. et al., "Matrix-assisted Laser Desorption/Ionization Time-of-flight (MALDI-TDF) Mass Spectrometry in the Analysis of Allergen Vaccines," J. Allergy Clin. Immunol., vol. 107(2):S19, Abstract No. 65 (2002).
Creticos, P.S. et al., "Efficacy of Allervax Ragweed peptides in the Treatment of Ragweed-Induced Allergy," J. Allergy Clin. Immunol., vol. 99(1, Part 2), Abstract 1631 (1997).
Greene, Wayne K. et al., "IgE and IgG Binding of Peptides Expressed from Fragments of cDNA Encoding the Major House Dust Mite Allergen DER P I1," The Journal of Immunology, vol. 147(11):3768-3773 (1991).
Griffith, I.J. et al., "Sequence Polymorphism of Amb A I and Amb a II, the Major Allergens in *Ambrosia artemisiifolia* (Short Ragweed)," Int. Arch. Allergy Appl. Immunol., vol. 96:296-304 (1991).
Hall, Gillian et al., "Suppression of allergen reactive Th2 mediated responses and pulmonary eosinophilia by intranasal administration of an immunodominant peptide is linked to IL-10 production," Vaccine, vol. 21:549-561 (2003).
ICH Harmonised Tripartite Guideline, "General Considerations for Clinical Trials E8," 17 pages, (1997).
ICH Harmonised Tripartite Guideline, "Guideline for Good Clinical Pratice E6(R1)," 60 pages, (1996).
Joost Van Neerven, R. J. et al., "T Cell Epitopes of House Dust Mite Major Allergen Der P II1," The Journal of Immunology, vol. 151(4):2326-2335 (1993).
Kearley, Jennifer et al., "Resolution of airway inflammation and hyperreactivity after in vivo transfer of CD4+CD25+ regulatory T cells is interleukin 10 dependent," J. Med. Chem., vol. 202(11):1539-1547 (2005).
King, Te Piao et al., "Chemical Modifications of the Major Allergen of Ragweed Pollen, Antigen E," Immunochemistry, vol. 11:83-92 (1974).
Larche, Mark et al., "Peptide-based therapeutic vaccines for allergic and autoimmune diseases," Nature Medicine Supplement, vol. 11(4):S69-S76 (2005).
Larche, M., "Peptide immunotherapy for allergic diseases," Allergy, vol. 62:325-331 (2007).
Lichtenstein, L.M. et al., "Initial Clinical Experience with T Cell Epitope Defined Peptides from Ragweed Allergen," J. Allergy Clin. Immunol., Abstract 999 (1995).
Litwin, A. et al., "Regulation of the human immune response to ragweed pollen by immunotherapy. A controlled trial comparing the effect of immunosuppressive peptic fragments of short ragweed with standard treatment," Chemical and Experimental Allergy, vol. 21:457-465 (1991).
Michael, J.G. et al., "Modulation of the immune response to ragweed allergens by peptic fragments," Clinical and Experimental Allergy, vol. 20:669-674 (1990).
Muller, W. -D. et al., "Mapping of T-cell epitopes of Phl p 5: evidence for crossreacting and non-crossreacting T-cell epitopes within Phl p 5 isoallergens," Clinical and Experimental Allergy, vol. 28:1538-1548 (1998).

Ngo, J. Thomas et al., "Computational Complexity Protein Structure Prediction, and the Levinthal Paradox," The Protein Folding Properties and Tertiary Structure Prediction, K. Merz (Ed.), Birkhauser, Bosoton, Chapter 2, pp. 491-495 (1994).
Nicodemus, Christopher et al., "Integrated Clinical Experience with Tolerogenic Peptides," International Archive of Allergy and Immunology, vol. 113:326-328 (1997).
Nielsen, Morten et al., "Quantitative Predictions of Peptide Binding to Any HLA-DR Molecule of Known Sequence: NetMHCIIpan," PLoS Computational Biology, vol. 4(7):e1000107, 10 pages (2008).
Oldfield, William L.G. et al., "Allergen-Derived T Cell Peptide-Induced Late Asthmatic Reactions Precede the Induction of Antigen-Specific Hyporesponsiveness in Atopic Allergic Asthmatic Subjects," The Journal of Immunology, vol. 167:1734-1739 (2001).
Rafnar, Thorunn et al., "Cloning of Amb a I (Antigen E), the Major Allergen Family of Short Ragweed Pollen," The Journal of Biological Chemistry, vol. 266(2):1229-1236 (1991).
Schenk, Siegfried et al., "T-cell epitopes of Phl p 1, major pollen allergen of timothy grass (*Phleum pratense*): Evidence for crossreacting and non-crossreacting T-cell epitopes within grass group I allergens," J. Allergy Clin. Immunol., vol. 96(6, Part 1):986-996 (1995).
Skolnick, Jeffrey et al., "From genes to protein structure and function: novel applications of computational approaches in the genomic era," Trends in Biotech., vol. 18:34-39 (2000).
Sone, T. et al., "Identification of human T cell epitopes in Japanese cypress pollen allergen, Cha o 1, elucidates the intrinsic mechanism of cross-allergenicity between Cha o 1 and Cry j 1, the major allergen of Japanese cedar pollen, at the T cell level," Clin. Exp. Allergy, vol. 35:664-671 (2005).
Tarzi, M. M et al., "Induction of interleukin-10 and suppressor of cytokine signalling-3 gene expression following peptide immunotherapy," Clin. Exp. Allergy, vol. 36(4):465-474 (2006).
Verhoef, Adrienne et al., "T Cell Epitope Immunotherapy Induces a CD4+ T Cell Population with Regulatory Activity," PLOS Medicine, vol. 2(3):e78 (2005).
World Medical Association Declaration of Helsinki, "Ethical Principles for Medical Research Involving Human Subjects," 5 pages, (2008).
Wraith, David C., "Peptide-based therapy for autoimmune diseases," Drug Discovery Today: Therapeutic Strategies, vol. 3(1):35-40 (2006).
International Search Report and Written Opinion for Application No. PCT/GB2009/001986, dated Jun. 4, 2010.
Papers filed in EPO in opposition to European Patent No. 2153841 by Strawman Limited, 39 pages, (2012).
Bysice, Andrew, "Possible Intrinsic adjuvanticity of the Amb a 1 (*Ambrosia artemisiifolia*: Ragweed) allergen," Open Access Dissertations and Theses, McMaster University, 102 pages (2012).
U.S. Appl. No. 10/489,972, filed Sep. 15, 2004, Robyn O'Hehir.
U.S. Appl. No. 12/871,575, filed Aug. 30, 2010, Robyn O'Hehir.
U.S. Appl. No. 10/489,972, Apr. 30, 2010.
U.S. Appl. No. 10/489,972, Jul. 21, 2009.
U.S. Appl. No. 10/489,972, Nov. 28, 2008.
U.S. Appl. No. 10/489,972, Nov. 1, 0007.
U.S. Appl. No. 10/489,972, Apr. 2, 2007.
U.S. Appl. No. 12/871,575, May 8, 2013.
U.S. Appl. No. 12/871,575, Mar. 29, 2012.
U.S. Appl. No. 12/871,575, Oct. 26, 2011.
U.S. Appl. No. 12/871,575, Aug. 26, 2011.

\* cited by examiner

VACCINE COMPRISING AMB A 1 PEPTIDES FOR USE IN THE TREATMENT OF RAGWEED ALLERGY

RELATED APPLICATIONS

This application is a divisional of U.S. patent application Ser. No. 13/057,386 filed May 27, 2011, which is a 35 U.S.C. 371 national stage filing of International Application No. PCT/GB2009/001986 filed Aug. 14, 2009, which claims priority to GB Application No. 0814986.6 filed Aug. 15, 2008; PCT application No. PCT/GB08/002781 filed Aug. 15, 2008; PCT application No. PCT/GB08/002779 filed Aug. 15, 2008; GB Application No. 0815218.3 filed Aug. 20, 2008 and EP Application No. 09251252.4 filed May 1, 2009. The contents of the aforementioned applications are hereby incorporated by reference.

INCORPORATING BY REFERENCE

The contents of the following priority applications are incorporated herein by reference: United Kingdom Patent Application No. 0814986.6 filed 15 Aug. 2008; International Patent Application No.'s PCT/GB08/002781 and PCT/GB08/002779, both filed 15 Aug. 2008; United Kingdom Patent Application No. 0815218.3 filed 20 Aug. 2008 and European Patent Application No. 09251252.4 filed 1 May 2009.

FIELD OF THE INVENTION

The present invention relates to compositions for preventing or treating allergy to ragweed.

BACKGROUND OF THE INVENTION

T-cell antigen recognition requires antigen presenting cells (APCs) to present antigen fragments (peptides) on their cell surface in association with molecules of the major histocompatibility complex (MHC). T cells use their antigen specific T-cell receptors (TCRs) to recognise the antigen fragments presented by the APC. Such recognition acts as a trigger to the immune system to generate a range of responses to eradicate the antigen which has been recognised.

Recognition of external antigens by the immune system of an organism, such as man, can in some cases result in diseases, known as atopic conditions. Examples of the latter are the allergic diseases including asthma, atopic dermatitis and allergic rhinitis. In this group of diseases, B lymphocytes generate antibodies of the IgE class (in humans) which bind externally derived antigens, which are referred to in this context as allergens since these molecules elicit an allergic response. Production of allergen-specific IgE is dependent upon T lymphocytes which are also activated by (are specific for) the allergen. Allergen-specific IgE antibodies bind to the surface of cells such as basophils and mast cells by virtue of the expression by these cells of surface receptors for IgE.

Crosslinking of surface bound IgE molecules by allergen results in degranulation of these effector cells causing release of inflammatory mediators such as histamine, 5-hydroxtryptamine and lipid mediators such as the sulphidoleukotrienes. In addition to IgE-dependent events, certain allergic diseases such as asthma are characterised by IgE-independent events.

Allergic IgE-mediated diseases are currently treated with agents which provide symptomatic relief or prevention. Examples of such agents are anti-histamines, β2 agonists, and glucocorticosteroids. In addition, some IgE-mediated diseases are treated by desensitisation procedures that involve the periodic injection of allergen components or extracts. Desensitisation treatments may induce an IgG response that competes with IgE for allergen, or they may induce specific suppressor T cells that block the synthesis of IgE directed against allergen. This form of treatment is not always effective and poses the risk of provoking serious side effects, particularly general anaphylactic shock. This can be fatal unless recognised immediately and treated with adrenaline. A therapeutic treatment that would decrease or eliminate the unwanted allergic-immune response to a particular allergen, without altering the immune reactivity to other foreign antigens or triggering an allergic response itself would be of great benefit to allergic individuals.

Ragweed allergens are universally recognised as a major cause of allergic diseases in humans and animals, including asthma, allergic rhinitis and allergic dermatitis. Proteins present in ragweed pollen are particularly important. For example, approximately 75% of hayfever sufferers in the United States are allergic to ragweed pollen. Hayfever is the common term for a form of seasonal allergy characterised by sneezing, runny nose and itching eyes. The term "hayfever" arose because this form of allergic disease is most prevalent during "haying season", which corresponds to the flowering season of many plants, that is when they release the highest quantities of pollen. It is particularly prevalent from late summer to early Autumn, typically from the end of June to the end of September (in the Northern Hemisphere).

It has been calculated that for adults in the United States, hayfever is the 5th leading chronic disease and a major cause of work absenteeism, resulting in nearly 4 million missed or lost workdays each year, resulting in a total cost of more than $700 million in total lost productivity. Allergies are also the most frequently reported chronic condition in children, limiting activities for more than 40% of them. Each year, allergies account for more than 17 million outpatient office visits in the United States; seasonal allergies such as hayfever account for more than half of these allergy visits.

A therapeutic or preventative treatment would therefore be of great benefit to humans that suffer or are at risk of suffering from ragweed allergy.

SUMMARY OF THE INVENTION

Ragweed allergy is typically caused by Common ragweed (*Ambrosia artemisiifolia*). The major allergen in ragweed pollen is Amb a 1. This protein exists as a number of different isoforms, Amb a 1.1, 1.2, 1.3 and 1.4. The present inventors have discovered that certain combinations of peptide fragments derived from the Amb a 1 proteins are particularly useful in desensitising individuals to these allergens. The polypeptide combinations of the invention have been selected for their ability bind to many MHC Class II molecules, be highly soluble, to not trigger histamine release from basophils drawn from a panel of ragweed allergic individuals and to induce a cytokine response in a high proportion of subjects from a panel of ragweed allergic individuals. The compositions, products, vectors and formulations of the invention may therefore be provided to individuals for preventing or treating allergy to ragweed by tolerisation.

The peptides of the invention were selected as potential T cell epitopes through in silico methods. When regions containing epitopes were identified, they were further analysed to determine which of them were highly conserved between the four different Amb a 1 isoforms. These candidate polypeptides were then further screened for potential use in tolerisation. More specifically, they were analysed for solubility characteristics, and the ability to induce cytokine release from PBMC derived from ragweed allergic individuals. In some instances, the peptide sequences were engineered to improve solubility and/or reduce dimer formation.

A difficulty associated with approaches to desensitisation based on peptide immunisation lies in how to select an appropriate size and region of the allergen as the basis for the peptide to be used for immunisation. The size of the peptide of choice is crucial. If the peptide is too small, the vaccine would not be effective in inducing an immunological response. If the peptides are too large, or if the whole antigen is introduced into an individual, there is the risk of inducing adverse reactions, such as anaphylaxis, which may be fatal. This risk may be greater if peptides are poorly soluble.

The polypeptides of the invention have been selected to retain T cell specificity whilst being small enough in size to not possess significant tertiary structure that would enable them to retain the conformation of an IgE-binding epitope of the whole molecule. The polypeptides of the invention therefore do not induce significant crosslinking of adjacent specific IgE molecules on cells such as mast cells and basophils and have been shown not to cause significant histamine release from human basophils.

An advantage of the invention is the ability of the peptides to broadly target Major Histocompatibility Complex (MHC) molecules. T cell receptors (TCRs) are highly variable in their specificity. Variability is generated, as with antibody molecules, through gene recombination events within the cell. TCRs recognise antigen in the form of short peptides bound to molecules encoded by the genes of the Major Histocompatibility Complex (MHC). These gene products are the same molecules that give rise to "tissue types" used in transplantation and are also referred to as Human Leukocyte Antigen molecules (HLAs) which terms may be used interchangeably. Individual MHC molecules possess peptide binding grooves which, due to their shape and charge are only capable of binding a limited group of peptides. The peptides bound by one MHC molecule may not necessarily be bound by other MHC molecules.

When a protein molecule such as an antigen or allergen is taken up by antigen presenting cells such as B lymphocytes, dendritic cells, monocytes and macrophages, the molecule is enzymatically degraded within the cell. The process of degradation gives rise to peptide fragments of the molecule which, if they are of the appropriate size, charge and shape, may then bind within the peptide binding groove of certain MHC molecules and be subsequently displayed upon the surface of antigen presenting cells. If the peptide/MHC complexes are present upon the antigen presenting cell surface in sufficient numbers they may then activate T cells which bear the appropriate peptide/MHC-specific T cell receptors.

Due to the polymorphic nature of the MHC, individuals in an outbred population such as man will express different combinations of MHC molecules on their cell surfaces. Since different MHC molecules can bind different peptides from the same molecule based on the size, charge and shape of the peptide, different individuals will display a different repertoire of peptides bound to their MHC molecules. Identification of universal MHC-binding peptide epitopes in an outbred population such as man is more difficult than in inbred animals (such as certain strains of laboratory mice). On the basis of differential MHC expression between individuals and the inherent differences in peptide binding and presentation which this brings, it is unlikely that a single peptide can be identified which will be of use for desensitisation therapy in man.

Another advantage of the invention is the selection of peptides and peptide combinations on the basis of responses observed in PBMCs freshly isolated from ragweed allergic individuals. In contrast to artefactual scenarios where clonal cell lines are established from allergic patients in order to test T cell responses, the evaluation of ex vivo responses of freshly isolated PBMCs allows for a representative view of the relative population importance of different peptides without potential distortion induced by the culture process.

The peptide combinations of the invention, however, provide a broad coverage of efficacy over the human population by targeting multiple different MHC molecules. This broad coverage is illustrated by the ability of peptide combinations of the invention to cause a positive cytokine response in many individuals within the population. A vaccine formulated with the peptides of the invention would therefore have broad utility.

The inventors' work has produced peptide combinations with the following characteristics:

the combination induces a cytokine response in a high proportion of subjects from a panel of ragweed allergic individuals the peptides of the combinations are soluble the peptides of the combinations do not induce significant histamine release in a panel of ragweed allergic individuals.

Accordingly, the present invention provides a composition for use in preventing or treating allergy to ragweed by tolerisation comprising at least one polypeptide selected from SEQ ID Nos. 1 to 31. Typically, the composition comprises at least four polypeptides, wherein the polypeptides are independently selected from any of the following:

(i) a polypeptide of SEQ ID NO's 1 to 31; or (ii) a variant of a polypeptide according to (i), wherein said variant is a polypeptide of length 9 to 30 amino acids that comprises a region consisting of:

any of the sequences of (i); or a sequence which has at least 65% homology to any of the sequences of (i) which sequence is capable of tolerising an individual to any of the sequences of (i); or (iii) a variant of a polypeptide according to (i), wherein said variant is a polypeptide of length 9 to 30 amino acids that comprises a region consisting of a sequence that represents either:

a fragment of any of the sequences of (i); or a homologue of a fragment of any of the sequences of (i), which sequence is capable of tolerising an individual to any of the sequences of (i) and has a length of at least 9 amino acids, and wherein said homologue has at least 65% homology to any 9 contiguous amino acids in any of the sequences of (i).

DESCRIPTION OF THE SEQUENCES MENTIONED HEREIN

Figure 1:
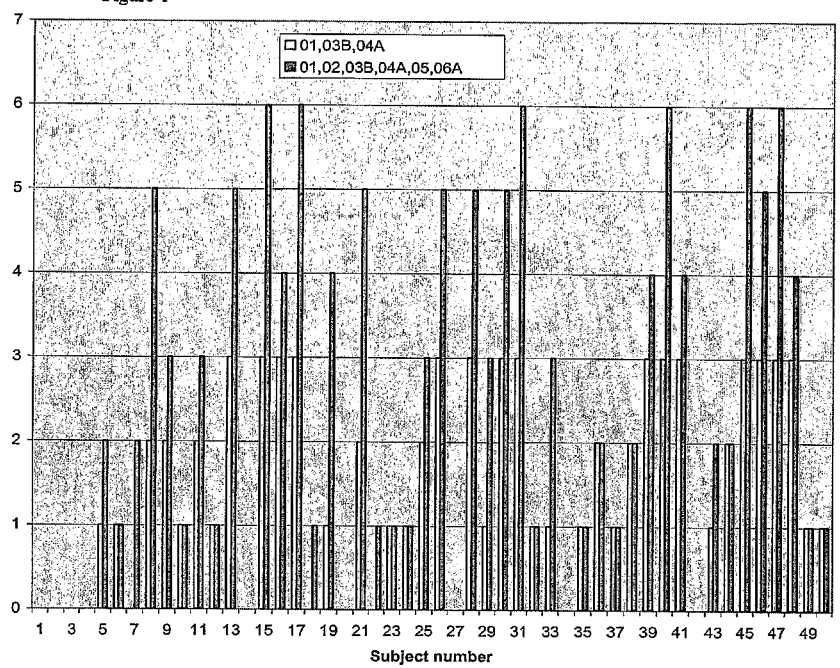
FIG. 1 show the proportion of individuals responsive to different peptide combinations of the invention measured by production of IL-13 or IFN-gamma

SEQ ID NOS: 1 to 31 provide the polypeptide sequences of the invention. SEQ ID NOS: 32 onwards provide additional sequences.

DETAILED DESCRIPTION OF THE INVENTION

The invention concerns peptides and combinations of peptides which can be used in tolerisation. Such peptides may comprise, consist of, or consist essentially of the sequences shown in any of SEQ ID NO's. 1 to 31). Variants of these specific peptides may also be used. The variants may comprise, consist of, or consist essentially of sequences which are fragments of either any of SEQ ID NO's 1 to 31 or homologues of any of SEQ ID NO's 1 to 31.

In one embodiment the invention relates to a composition for use in preventing or treating allergy to ragweed. The composition typically comprises or consists at least four, five, six, seven, eight, nine, ten, eleven, or twelve polypeptides, up to a maximum of thirteen. In other words, the composition comprises between four and thirteen polypeptides. The polypeptides are independently selected from any of the following:
  (i) a polypeptide of SEQ ID NO's 1 to 31; or
  (ii) a variant of a polypeptide according to (i), wherein said variant is a polypeptide of length 9 to 30 amino acids that comprises a region consisting of:
    any of the sequences of (i); or
    a sequence which has at least 65% homology to any of the sequences of (i) which sequence is capable of tolerising an individual to any of the sequences of (i), or
  (iii) a variant of a polypeptide according to (i), wherein said variant is a polypeptide of length 9 to 30 amino acids that comprises a region consisting of a sequence that represents either:
    a fragment of any of the sequences of (i); or
    a homologue of a fragment of any of the sequences of (i), which sequence is capable of tolerising an individual to any of the sequences of (i) and has a length of at least 9 amino acids, and wherein said homologue has at least 65% homology to any 9 contiguous amino acids in any of the sequences of (i).

The invention also provides products and formulations comprising the polypeptides of the invention and compositions, products and vectors comprising polynucleotides capable of expressing the polypeptides of the invention for use in preventing or treating ragweed allergy by tolerisation. Such tolerisation will typically be to an epitope (for example a MHC class II epitope) present in any of SEQ ID NO's 1 to 31.

Ragweed Species

The ragweed species *Ambrosia artemisiifolia* (common ragweed), and to a lesser extent *Ambrosia trifida* (giant ragweed), are responsible for a high proportion of ragweed allergy worldwide, particularly allergies associated with ragweed pollen, such as hayfever. Common ragweed is native to North America, but has spread to most continents worldwide. Ragweeds bloom in the northern hemisphere from early July-mid August or until cooler weather arrives. Ragweed is a pioneer plant which is well adapted to colonising newly disturbed ground. While in natural habitats it is often restricted by competition with other plants, but in areas where humans have cleared existing vegetation, ragweed quickly becomes widely and aggressively established. Thus, ragweed is very abundant along rural roadsides, fence lines, waste lands, new excavations, cultivated fields, gardens, and poorly kept lawns. As such it is well-adapted to wide variety of climates, can tolerate a wide soil pH range (from about 4.5 to about 8.5), and is also resistant to high salinity.

Peptide Fragments of Ragweed Pollen Allergens

The major allergen in ragweed pollen is Amb a 1. This protein exists as a number of different isoforms, Amb a 1.1, 1.2. 1.3 and 1.4. These isoforms are set out in full in Example 1. The present inventors have identified the regions in Amb a 1 which comprise MHC Class II-binding T cell epitopes and which are highly conserved between isoforms (see analysis in Example 1). Based on this information, peptides derived from the relevant regions of Amb a 1 are suitable for preventing or treating ragweed allergy by tolerisation to all isoforms of Amb a 1.

The terms "peptide" and "polypeptide" are used interchangeably herein. The above proteins are also referred to herein as "the allergens".

Tables 3, 4 and 6 set out the sequences of the peptides of the invention, where appropriate indicating the parent protein from which each peptide derives.

Peptide Combinations

The composition typically comprises a combination of at least three different polypeptides of the invention, up to a maximum of thirteen different polypeptides. Accordingly, the composition of the invention may consist of three, four, five, six, seven, eight, nine, ten, eleven, twelve or thirteen peptides.

The polypeptide combinations in the composition of the invention are selected to provide as broad a coverage of the human population as possible, i.e. the composition of the invention will produce an immune response in a high proportion of ragweed allergic individuals, preferably more than 30%, 40%, 45%, 50%, 60% or 70% of ragweed allergic individuals in a panel or population of such individuals. The number of individuals in a population of ragweed allergic individuals may be any suitable number, typically at least 20, 30, 40, 50, 60, 70, 80, or at least 100 individuals. Preferably the population has MHC allele frequencies within the range of frequencies that are representative of the Caucasian population. Reference population allele frequencies for 11 common DRB1 allele families are shown in Table 1 (Data from HLA Facts Book, Parham and Barber).

The composition of the invention typically comprises:

at least one polypeptide selected from a polypeptide of RGW01, RGW01A or RGW01B, or a variant thereof; and at least one polypeptide selected from a polypeptide of RGW03, RGW03A or RGW03B, or a variant thereof; and at least one polypeptide selected from a polypeptide of RGW04 or RGW04A, or a variant thereof Optionally, the composition may additionally comprise at least one additional polypeptide selected from a polypeptide of any of RGW02, RGW09, RGW06 or RGW06A, RGW10, RGW10A, RGW05 or RGW05A, or a variant thereof Optionally, the composition may additionally comprise at least one additional polypeptide selected from a polypeptide of any of RGW07, RGW07C, RGW07D, or a variant thereof. The at least one additional polypeptide is preferably a polypeptide of RGW07D, or a variant thereof.

More specifically, in one embodiment, the invention therefore provides a composition comprising between three and thirteen polypeptides, consisting of:

a) at least one of the polypeptides of RGW01, RGW01A or RGW01B, or a variant thereof, preferably RGW01; and b) at least one of the polypeptides of RGW03, RGW03A or RGW03B, or a variant thereof, preferably RGW03B; and
c) at least one of the polypeptides of any of RGW04 or RGW04A, or a variant thereof, preferably RGW04A; and optionally
d) at least one, preferably two, most preferably three, of the polypeptides of any of RGW02, RGW09, RGW06, RGW06A, RGW10, RGW10A, RGW05 or RGW05A, or a variant thereof, preferably RGW02 and/or RGW06A and/or RGW05; and optionally
e) at least one of the polypeptides of any of RGW07, RGW07C, RGW07D, or a variant thereof, preferably RGW07D.

In other words, one specific embodiment of the invention provides a composition for use in the prevention or treatment of ragweed allergy by tolerisation comprising between three and thirteen peptide sequences, wherein the composition consists of:

a) at least one of the polypeptides with the following sequences:

```
                                      (SEQ ID NO: 1)
RGW01
GMIKSNDGPPI;

(SEQ ID NO: 2)
RGW01A
GLIKSHDGPPV;

(SEQ ID NO: 3)
RGW01B
GLIKSNDGPAA;
``` or a variant thereof, and;

b) at least one of the polypeptides with the following sequences:

```
                                      (SEQ ID NO: 7)
RGW03
KDLLENGAIFVTSQ;

(SEQ ID NO: 8)
RGW03A
DVFENGAIFVPSG;

(SEQ ID NO: 9)
RGW03B
RDLLENGAIFLPSG;
``` or variants thereof and;

c) at least one of the polypeptides with the following sequences:

```
                                      (SEQ ID NO: 10)
RGW04
KAGMIPAEPGEA;

(SEQ ID NO: 11)
RGW4A
SAGMIPAEPGEA;
``` or variants thereof and optionally;

d) at least one of the polypeptides with the following sequences:

```
                                      (SEQ ID NO: 4)
RGW02
GSSQIWIDHSSLSKS;
```

```
                                      (SEQ ID NO: 10)
RGW04
KAGMIPAEPGEA;

(SEQ ID NO: 11)
RGW4A
SAGMIPAEPGEA;

(SEQ ID NO: 14)
RGW06
VVNSDKTIDGRGVKVE;

(SEQ ID NO: 15)
RGW06A
AINNDKTIDGRGAKVE;

(SEQ ID NO: 26)
RGW09
ETRRSLKTSGAYN;

(SEQ ID NO: 27)
RGW10
FGFFQVVNNNYD;

(SEQ ID NO: 28)
RGW10A
HGFFQVVNNNYD;

(SEQ ID NO: 12)
RGW05
KEGTLRFAAAQNRP;

(SEQ ID NO: 13)
RGW05A
KEGTLRFGAAQNRP;
``` or variants thereof and optionally;

e) at least one of the polypeptides with the following sequences:

```
                                      (SEQ ID NO: 16)
RGW07
GEAAIKLTSSAGVLS;

(SEQ ID NO: 19)
RGW07C
KGEAAIKLTSSAGVLSK;

(SEQ ID NO: 20)
RGW07D
KGEAAIKLTSSAGVLSKK;
``` or variants thereof.

It will be appreciated that (a) to (e) above represent stringent and highly selective criteria for the identification of suitable combinations of the invention. For example, if one were to select six peptides at random from the sequences of the invention there would be nearly a million possible combinations to choose from. By contrast, it is useful to consider an example of a combination of six polypeptides in which the above criteria are applied. For example, consider a combination wherein the following polypeptides are selected:

i) any one of the polypeptides of RGW01, RGW01A or RGW01B, and any one of the polypeptides of RGW03, RGW03A or RGW03B and any one of the polypeptides of RGW04 and RGW04A; and ii) three further polypeptides selected from the polypeptides of any of RGW02, RGW09, RGW06, RGW06A, RGW10, RGW10A, RGW05 or RGW05A; and finally Based on such a selection, the number of possible combinations represents a minute fraction of the total available combinations if the criteria determined by the inventors are not applied.

On the basis of the above, a particularly preferred combination of the invention comprises or consists of the polypeptides of RGW01, RGW03B, RGW04A, RGW02, RGW05 and RGW06A, or variants thereof.

A further preferred combination comprises of consists of the polypeptides of RGW01, RGW03B, RGW04A, RGW02, RGW05, RGW06A and RGW07D.

Subject to the above, the composition may optionally comprise further polypeptides up to a total of thirteen unique polypeptides. These further polypeptides relate to (i.e. are typically homologues and/or fragments of) the other sequences, i.e. SEQ ID NOS: 1 to 31, that are not amongst the polypeptides already selected. The further peptides are typically functional variants of one of the peptides of SEQ ID NO's 1 to 31. The further polypeptides may be identical to any of SEQ ID NOS: 1 to 31. The composition may therefore comprise up to thirteen different polypeptides as provided in any of SEQ ID NO: 1 to 31. However, the optional further polypeptides do not need to be 100% identical to any of SEQ ID NO: 1 to 31. They are preferably at least 65% identical to at least 9 (for example at least 10, 11, 12 or 13) or more contiguous amino acids in any of SEQ ID NO: 1 to 31, not already selected amongst the previously selected polypeptide(s). These contiguous amino acids may comprise a MHC class II epitope, for example which binds to any of the MHC molecules mentioned herein. In other words, the composition may optionally comprise further polypeptides up to a total of thirteen unique polypeptides, wherein the further polypeptides:

(i) comprise a sequence having at least 65% sequence identity to at least 9 or more contiguous amino acids in any of SEQ ID NO: 1 to 31 above not selected in (a) to (e) above; and
(ii) are 9 to 30 amino acids in length.
wherein each different polypeptide is for simultaneous, separate or sequential use in the prevention or treatment of ragweed allergy by tolerisation.

In more detail therefore, the invention provides a product containing between three and thirteen polypeptides as defined in (a) to (e) above; and optionally:
(f) A polypeptide:
  (i) comprising sequence having at least 65% sequence identity to at least 9 or more contiguous amino acids in any of SEQ ID NO: 1 to 31 not selected in a), to d) above; and
  (ii) 9 to 30 amino acids in length; and optionally
(g) A polypeptide as defined in f), but additionally not selected in f) above; and optionally
(h) A polypeptide as defined in f), but additionally not selected in f) to g) above; and optionally
(i) A polypeptide as defined in f), but additionally not selected in f) to h) above; and optionally
(j) A polypeptide as defined in f), but additionally not selected in f) to i) above; and optionally
(k) A polypeptide as defined in f), but additionally not selected in f) to j) above) above; and optionally
(l) A polypeptide as defined in f), but additionally not selected in f) to k) above; and optionally
(m) A polypeptide as defined in f), but additionally not selected in f) to l) above; and optionally
(n) A polypeptide as defined in f), but additionally not selected in f) to m) above; and optionally
(o) A polypeptide as defined in f), but additionally not selected in f) to n) above; and optionally
(p) A polypeptide as defined in f), but additionally not selected in f) to o) above for simultaneous, separate or sequential use in the prevention or treatment of ragweed allergy by tolerisation.

Another embodiment of the invention is a composition for use in preventing or treating allergy to ragweed by tolerisation comprising one or more polypeptide, wherein the polypeptide is selected from any of the following:
(i) a polypeptide of any of SEQ ID NO's. 1 to 31; or
(ii) a variant of a polypeptide according to (i), wherein said variant is a polypeptide of length 9 to 30 amino acids that comprises a region consisting of:
  any of the sequences of (i); or
  a sequence which has at least 65% homology to any of the sequences of (i) which sequence is capable of tolerising an individual to any of the sequences of (i), or
(iii) a variant of a polypeptide according to (i), wherein said variant is a polypeptide of length 9 to 30 amino acids that comprises a region consisting of a sequence that represents either:
  a fragment of any of the sequences of (i); or
  a homologue of a fragment of any of the sequences of (i), which sequence is capable of tolerising an individual to any of the sequences of (i) and has a length of at least 9 amino acids, and wherein said homologue has at least 65% homology to any 9 contiguous amino acids in any of the sequences of (i).

The compositions or products of the invention may comprise variants of any of sequences defined above. The variant typically comprises 1, 2, 3 or more of the MHC class II epitopes present in the corresponding peptide of SEQ ID NO: 1 to 31.

Functional variants are mentioned herein. Such variants may be able to tolerise an individual to a class II MHC epitope present in the corresponding peptide of SEQ ID NO: 1 to 31, and thus it will typically comprise sequence that binds to the same MHC class II molecule and/or is recognised by a T cell which recognises the corresponding epitope in the polypeptide of SEQ ID NO: 1 to 31.

Variants of SEQ ID NO's 1 to 31 may be fragments derived by truncation. Truncation refers to the removal of one, two, three, four, five, six, seven, eight, nine, ten or more amino acids from the N and/or C-terminal ends of a polypeptide of SEQ ID NOS. 1 to 31.

Fragments may also be generated by one or more internal deletions, provided that the core 9 amino acids that makes up the T cell epitope is not substantially disrupted.

For example, a variant of SEQ ID NO: 1 may comprise a fragment of SEQ ID NO: 1, i.e. a shorter sequence. This may include a deletion of one, two, three, four, five, six, seven, eight, nine, ten or more amino acids from the N-terminal end of SEQ ID NO: 1 or from the C-terminal end of SEQ ID NO: 1. Such deletions may be made from both ends of SEQ ID NO: 1. A variant of SEQ ID NO: 1 may include additional amino acids (for example from the sequence of the parent protein from which the peptide derives) extending beyond the end(s) of SEQ ID NO: 1. A variant may include a combination of the deletions and additions discussed above. For example, amino acids may be deleted from one end of SEQ ID NO: 1, but additional amino acids from the full length parent protein sequence may be added at the other end of SEQ ID NO: 1. The same discussion of variants above also applies to SEQ ID NOS: 2 to 31. A preferred variant of SEQ ID NO: 20 is the peptide KKGEAAIKLTSSAGVLSK (SEQ ID NO: 150).

A variant peptide may include one or more amino acid substitutions from the amino acid sequence of any of SEQ ID NOS: 1 to 31 or a fragment thereof. A variant peptide may comprise sequence having at least 65% sequence identity to at least 9 or more contiguous amino acids in any of SEQ ID NOS: 1 to 31. More preferably a suitable variant may comprise at least 70%, at least 75%, at least 80%, at least 85%, at least 90%, at least 95%, or at least 98% amino acid identity to at least 9 contiguous amino acids of any of SEQ ID NO: 1 to 31. This level of amino acid identity may be seen at any section of the peptide, although it is preferably the core region. The level of amino acid identity is over at least 9 contiguous amino acids but it may be at least 10, 11, 12, 13, 14, 15 or at least 16 or 17 amino acids, depending on the size of the peptides of comparison. Accordingly, any of the above-specified levels of identity may be across the entire length of sequence.

In connection with amino acid sequences, "sequence identity" refers to sequences which have the stated value when assessed using ClustalW (Thompson et al, Nucleic Acids Res. 1994 Nov. 11; 22(22):4673-80) with the following parameters: Pairwise alignment parameters—Method: accurate, Matrix: PAM, Gap open penalty: 10.00, Gap extension penalty: 0.10; Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatised.

A variant peptide may comprise 1, 2, 3, 4, 5 or more, or up to 10 amino acid substitutions from any of SEQ ID NOS: 1 to 31. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
| --- | --- | --- | --- |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

Further variants include those in which instead of the naturally occurring amino acid the amino acid which appears in the sequence is a structural analog thereof. Amino acids used in the sequences may also be modified, e.g. labelled, providing the function of the peptide is not significantly adversely affected.

Where the peptide has a sequence that varies from the sequence of any of SEQ ID NOS: 1 to 31 or a fragment thereof, the substitutions may occur across the full length of the sequence, within the sequence of any of SEQ ID NOS: 1 to 31 or outside the sequence of any of SEQ ID NOS: 1 to 31. For example, the variations described herein, such as additions, deletions, substitutions and modifications, may occur within the sequence of any of SEQ ID NOS: 1 to 31. A variant peptide may comprise or consist essentially of the amino acid sequence of any of SEQ ID NOS: 1 to 31 in which one, two, three, four or more amino acid substitutions have been made. A variant peptide may comprise a fragment of the parent protein that is larger than any of SEQ ID NOS: 1 to 31. In this embodiment, the variations described herein, such as substitutions and modifications, may occur within and/or outside the sequence of any of SEQ ID NOS: 1 to 31.

The variant peptides of the invention are 9 to 30 amino acids in length inclusive. Preferably, they may be from 9 to 20 or more preferably 13 to 17 amino acids in length. The peptides may be the same length as the peptide sequences in any one of SEQ ID NOS: 1 to 31.

The peptides may be chemically derived from the polypeptide allergen, for example by proteolytic cleavage or can be derived in an intellectual sense from the polypeptide allergen, for example by making use of the amino acid sequence of the polypeptide allergen and synthesising peptides based on the sequence. Peptides may be synthesised using methods well known in the art.

Where polypeptides comprise residues which are typically difficult to preserve during manufacture, these residues may be replaced. For example, glutamate spontaneously forms pyroglutamate in solution particularly when present at the N terminus of a peptide. Thus, residues of the peptides of the invention which correspond to a glutamate or glutamine residue in the sequence of a native allergen protein sequence may be replaced with pyroglutamate in the peptides of the invention when such a residue is present at the N terminus of a peptide.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine Other examples of modifications include glycosylation and phosphorylation. Another potential modification is that hydrogens on the side chain amines of R or K may be replaced with methylene groups (—$NH_2$→—NH(Me) or —$N(Me)_2$).

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

The peptides provided by the present invention may be derived from splice variants of the parent proteins encoded by mRNA generated by alternative splicing of the primary transcripts encoding the parent protein chains. The peptides may also be derived from amino acid mutants, glycosylation variants and other covalent derivatives of the parent proteins which retain at least an MHC-binding property of the allergens. Exemplary derivatives include molecules wherein the peptides of the invention are covalently modified by substitution, chemical, enzymatic, or other appropriate means with a moiety other than a naturally occurring amino acid. Further included are naturally occurring variants of the parent proteins found in different mites. Such a variant may be encoded by an allelic variant or represent an alternative splicing variant.

Variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

In accordance with the invention, the further peptides that the composition may comprise are preferably functional variants of any of SEQ ID NOS: 1 to 31. That is, the peptides are preferably capable of inducing an immune response. In particular, the peptides are preferably capable of inducing cytokine production in ragweed allergic individuals. Typically, the composition of the invention will therefore comprise at least one polypeptide or variant thereof which produces a cytokine response in greater than 45, 50, 55%, preferably 60% or 65% of individuals in a population of ragweed allergic individuals. The number of individuals in a panel of ragweed allergic individuals may be any number greater than one, for example at least 20, 30, 40, 50, 80, or at least 100 individuals. Preferably the composition comprises at least two, three or most preferably four such peptides. Preferably the cytokine response is production of IL-13 or IFN-gamma Cytokine production may be measured by any suitable method. Production of a cytokine is typically considered to have occurred in response to a peptide if the level of cytokine produced in the presence of the peptide is at least 2, 3, 4 or 5 fold above the background level of said cytokine that is produced in the absence of a stimulus (i.e. the level produced by the same individual in the absence of the peptide or any other stimulus). Alternatively, production of a cytokine may be considered to have occurred if the amount of cytokine produced exceeds a recognised limit, typically 90, 95, or preferably 100 pg/ml, typically from a sample of approximately $1.25 \times 10^6$ cells in 250 µl.

Suitable methods for measuring cytokine production typically include measuring the cytokine release from peripheral blood mononuclear cells (PBMCs) from a taken sample from a subject. The sample is typically blood or serum. Cytokine release from PBMCs is measured after incubating the cells in the presence of a given peptide. Supernatants from the incubation mixture are then tested for the presence of a cytokine, using any suitable assay, for example an ELISA, ELISPOT assay or flow cytometric assay. Particularly preferred methods include Multiplex bead array assays as described in, for example de Jager et al; Clinical and Diagnostic Laboratory Immunology, 2003, Vol 10(1) p. 133-139. Typically, the composition may comprise at least one additional peptide or variant thereof that is not amongst the polypeptides already selected, upto a total of thirteen different peptides, which produces a cytokine response in greater than 30%, 35%, 40%, preferably 45% or 50% of individuals in a population of ragweed allergic individuals.

The composition may further comprise one or more additional peptides or variants thereof that are not amongst the polypeptides already selected, upto a total of thirteen different peptides, which produce a cytokine response in greater than 10%, 15%, 20%, 25%, preferably 30% or 35% of individuals in a population of ragweed allergic individuals.

The composition may further comprise one or more additional peptides which induce release of IL-10. IL-10 is known as an immune modulator which can shift T cell responses away from an allergic-type response. A significant IL-10 release may lead to induction of regulatory T cells which give rise to or improve toleration of the presence of the other peptides of the composition.

Preferably, said peptide may induce release of IL-10 in at least 35, 40, 45, 50 or 55% of a population. In this embodiment, the peptide is therefore able to bind to a subset of MHC alleles which is representative of an equivalent proportion of the sample population. Preferably, the peptides induce IL-10 release in 55% or more, 65% or more, 70% or more, 75% or more, 80% or more, 85% or more, or 90% or more of a population.

"Induction of IL-10 release" is herein defined as a release which is measurable by methods commonly used in the art. Typically, the response is measured in vitro using T cells obtained from the allergic individuals. An "induction" is scored as an IL-10 level which is greater than that observed in a control sample where T cells are not exposed to the peptide. In some embodiments, an induction of IL-10 release suitable for tolerisation may be defined as an IL-10 release at least 35, 40, 45, 50 or 55% of the average amount of IL-10 released in response to the whole protein allergen of which the first polypeptide is a fragment. It should be understood that the protein allergen used as a comparison may be the whole intact polypeptide or may be a truncated form that comprises the T cell epitopes which mediate immune response to the protein allergen. Commonly, individual peptides derived from the protein allergen will show an average IL-10 release that is much lower than that obtained in response to the whole or truncated protein allergen as defined above. However, individual peptides that show IL-10 release at least 35, 40, 45, 50 or 55% of the IL-10 release to the whole or truncated protein allergen may be particularly suitable tolerising agents. The peptides may also display an average response that is the same as, or greater than, the response observed in response to whole or truncated protein allergen.

Alternatively the average level of IL-10 released may be measured in absolute terms, in which case an average level above approximately 400, 450, 500 or 550 pg/ml will be considered to be an induction, typically from a sample of approximately $1.25 \times 10^6$ cells in 250 µl.

It should be understood that average may be the mean, median or mode of the individual IL-10 releases observed in the population. It should be understood that where an individual in the population displays an unusually low or unusually high IL-10 release in comparison to the other members of the population, they may be excluded from the average. This may allow for measurement of an average that is more representative of the responses shown in the population. The term 'unusually low' or unusually high' may refer to differentials of 10-fold or 20-fold as compared to a more representative average of the IL-10 releases that excludes the individuals showing unusual IL-10 release characteristics.

Suitable variants capable of binding to TCRs may be derived empirically or selected according to known criteria.

Within a single peptide there are certain residues which contribute to binding within the MHC antigen binding groove and other residues which interact with hypervariable regions of the T cell receptor (Allen et al (1987) Nature 327: 713-5).

Within the residues contributing to T cell receptor interaction, a hierarchy has been demonstrated which pertains to dependency of T cell activation upon substitution of a given peptide residue. Using peptides which have had one or more T cell receptor contact residues substituted with a different amino acid, several groups have demonstrated profound effects upon the process of T cell activation. Evavold & Allen (1991) Nature 252: 1308-10) demonstrated the dissociation of T cell proliferation and cytokine production. In this in vitro model, a T cell clone specific for residues 64-76 of haemoglobin (in the context of I-$E^k$), was challenged with a peptide analogue in which a conservative substitution of aspartic acid for glutamic acid had been made. This substitution did not significantly interfere with the capacity of the analogue to bind to I-$E^k$.

Following in vitro challenge of a T cell clone with this analogue, no proliferation was detected although IL-4 secretion was maintained, as was the capacity of the clone to help B cell responses. In a subsequent study the same group demonstrated the separation of T cell-mediated cytolysis from cytokine production. In this instance, the former remained unaltered while the latter was impaired. The efficacy of altered peptide ligands in vivo was initially demonstrated in a murine model of EAE (experimental allergic encephalomyelitis) by McDevitt and colleagues (Smilek et al (1991) Proc Natl Acad Sci USA 88: 9633-9637). In this model EAE is induced by immunisation with the encephalitogenic peptide Ac1-11 of MBP (myelin basic protein). Substitution at position four (lysine) with an alanine residue generated a peptide which bound well to its restricting element ($A\alpha^u A\beta^u$), but which was non-immunogenic in the susceptible PL/JxSJLF 1 strain and which, furthermore prevented the onset of EAE when administered either before or after immunisation with the encephalitogenic peptide. Thus, residues can be identified in peptides which affect the ability of the peptides to induce various functions of T-cells.

Advantageously, peptides may be designed to favour T-cell proliferation and induction of desensitisation. Metzler and Wraith have demonstrated improved tolerogenic capacity of peptides in which substitutions increasing peptide-MHC affinity have been made (Metzler & Wraith(1993) Int Immunol ~: 1159-65). That an altered peptide ligand can cause long-term and profound anergy in cloned T cells was demonstrated by Sloan-Lancaster et al (1993) Nature 363: 156-9.

The compositions of the invention are capable of inducing a late phase response in an individual that is sensitised to the allergens. The term "late phase response" includes the meaning as set forth in Allergy and Allergic Diseases (1997) A. B. Kay (Ed.), Blackwell Science, pp 1113-1130. The late phase response may be any late phase response (LPR). Preferably, the peptides are capable of inducing a late asthmatic response (LAR) or a late rhinitic response, or a late phase skin response or a late phase ocular response. Whether or not a particular peptide can give rise to a LPR can be determined using methods well known in the art; a particularly preferred method is that described in Cromwell O, Durham S R, Shaw R J, Mackay J and Kay A B. Provocation tests and measurements of mediators from mast cells and basophils in asthma and allergic rhinitis. In: Handbook of Experimental Immunology (4) Chapter 127, Editor: Weir D M, Blackwell Scientific Publications, 1986.

Thus, preferably, the individual peptides of the invention are able to induce a LPR in an individual who has been sensitised to the allergens. Whether or not an individual has been sensitised to the allergens may be determined by well known procedures such as skin prick testing with solutions of allergen extracts, induction of cutaneous LPRs, clinical history, allergen challenge and radioallergosorbent test (RAST) for measurement of allergen specific IgE. Whether or not a particular individual is expected to benefit from treatment may be determined by the physician based, for example, on such tests.

Desensitising or tolerising an individual to the allergens means inhibition or dampening of allergic tissue reactions induced by the allergens in appropriately sensitised individuals. It has been shown that T cells can be selectively activated, and then rendered unresponsive. Moreover the anergising or elimination of these T-cells leads to desensitisation of the patient for a particular allergen. The desensitisation manifests itself as a reduction in response to an allergen or allergen-derived peptide, or preferably an elimination of such a response, on second and further administrations of the allergen or allergen-derived peptide. The second administration may be made after a suitable period of time has elapsed to allow desensitisation to occur; this is preferably any period between one day and several weeks. An interval of around two weeks is preferred.

Although the compositions of the invention are able to induce a LPR in a ragweed allergic individual, it should be appreciated that when a composition is used to treat a patient it is preferable that a sufficiently low concentration of the composition is used such that no observable LPR will occur but the response will be sufficient to partially desensitise the T cells such that the next (preferably higher) dose may be given, and so on. In this way the dose is built up to give full desensitisation but often without ever inducing a LPR in the patient. Although, the composition or peptide is able to do so at a higher concentration than is administered.

The compositions of the invention preferably are capable of inducing a late phase response in 50% or more of a panel of ragweed allergic individuals from the population. More preferably, the compositions are capable of inducing a LPR in 55% or more, 60% or more, 65% or more, 70% or more, 75% or more, 80% or more, 85% or more, or 90% or more of sensitized individuals in a panel. Whether or not the compositions are able to induce a LPR in a certain percentage of a panel of subjects can be determined by methods which are well known in the art.

It will be understood that the peptides of the invention comprise a T cell epitope that consists of a core 9 amino acids which are the minimal essential sequence required for MHC class II binding. However, the peptides may also comprise additional residues flanking the core 9 amino acids. The peptides may therefore comprise a region containing a T cell epitope, in which some residues may be modified without affecting the function of the epitope. Accordingly, functional variants of the peptides as defined above include peptides which are altered to improve their solubility relative to the native sequence of the peptides. Improved solubility is advantageous for the tolerisation of subjects to allergens from which the peptides of the invention derive, since administration of poorly soluble agents to subjects causes undesirable, non-tolerising inflammatory responses. The solubility of the peptides may be improved by altering the residues which flank the region containing a T cell epitope. A peptide of the invention may be engineered to be more soluble such that it comprises:

i) N terminal to the residues of the peptide which flank a T cell epitope: one to six contiguous amino acids corresponding to the two to six contiguous amino acids immediately N terminal to said residues in the sequence of the protein from which the peptide derives; and/or ii) C terminal to the residues of the peptide which flank a T cell epitope: one to six contiguous amino acids corresponding to the one to six contiguous amino acids immediately C terminal to the said residues in the sequence of the protein from which the peptide derives; or iii) N and/or C terminal to the residues of the peptide which flank a T cell epitope, at least one amino acid selected from arginine, lysine, histidine, glutamate and aspartate.

Optionally, the peptides may additionally be engineered to be more soluble such that:

i) any cysteine residues in the native sequence of the peptide are replaced with serine or 2-aminobutyric acid; and/or ii) any residues at the N and/or C terminus of the native sequence of the peptide, which are not comprised in a T cell epitope, are deleted; and/or iii) any two consecutive amino acids comprising the sequence Asp-Gly in the upto four amino acids at the N and/or C terminus of the native sequence of the peptide, which are not comprised in a T cell epitope, are deleted.

Nucleic Acids and Vectors

The individual peptides that make up the compositions and products of the invention may be administered directly, or may be administered indirectly by expression from an encoding sequence. For example, a polynucleotide may be provided that encodes a peptide of the invention, such as any of the peptides described above. A peptide of the invention may thus be produced from or delivered in the form of a polynucleotide which encodes, and is capable of expressing, it. Any reference herein to the use, delivery or administration of a peptide of the invention is intended to include the indirect use, delivery or administration of such a peptide via expression from a polynucleotide that encodes it.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1931, Molecular Cloning—a laboratory manual; Cold Spring Harbor Press).

The polynucleotide molecules of the present invention may be provided in the form of an expression cassette which includes control sequences operably linked to the inserted sequence, thus allowing for expression of the peptide of the invention in vivo in a targeted subject. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a peptide of the invention.

The present invention thus includes expression vectors that comprise such polynucleotide sequences. Thus, the present invention provides a vector for use in preventing or treating allergy to ragweeds by tolerisation comprising four or more polynucleotide sequences which encode different polypeptides of the invention and optionally one or more further polynucleotide sequences which encode different polypeptides as defined herein. The vector may comprise 4, 5, 6 or 7 polynucleotide sequences which encode different polypeptides of the invention.

Furthermore, it will be appreciated that the compositions and products of the invention may comprise a mixture of polypeptides and polynucleotides. Accordingly, the invention provides a composition or product as defined herein, wherein in place of any one of the polypeptide is a polynucleotide capable of expressing said polypeptide.

Expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus. Thus, a peptide of the invention may be provided to an individual by expression from cells within the individual, and secretion from those cells.

Alternatively, polynucleotides of the invention may be expressed in a suitable manner to allow presentation of a peptide of the invention by an MHC class II molecule at the surface of an antigen presenting cell. For example, a polynucleotide, expression cassette or vector of the invention may be targeted to antigen presenting cells, or the expression of encoded peptide may be preferentially stimulated or induced in such cells.

Polynucleotides of interest may be used in vitro, ex vivo or in vivo in the production of a peptide of the invention. Such polynucleotides may be administered or used in the prevention or treatment of allergy by tolerisation.

Methods for gene delivery are known in the art. See, e.g., U.S. Pat. Nos. 5,399,346, 5,580,859 and 5,531,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells that have been removed from a subject. For example, a polynucleotide, expression cassette or vector of the invention may be introduced into APCs of an individual ex vivo. Cells containing the nucleic acid molecule of interest are re-introduced into the subject such that an immune response can be mounted against the peptide encoded by the nucleic acid molecule. The nucleic acid molecules used in such immunization are generally referred to herein as "nucleic acid vaccines."

The polypeptides, polynucleotides, vectors or cells of the invention may be present in a substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the proteins, polynucleotides, cells or dry mass of the preparation.

Antigen Presenting Cells (APCs)

The invention encompasses the use in vitro of a method of producing a population of APCs that present the peptides of the invention on their surface, that may be subsequently used in therapy. Such a method may be carried out ex vivo on a sample of cells that have been obtained from a patient. The APCs produced in this way therefore form a pharmaceutical agent that can be used in the treatment or prevention of ragweed allergy by tolerisation. The cells should be accepted by the immune system of the individual because they derive from that individual. Delivery of cells that have been produced in this way to the individual from whom they were originally obtained, thus forms a therapeutic embodiment of the invention.

Formulations and Compositions

The peptides, polynucleotides, vectors and cells of the invention may be provided to an individual either singly or in combination. Each molecule or cell of the invention may be provided to an individual in an isolated, substantially isolated, purified or substantially purified form. For example, a peptide of the invention may be provided to an individual substantially free from the other peptides.

Whilst it may be possible for the peptides, polynucleotides or compositions according to the invention to be presented in raw form, it is preferable to present them as a pharmaceutical formulation. Thus, according to a further aspect of the invention, the present invention provides a pharmaceutical formulation for use in preventing or treating allergy to ragweeds by tolerisation comprising a composition, vector or product according to the invention together with one or more pharmaceutically acceptable carriers or diluents and optionally one or more other therapeutic ingredients. The carrier (s) must be 'acceptable' in the sense of being compatible with the other ingredients of the formulation and not deleterious to the recipient thereof. Typically, carriers for injection, and the final formulation, are sterile and pyrogen free.

Formulation of a composition comprising the peptide, polynucleotides or cells of the invention can be carried out using standard pharmaceutical formulation chemistries and methodologies all of which are readily available to the reasonably skilled artisan.

For example, compositions containing one or more molecules or cells of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e. g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the peptides or polynucleotides of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulation of any of the peptides, polynucleotides or cells mentioned herein will depend upon factors such as the nature of the substance and the method of delivery. Any such substance may be administered in a variety of dosage forms. It may be administered orally (e.g. as tablets, troches, lozenges, aqueous or oily suspensions, dispersible powders or granules), parenterally, epicutaneously, subcutaneously, by inhalation, intravenously, intramuscularly, intrasternally, transdermally, intradermally, sublingually, instranasally, buccally or by infusion techniques. The substance may also be administered as suppositories. A physician will be able to determine the required route of administration for each particular individual.

The compositions of formulations of the invention will comprise a suitable concentration of each peptide/polynucleotide/cell to be effective without causing adverse reaction. Typically, the concentration of each peptide in the composition will be in the range of 0.03 to 200 nmol/ml. More preferably in the range of 0.3 to 200 nmol/ml, 3 to 180 nmol/ml, 10 to 150 nmol/ml or 30 to 120 nmol/ml. The composition or formulations should have a purity of greater than 95% or 98% or a purity of at least 99%.

In one embodiment, therefore, the peptides, polynucleotides, cells or compositions of the invention are used for therapy in combination with one or more other therapeutic agents. The agents may be administered separately, simultaneously or sequentially. They may be administered in the same or different compositions. Accordingly, in a method of the invention, the subject may also be treated with a further therapeutic agent.

A composition may therefore be formulated which comprises a molecule and/or cell of the invention and also one or more other therapeutic molecules. A composition of the invention may alternatively be used simultaneously, sequentially or separately with one or more other therapeutic compositions as part of a combined treatment.

Therapeutic Methods and Individual to be Treated

The present invention relates to peptides, polynucleotides, vectors and cells that are capable of desensitising or tolerising human individuals to the allergens described above and are therefore useful in the prevention or treatment of ragweed allergy. The invention provides compositions, products, vectors and formulations for use in preventing or treating allergy to ragweeds by tolerisation. The invention also provides a method of tolerising or desensitizing a ragweed allergic individual comprising administering, either singly or in combination the polypeptides/polynucleotides/cells of the invention as described above.

The individual to be treated or provided with the composition or formulation of the invention is preferably human. It will be appreciated that the individual to be treated may be known to be sensitised to the allergens, at risk of being sensitised or suspected of being sensitised. The individual can be tested for sensitisation using techniques well known in the art and as described herein. Alternatively, the individual may have a family history of allergy to ragweed. It may not be necessary to test an individual for sensitisation to ragweed because the individual may display symptoms of allergy when exposed to ragweed. By exposure is meant proximity to, for example, a ragweed plant, or a substance or product derived from a ragweed plant, or a substance or product containing or comprising either of the above. The substance or product derived from a ragweed plant is typically ragweed pollen. By proximity is meant 10 meters or less, 5 meters or less, 2 meters or less, 1 meter or less, or 0 meters from the items described above. Symptoms of allergy can include itchy eyes, runny nose, breathing difficulties, red itchy skin or rash.

The individual to be treated may be of any age. However, preferably, the individual may be in the age group of 1 to 90, 5 to 60, 10 to 40, or more preferably 18 to 35.

Preferably, the individual to be treated is from a population that has MHC allele frequencies within the range of frequencies that are representative of the Caucasian population. Reference population allele frequencies for 11 common DRB1 allele families are shown in Table 1 (Data from HLA Facts Book, Parham and Barber).

TABLE 1

| DRB1 | 1 | 3 | 4 | 7 | 8 | 11 | 12 | 13 | 14 | 15 | 16 |
|---|---|---|---|---|---|---|---|---|---|---|---|
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Reference frequencies were obtained by analysis of multiple studies reporting frequencies and the figures shown are mean values. Preferably therefore, the individual to be treated is from a population that has equivalent MHC allele frequencies as the reference population for the alleles referred to Table 1 (such as for at least 1, 2, 3, 4, 5 or all of the alleles), for example within the ranges of those figures plus or minus 1, 2, 3, 5, 10, 15 or 20%.

Preferably the individual is from a population where the allele frequencies of the following DRB1 alleles is:
4—at least 9%
7—at least 10%
11—at least 8%.

The individual may have had allergy to ragweeds for at least 2 weeks, 1 month, 6 months, 1 year or 5 years. The individual may suffer from a rash, nasal congestion, nasal discharge and/or coughing caused by the allergy. The individual may or may not have been administered with other compositions/compounds which treat ragweed allergy.

The individual typically lives in a geographical region with a warm and moist climate. The individual typically suffers from allergy to ragweed in a particular season. The season typically corresponds to the flowering season of ragweed, which is typically summer to Autumn, preferably late summer (for July to August in the Northern hemisphere) to early Autumn (September to October in the Northern hemisphere). The ragweed allergic individual is typically allergic to ragweed pollen.

Combination Immunotherapy

Since many individuals are allergic, or may require desensitizing to several polypeptide antigens, the current invention also provides means of desensitizing m individuals that are allergic to multiple antigens. "Tolerance" induced in an individual to a first polypeptide antigen or allergen can create in the individual a "tolergeneic environment" wherein inappropriate immune responses to other antigens can be downregulated in order to provide tolerance to other antigens.

This finding means that individuals allergic to multiple allergens can be treated in a greatly reduced time period, and that individuals seriously allergic to some allergens (e.g., peanuts) but more mildly allergic to other allergens (e.g., cat dander) can benefit from a therapy wherein tolerance to the milder allergen is established and then this tolergeneic environment is used to provide tolerance to the other, more extreme allergen. In addition, individuals suffering from an autoimmune disorder who are additionally sensitised (or otherwise immune) to an unrelated antigen or allergen can benefit from a treatment regime wherein tolerance to the unrelated antigen or allergen is first established and then this tolergeneic environment is used to provide tolerance to the autoantigen associated with the autoimmune disorder.

A method is therefore provided for desensitising a ragweed allergic individual to ragweed allergen as described above and one or more further different polypeptide antigens. The method entails, in a first step, administering to the individual a composition/product/formulation (primary composition) according to the invention as described herein and wherein the administration is carried out in a manner sufficient to generate a hyporesponsive state against ragweed allergen. Once a hyporesponsive state has been established toward ragweed allergen, or at least a shift toward desensitisation has occurred, the method entails administration of a secondary composition comprising a second, different polypeptide antigen to which the individual is to be sensitised. Administration of the secondary composition is carried out in such a way as to take advantage of the tolergeneic environment established by use of the primary composition, where it is now possible to establish tolerance to the second, different polypeptide antigen. The secondary composition is coadministered with either the first primary composition or a larger fragment of the allergen from which the primary composition derives. By "coadministered" it is meant either the simultaneous or concurrent administration, e.g., when the two are present in the same composition or administered in separate compositions at nearly the same time but at different sites, as well as the delivery of polypeptide antigens in separate compositions at different times. For example, the secondary composition may be delivered prior to or subsequent to delivery of the first composition at the same or a different site. The timing between deliveries can range from about several seconds apart to about several minutes apart, several hours apart, or even several days apart. Furthermore, different delivery methods can be employed.

The second polypeptide antigen is preferably an allergen different to the ragweed allergen. Suitable allergens for use in the methods of the invention can of course be obtained and/or produced using known methods. Classes of suitable allergens include, but are not limited to, other ragweed allergens, pollens, animal dander (especially cat dander), grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as Alternaria, Fusarium, Hormodendrum, Aspergillus, Micropolyspora, Mucor and thermophilic actinomycetes; epidermal allergens can be obtained from house or organic dusts (typically fungal in origin), or from animal sources such as feathers, and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major cat allergen Fel dl, bee venom phospholipase A2 (PLA) (Akdis et al. (1996) *J. Clin. Invest.* 98:1676-1683), birch pollen allergen Bet v 1 (Bauer et al. (1997) *Clin. Exp. Immunol.* 107:536-541), and the multi-epitopic recombinant grass allergen rKBG8.3 (Cao et al. (1997) *Immunology* 90:46-51). These and other suitable allergens are commercially available and/or can be readily prepared as extracts following known techniques.

Preferably, the second polypeptide allergen is selected from the list of allergen sequences and database accession numbers (NCBI Entrez accession numbers) below. NCBI is the National Center for Biotechnology information and is a division of the US National Institutes of Health. The NCBI web site, from which access to the database may be sought, is www.ncbi.nlm.nih.gov/. Allergen sequences and database accession numbers (NCBI Entrez accession numbers): *Dermatophagoides pteronyssinus*

(SEQ ID NO: 47)
Der p 1
MKIVLAIASLLALSAVYARPSSIKTFEEYKKAFNKSYATFEDEEAARKN
FLESVKYVQSNGGAINHLSDLSLDEFKNRFLMSAEAFEHLKTQFDLNAE
TNACSINGNAPAEIDLRQMRTVTPIRMQGGCGSCWAFSGVAATESAYLA
YRNQSLDLAEQELVDCASQHGCHGDTIPRGIEYIQHNGVVQESYYRYVA
REQSCRRPNAQRFGISNYCQIYPPNVNKIREALAQTHSAIAVIIGIKDL
DAFRHYDGRTIIQRDNGYQPNYHAVNIVGYSNAQGVDYWIVRNSWDTNW
GDNGYGYFAANIDLMMIEEYPYVVIL (SEQ ID NO: 48)
Der p 2
MMYKILCLSLLVAAVARDQVDVKDCANHEIKKVLVPGCHGSEPCIIHRG
KPFQLEAVFEANQNTKTAKIEIKASIDGLEVDVPGIDPNACHYMKCPLV
KGQQYDIKYTWNVPKIAPKSENVVVTVKVMGDDGVLACAIATHAKIRD (SEQ ID NO: 49)
Der p 3
MIIYNILIVLLLAINTLANPILPASPNATIVGGEKALAGECPYQISLQS
SSHFCGGTILDEYWILTAAHCVAGQTASKLSIRYNSLKHSLGGEKISVA
KIFAHEKYDSYQIDNDIALIKLKSPMKLNQKNAKAVGLPAKGSDVKVGD
QVRVSGWGYLEEGSYSLPSELRRVDIAVVSRKECNELYSKANAEVTDNM
ICGGDVANGGKDSCQGDSGGPVVDVKNNQVVGIVSWGYGCARKGYPGVY
TRVGNFIDWIESKRSQ (SEQ ID NO: 50)
Der p 4
KYXNPHFIGXRSVITXLME (SEQ ID NO: 51)
Der p 5
MKFIIAFFVATLAVMTVSGEDKKHDYQNEFDFLLMERIHEQIKKGELAL
FYLQEQINHFEEKPTKEMKDKIVAEMDTIIAMIDGVRGVLDRLMQRKDL
DIFEQYNLEMAKKSGDILERDLKKEEARVKKIEV (SEQ ID NO: 52)
Der p 6
AIGXQPAAEAEAPFQISLMK (SEQ ID NO: 53)
Der p 7
MMKLLLIAAAAFVAVSADPIHYDKITEEINKAVDEAVAAIEKSETFDPM
KVPDHSDKFERHIGIIDLKGELDMRNIQVRGLKQMKRVGDANVKSEDGV
VKAHLLVGVHDDVVSMEYDLAYKLGDLHPNTHVISDIQDFVVELSLEVS
EEGNMTLTSFEVRQFANVVNHIGGLSILDPIFAVLSDVLTAIFQDTVRA
EMTKVLAPAFKKELERNNQ (SEQ ID NO: 54)
Der p9
IVGGSNASPGDAVYQIAL

*Dermatophagoides farinae*

(SEQ ID NO: 55)
Der f 1
MKFVLAIASLLVLTVYARPASIKTFEFKKAFNKNYATVEEEEVARKNFL
ESLKYVEANKGAINHLSDLSLDEFKNRYLMSAEAFEQLKTQFDLNAETS
ACRINSVNVPSELDLRSLRTVTPIRMQGGCGSCWAFSGVAATESAYLAY

RNTSLDLSEQELVDCASQHGCHGDTIPRGIEYIQQNGVVEERSYPYVAR
EQRCRRPNSQHYGISNYCQIYPPDVKQIREALTQTHTAIAVIIGIKDLR
AFQHYDGRTIIQHDNGYQPNYHAVNIVGYGSTQGDDYWIVRNSWDTTWG
DSGYGYFQAGNNLMMIEQYPYVVIM (SEQ ID NO: 56)
Der f 2
MISKILCLSLLVAAVVADQVDVKDCANNEIKKVMVDGCHGSDPCIIHRG
KPFTLEALFDANQNTKTAKIEIKASLDGLEIDVPGIDTNACHFMKCPLV
KGQQYDIKYTWNVPKIAPKSENVVVTVKLIGDNGVLACAIATHGKIRD (SEQ ID NO: 57)
Der f 3
MMILTIVVLLAANILATPILPSSPNATIVGGVKAQAGDCPYQISLQSSS
HFCGGSILDEYWILTAAHCVNGQSAKKLSIRYNTLKHASGGEKIQVAEI
YQHENYDSMTIDNDVALIKLKTPMTLDQTNAKPVPLPAQGSDVKVGDKI
RVSGWGYLQEGSYSLPSELQRVDIDVVSREQCDQLYSKAGADVSENMIC
GGDVANGGVDSCQGDSGGPVVDVATKQIVGIVSWGYGCARKGYPGVYTR
VGNFVDWIESKRSQ (SEQ ID NO: 58)
Der f 4
AVGGQDADLAEAPFQISLLK (SEQ ID NO: 59)
Der f 7
MMKFLLIAAVAFVAVSADPIHYDKITEEINKAIDDAIAAIEQSETIDPM
KVPDHADKFERHVGIVDFKGELAMRNIEARGLKQMKRQGDANVKGEEGI
VKAHLLIGVHDDIVSMEYDLAYKLGDLHPTTHVISDIQDFVVALSLEIS
DEGNITMTSFEVRQFANVVNHIGGLSILDPIFGVLSDVLTAIFQDTVRK
EMTKVLAPAFKRELEKN

Additional mite allergen sequences (NCBI entrez accession):
1170095; 1359436; 2440053; 666007; 487661; 1545803; 84702; 84699; 625532; 404370; 1091577; 1460058; 7413; 9072; 387592.

Cat
Felis sequences (NCBI entrez accession):
539716; 539715; 423193; 423192; 423191; 423190; 1364213; 1364212; 395407; 163827; 163823; 163825; 1169665; 232086; 1169666.

Latex
Hevea sequences:

(SEQ ID NO: 60)
Hey b 1
MAEDEDNQQGQGEGLKYLGFVQDAATYAVTTFSNVYLFAKDKSGPLQPG
VDIIEGPVKNVAVPLYNRFSYIPNGALKFVDSTVVASVTIIDRSLPPIV
KDASIQVVSAIRAAPEAARSLASSLPGQTKILAKVFYGEN (SEQ ID NO: 61)
Hey b 3
MAEEVEEERLKYLDFVRAAGVYAVDSFSTLYLYAKDISGPLKPGVDTIE
NVVKTVVTPVYYIPLEAVKFVDKTVDVSVTSLDGVVPPVIKQVSAQTYS
VAQDAPRIVLDVASSVFNTGVQEGAKALYANLEPKAEQYAVITWRALNK

```
LPLVPQVANVVVPTAVYFSEKYNDVVRGTTEQGYRVSSYLPLLPTEKIT

KVFGDEAS
```

Additional Hevea sequences (NCBI entrez accession):
3319923; 3319921; 3087805; 1493836; 1480457; 1223884; 3452147; 3451147; 1916805; 232267; 123335; 2501578; 3319662; 3288200; 1942537; 2392631; 2392630; 1421554; 1311006; 494093; 3183706; 3172534; 283243; 1170248; 1708278; 1706547; 464775; 266312; 231586; 123337; 116359; 123062; 2213877; 542013; 2144920; 1070656; 2129914; 2129913; 2129912; 100135; 82026; 1076559; 82028; 82027; 282933; 280399; 100138; 1086972; 108697; 1086976; 1086978; 1086978; 1086976; 1086974; 1086972; 913758; 913757; 913756; 234388; 1092500; 228691; 1177405; 18839; 18837; 18835; 18833; 18831; 1209317; 1184668; 168217; 168215; 168213; 168211; 168209; 348137.

Rye Grass

Lolium sequences:

```
                                            (SEQ ID NO: 62)
126385 Lol p 1
MASSSSVLLVVALFAVFLGSAHGIAKVPPGPNITAEYGDKWLDAKSTWY

GKPTGAGPKDNGGACGYKNVDKAPFNGMTGCGNTPIFKDGRGCGSCFEI

KCTKPESCSGEAVTVTITDDNEEPIAPYHFDLSGHAFGSMAKKGEEQNV

RSAGELELQFRRVKCKYPDDTKPTFHVEKASNPNYLAILVKYVDGDGDV

VAVDIKEKGKDKWIELKESWGAVWRIDTPDKLTGPFTVRYTTEGGTKSE

FEDVIPEGWKADTSYSAK
                                            (SEQ ID NO: 63)
126386 Lol p 2a
AAPVEFTVEKGSDEKNLALSIKYNKEGDSMAEVELKEHGSNEWLALKKN

GDGVWEIKSDKPLKGPFNFRFVSEKGMRNVFDDVVPADFKVGTTYKPE
                                            (SEQ ID NO: 64)
126387 Lol p 3
TKVDLTVEKGSDAKTLVLNIKYTRPGDTLAEVELRQHGSEEWEPMTKKG

NLWEVKSAKPLTGPMNFRFLSKGGMKNVFDEVIPTAFTVGKTYTPEYN
                                            (SEQ ID NO: 65)
2498581 Lol p 5a
MAVQKYTVALFLRRGPRGGPGRSYAADAGYTPAAAATPATPAATPAGGW

REGDDRRAEAAGGRQRLASRQPWPPLPTPLRRTSSRSSRPPSPSPPRAS

SPTSAAKAPGLIPKLDTAYDVAYKAAEAHPRGQVRRLRHCPHRSLRVIA

GALEVHAVKPATEEVLAAKIPTGELQIVDKIDAAFKIAATAANAAPTND

KFTVFESAFNKALNECTGGAMRPTSSSPPSRPRSSRPTPPPSPAAPEVK

YAVFEAALTKAITAMTQAQKAGKPAAAAATAAATVATAAATAAAVLPPP

LLVVQSLISLLIYY
                                            (SEQ ID NO: 66)
2498582 Lol p 5b
MAVQKHTVALFLAVALVAGPAASYAADAGYAPATPATPAAPATAATPAT

PATPATPAAVPSGKATTEEQKLIEKINAGFKAAVAAAAVVPPADKYKTF

VETFGTATNKAFVEGLASGYADQSKNQLTSKLDAALKLAYEAAQGATPE

AKYDAYVATLTEALRVIAGTLEVHAVKPAAEEVKVGAIPAAEVQLIDKV

DAAYRTAATAANAAPANDKFTVFENTFNNAIKVSLGAAYDSYKFIPTLV

AAVKQAYAAKQATAPEVKYTVSETALKKAVTAMSEAEKEATPAAAATAT

PTPAAATATPAAAYATATPAAATATATPAAATATPAAAGGYKV
                                            (SEQ ID NO: 67)
455288 Lol p isoform 9
MAVQKHTVALFLAVALVAGPAASYAADAGYAPATPATPAAPATAATPAT

PATPATPAAVPSGKATTEEQKLIEKINAGFKAAVAAAAVVPPADKYKTF

VETFGTATNKAFVEGLASGYADQSKNQLTSKLDAALKLAYEAAQGATPE

AKYDAYVATLTEALRVIAGTLEVHAVKPAAEEVKVGAIPAAEVQLIDKV

DAAYRTAATAANAAPANDKFTVFENTFNNAIKVSLGAAYDSYKFIPTLV

AAVKQAYAAKQATAPEVKYTVSETALKKAVTAMSEAEKEATPAAAATAT

PTPAAATATPAAAYATATPAAATATATPAAATATPAAAGGYKV
                                            (SEQ ID NO: 68)
1582249 Lol p 11
DKGPGFVVTGRVYCDPCRAGFETNVSHNVEGATVAVDCRPFDGGESKLK

AEATTDKDGWYKIEIDQDHQEEICEVVLAKSPDKSCSEIEEFRDRARVP

LTSNXGIKQQGIRYANPIAFFRKEPLKECGGILQAY
```

Additional Lolium sequences (NCBI entrez accession):
135480; 417103; 687261; 687259; 1771355; 2388662; 631955; 542131; 542130; 542129; 100636; 626029; 542132; 320616; 320615; 320614; 100638; 100634; 82450; 626028; 100639; 283345; 542133; 1771353; 1763163; 310877; 310875; 250525; 55317; 515377; 510911; 939932; 439950; 2718; 168316; 168314; 485371; 2388664; 2832717; 2828273; 548867.

Olive Tree

Olive Sequences

```
                                            (SEQ ID NO: 69)
416610 Ole e 1
EDIPQPPVSQFHIQGQVYCDTCRAGFITELSEFIPGASLRLQCKDKENG

DVTFTEVGYTRAEGLYSMLVERDHKNEFCEITLISSGRKDCNEIPTEGW

AKPSLKFKLNTVNGTTRTVNPLGFFKKEALPKCAQVYNKLGMYPPNM
```

Parietaria

Parietaria Sequences:

```
                                            (SEQ ID NO: 70)
2497750 Par j P2
MRTVSMAALVVIAAALAWTSSAEPAPAPAPGEEACGKVVQDIMPCLHFV

KGEEKEPSKECCSGTKKLSEEVKTTEQKREACKCIVRATKGISGIKNEL

VAEVPKKCDIKTTLPPITADFDCSKIQSTIFRGYY
                                            (SEQ ID NO: 71)
1352506 Par j P5
MVRALMPCLPFVQGKEKEPSKGCCSGAKRLDGETKTGPQRVHACECIQT

AMKTYSDIDGKLVSEVPKHCGIVDSKLPPIDVNMDCKTVGVVPRQPQLP

VSLRHGPVTGPSDPAHKARLERPQIRVPPPAPEKA
                                            (SEQ ID NO: 72)
1532056 Par j P8
MRTVSMAALVVIAAALAWTSSAELASAPAPGEGPCGKVVHHIMPCLKFV

KGEEKEPSKSCCSGTKKLSEEVKTTEQKREACKCIVAATKGISGIKNEL

VAEVPKKCGITTTLPPITADFDCSKIESTIFRGYY
```

(SEQ ID NO: 73)
1532058 Par j P9
MRTVSAPSAVALVVIVAAGLAWTSLASVAPPAPAPGSEETCGTVVRALM

PCLPFVQGKEKEPSKGCCSGAKRLDGETKTGLQRVHACECIQTAMKTYS

DIDGKLVSEVPKHCGIVDSKLPPIDVNMDCKTLGVVPRQPQLPVSLRHG

PVTGPSDPAHKARLERPQIRVPPPAPEKA (SEQ ID NO: 74)
2497749 Par j P9
MRTVSARSSVALVVIVAAVLVWTSSASVAPAPAPGSEETCGTVVGALMP

CLPFVQGKEKEPSKGCCSGAKRLDGETKTGPQRVHACECIQTAMKTYSD

IDGKLVSEVPKHCGIVDSKLPFIDVNMDCKTLGVLHYKGN (SEQ ID NO: 75)
1086003 Par j 1
MVRALMPCLPFVQGKEKEPSKGCCSGAKRLDGETKTGPQRVHACECIQT

AMKTYSDIDGKLVSEVPKHCGIVDSKLPPIDVNMDCKTVGVVPRQPQLP

VSLRHGPVTGPSRSRPPTKHGWRDPRLEFRPPHRKKPNPAFSTLG

Additional Parietaria sequences (NCBI entrez accession): 543659; 1836011; 1836010; 1311513; 1311512; 1311511; 1311510; 1311509; 240971.

Timothy Grass
Phleum Sequences:

(SEQ ID NO: 76)
Phl p 1
MASSSSVLLVVVLFAVFLGSAYGIPKVPPGPNITATYGDKWLDAKSTWY

GKPTGAGPKDNGGACYKDVDKPPFSGMTGCGNTPIFKSGRGCGSCFEI

KCTKPEACSGEPVVVHITDDNEEPIAPYHFDLSGHAFGAMAKKGDEQKL

RSAGELELQFRRVKCKYPEGTKVTFHVEKGSNPNYLALLVKYVNGDGDV

VAVDIKEKGKDKWIELKESWGAIWRIDTPDKLTGPFTVRYTTEGGTKTE

AEDVIPEGWKADTSYESK (SEQ ID NO: 77)
Phl p 1
MASSSSVLLVVALFAVFLGSAHGIPKVPPGPNITATYGDKWLDAKSTWY

GKPTAAGPKDNGGACYKDVDKPPFSGMTGCGNTPIFKSGRGCGSCFEI

KCTKPEACSGEPVVVHITDDNEEPIAAYHFDLSGIAFGSMAKKGDEQKL

RSAGEVEIQFRRVKCKYPEGTKVTFHVEKGSNPNYLALLVKFSGDGDVV

AVDIKEKGKDKWIALKESWGAIWRIDTPEVLKGPFTVRYTTEGGTKARA

KDVIPEGWKADTAYESK (SEQ ID NO: 78)
Phlp 2
MSMASSSSSSLLAMAVLAALFAGAWCVPKVTFTVEKGSNEKHLAVLVKY

EGDTMAEVELREHGSDEWVAMTKGEGGVWTFDSEEPLQGPFNFRFLTEK

GMKNVFDDVVPEKYTIGATYAPEE (SEQ ID NO: 79)
Phl p 5
ADLGYGGPATPAAPAEAAPAGKATTEEQKLIEKINDGFKAALAAAAGVP

PADKYKTEVATFGAASNKAFAEGLSAEPKGAAESSSKAALTSKLDAAYK

LAYKTAEGATPEAKYDAYVATLSEALRIIAGTLEVHAVKPAAEEVKVIP

AGELQVIEKVDSAFKVAATAANAAPANDKFTVFEAAFNNAIKASTGGAY

ESYKFIPALEAAVKQAYAATVATAPEVKYTVFETALKKAFTAMSEAQKA

AKPATEATATATAAVGAATGAATAATGGYKV (SEQ ID NO: 80)
Phl p 5
ADLGYGGPATPAAPAEAAPAGKATTEEQKLIEKINDGFKAALAAAAGVP

PADKYKTFVATFGAASNKAFAEGLSAEPKGAAESSSKAALTSKLDAAYK

LAYKTAEGATPEAKYDAYVATLSEALRIIAGTLEVHAVKPAAEEVKVIP

AGELQVIEKVDSAFKVAATAANAAPANDKFTVFEAAFNNAIKASTGGAY

ESYKFIPALEAAVKQAYAATVATAPEVKYTVFETALKKAITAMSEAQKA

AKPATEATATATAAVGAATGAATAATGGYKV (SEQ ID NO: 81)
Phl p 5b
AAAAVPRRGPRGGPGRSYTADAGYAPATPAAAGAAAGKATTEEQKLIED

INVGFKAAVAAAASVPAADKFKTFEAAFTSSSKAAAAKAPGLVPKLDAA

YSVAYKAAVGATPEAKFDSEVASLTEALRVIAGALEVHAVKPVTEEPGM

AKIPAGELQIIDKIDAAFKVAATAAATAPADDKFTVFEAAFNKAIKBST

GGAYDTYKCIPSLEAAVKQAYAATVAAAPQVKYAVFEAALTKAITAMSE

VQKVSQPATGAATVAAGAATTAAGAASGAATVAAGGYKV (SEQ ID NO: 82)
Phl p 5a
ADLGYGPATPAAPAAGYTPATPAAPAGADAAGKATTEEQKLIEKINAGF

KAALAGAGVQPADKYRTFVATFGPASNKAFAEGLSGEPKGAAESSSKAA

LTSKLDAAYKLAYKTAEGATPEAKYDAYVATLSEALRIIAGTLEVHAVK

PAAEEVKVIPAGELQVIEKVDAAFKVAATAANAAPANDKFTVFEAAFND

EIKASTGGAYESYKFIPALEAAVKQAYAATVATAPEVKYTVFETALKKA

ITAMSEAQKAAKPAAAATATATAAVGAATGAATAATGGYKV (SEQ ID NO: 83)
Phl p 5
MAVQKYTVALFLAVALVAGPAASYAADAGYAPATPAAAGAEAGKATTEE

QKLIEDINVGFKAAVAAAASVPAADKPKTFEAAFTSSSKAATAKAPGLV

PKLDAAYSVSYKAAVGATPEAKFDSFVASLTEALRVIAGALEVHAVKPV

TEEPGMAKIPAGELQIIDKIDAAFKVAATAAATAPADTVFEAAFNKAIK

ESTGGAYDTYKCIPSLEAAVKQAYAATVAAAPQVKYAVFEAALTKAITA

MSEVQKVSQPATGAATVAAGAATTAAGAASGAATVAAGGYKV (SEQ ID NO: 84)
Phl p 5
MAVQKYTVALFLAVALVAGPAASYAADAGYAPATPAAAGAEAGKATTEE

QKLIEDINVGFKAAVAAAASVPAADKFKTFEAAFTSSSKAATAKAPGLV

PKLDAAYSVAYKAAVGATPEAKFDSFVASLTEALRVIAGALEVHAVKPV

TEDPAWPKIPAGELQIIDKIDAAFKVAATAAATAPADDKFTVFEAAFNK

AIKESTGGAYDTYKCIPSLEAAVKQAYAATVAAAPQVKYAVFEAALTKA

ITAMSEVQKVSQPATGAATVAAGAATTATGAASGAATVAAGGYKV (SEQ ID NO: 85)
Phl p 5
ADAGYAPATPAAAGAEAGKATTEEQKLIEDINVGFKAAVAAAASVPAAD

KFKTFEAAFTSSSKAATAKAPGLVPKLDAAYSVAYKAAVGATPEAKFDS

```
                                   -continued
FVASLTEALRVIAGALEVHAVKPVTEEPGMAKIPAGELQIIDKIDAAFK

VAATAAATAPADDKFTVFEAAAFNKAIKESTGGAYDTYKCIPSLEAAVKQ

AYAATVAAAPQVKYAVFEAALTKATTAMSEVQKVSQPATGAATVAAGAA

TTAAGAASGAATVAAGGYKV (SEQ ID NO: 86)
Phl p 5
SVKRSNGSAEVHRGAVPRRGPRGGPGRSYAADAGYAPATPAAAGAEAGK

ATTEEQKLIEDINVGFKAAVAAAASVPAADKFKTFEAAFTSSSKAATAK

APGLVPKLDAAYSVAYKAAVGATPEAKFDSFVASLTEALRVIAGALEVH

AVKPVTEEPGMAKIPAGELQIIDKIDAAFKVAATAAATAPADDKFTVFE

AAFNKAIKESTGGAYDTYKCIPSLEAAVKQAYAATVAAAPQVKYAVFEA

ALTKAITAMSEVQKVSQPATGAATVAAGAATTAAGAASGAATVAAGGYK

V (SEQ ID NO: 87)
Phl p 5
MAVHQYTVALFLAVALVAGPAGSYAADLGYGPATPAAPAAGYTPATPAA

PAGAEPAGKATTEEQKLIEKINAGFKAALAAAAGVPPADKYRTFVATFG

AASNKAFAEGLSGEPKGAAESSSKAALTSKLDAAYKLAYKTAEGATPEA

KYDAYVATVSEALRIIAGTLEVHAVKPAAEEVKVIPAGELQVIEKVDAA

FKVAATAANAAPANDKFTVFEAAFNDAIKASTGGAYESYKFIPALEAAV

KQAYAATVATAPEVKYTVFETALKKAITAMSEAQKAAKPAAAATATATA

AVGAATGAATAATGGYKV (SEQ ID NO: 88)
Phl p 5
ADLGYGGPATPAAPAEAAPAGKATTEEQKLIEKINDGFKAALAAAAGVP

PADKYKTFVATFGAASNKAFAEGLSAEPKGAAESSSKAALTSKLDAAYK

LAYKTAEGATPEAKYDAYVATLSEALRIIAGTLEVHAVKPAAEEVKVIP

AGELQVIEKVDSAFKVAATAANAAPANDKFTVFEAAFNNAIKASTGGAY

ESYKFIPALEAAVKQAYAATVATAPEVKYTVFETALKKAFTAMSEAQKA

AKPATEATATATAAVGAATGAATAATGGYKV (SEQ ID NO: 89)
Phl p5b
AAAAVPRRGPRGGPGRSYTADAGYAPATPAAAGAAAGKATTEEQKLIED

INVGFKAAVAAAASVPAADKFKTFEAAFTSSSKAAAAKAPGLVPKLDAA

YSVAYKAAVGATPEAKFDSFVASLTEALRVIAGALEVHAVKPVTEEPGM

AKIPAGELQIIDKIDAAFKVAATAAATAPADDKFTVFEAAFNKAIKEST

GGAYDTYKCIPSLEAAVKQAYAATVAAAPQVKYAVFEAALTKAITAMSE

VQKVSQPATGAATVAAGAATTAAGAASGAATVAAGGYKV (SEQ ID NO: 90)
Phl p5a
ADLGYGPATPAAPAAGYTPATPAAPAGADAAGKATTEEQKLIEKINAGF

KAALAGAGVQPADKYRTFVATFGPASNKAFAEGLSGEPKGAAESSSKAA

LTSKLDAAYKLAYKTAEGATPEAKYDAYVATLSEALRIIAGTLEVHAVK

PAAEEVKVIPAGELQVIEKVDAAFKVAATAANAAPANDKFTVFEAAFND

EIKASTGGAYESYKFIPALEAAVKQAYAATVATAPEVKYTVFETALKKA

ITAMSEAQKAAKPAAAATATATAAVGAATGAATAATGGYKV (SEQ ID NO: 91)
Phl p 5
AVPRRGPRGGPGRSYAADAGYAPATPAAAGAEAGKATTEEQKLIEDINV

GFKAAVAAAASVPAGDKFKTFEAAFTSSSKAATAKAPGLVPKLDAAYSV

AYKAAVGATPEAKFDSFVASLTEALRVIAGALEVHAVKPVTEEPGMAKI

PAGELQIIDKIDAAFKVAATAAATAPADDKFTVFEAAFNKAIKESTGGA

YDTYKCIPSLEAAVKQAYAATVAAAPQVKYAVFEAALTKAITAMSEVQK

VSQPATGAATVAAGAATTATGAASGAATVAAGGYKV (SEQ ID NO: 92)
Phl p 5b
MAVPRRGPRGGPGRSYTADAGYAPATPAAAGAAAGKATTEEQKLIEDIN

VGFKAAVAARQRPAADKFKTFEAASPRHPRPLRQGAGLVPKLDAAYSVA

YKAAVGATPEAKFDSFVASLTEALRVIAGALEVHAVKPVTEEPGMAKIP

AGELQIIDKIDAAFKVAATAAATAPADDKFTVFEAAFNKAIKESTGGAY

DTYKCIPSLEAAVKQAYAATVAAAEVKYAVFEAALTKAITAMSEVQKV

SQPATGAATVAAGAATTAAGAASGAATVAAGGYKV (SEQ ID NO: 93)
Phl p 5
MAVHQYTVALFLAVALVAGPAASYAADLGYGPATPAAPAAGYTPATPAA

PAEAAPAGKATTEEQKLIEKINAGFKAALAAAAGVQPADKYRTFVATFG

AASNKAFAEGLSGEPKGAAESSSKAALTSKLDAAYKLAYKTAEGATPEA

KYDAYVATLSEALRIIAGTLEVHAVKPAAEEVKVIPAGELQVIEKVDAA

FKVAATAANAAPANDKFTVFEAAFNDAIKASTGGAYESYKFIPALEAAV

KQAYAATVATAPEVKYTVFETALKKAITAMSEAQKAAKPAAAATATATA

AVGAATGAATAATGGYKV (SEQ ID NO: 94)
Phl p 5
EAPAGKATTEEQKLIEKINAGFKAALARRLQPADKYRTFVATFGPASNK

AFAEGLSGEPKGAAESSSKAALTSKLDAAYKLAYKTAEGATPEAKYDAY

VATLSEALRIIAGTLEVHAVKPAAEEVKVIPAAELQVIEKVDAAFKVAA

TAANAAPANDKFTVFEAAFNDELKASTGGAYESYKFIPALEAAVKQAYA

ATVATAPEVKYTVFETALKKAITAMSEAQKAAKPPPLPPPPQPPPLAAT

GAATAATGGYKV (SEQ ID NO: 95)
Phl p 5
MAVHQYTVALFLAVALVAGPAASYAADLGYGPATPAAPAAGYTPATPAA

PAEAAPAGKATTEEQKLIEKINAGFKAALAAAAGVQPADKYRTFVATFG

AASNKAPAEGLSGEPKGAAESSSKAALTSKLDAAYKLAYKTAEGATPEA

KYDAYVATLSEALRIIAGTLEVHAVKPAAEEVKVIPAGELQVIEKVDAA

FKVAATAANAAPANDKFTVFEAAFNDAIKASTGGAYESYKFIPALEAAV

KQAYAATVATAPEVKYTVFETALKKAITAMSEAQKAAKPAAAATATATA

AVGAATGAATAATGGYKV (SEQ ID NO: 96)
Phl p 5b
MAVPRRGPRGGPGRSYTADAGYAPATPAAAGAAAGKATTEEQKLIEDIN

VGFKAAVAARQRPAADKFKTFEAASPRHPRPLRQGAGLVPKLDAAYSVA
```

-continued
```
YKAAVGATPEAKFDSFVASLTEALRVIAGALEVHAVKPVTEEPGMAKIP

AGELQIIDKIDAAFKVAATAAATAPADDKFTVFEAAFNKAIKESTGGAY

DTYKCIPSLEAAVKQAYAATVAAAAEVKYAVFEAALTKAITAMSEVQKV

SQPATGAATVAAGAATTAAGAASGAATVAAGGYKV
```

(SEQ ID NO: 97)
Phl p 5a
```
ADLGYGPATPAAPAAGYTPATPAAPAGADAAGKATTEEQKLIEKINAGF

KAALAGAGVQPADKYRTFVATFGPASNKAFAEGLSGEPKGAAESSSKAA

LTSKLDAAYKLAYKTAEGATPEAKYDAYVATLSEALRIIAGTLEVHAVK

PAAEEVKVIPAGELQVIEKVDAAFKVAATAANAAPANDKFTVFEAAFND

EIKASTGGAYESYKFIPALEAAVKQAYAATVATAPEVKYTVFETALKKA

ITAMSEAQKAAKPPPLPPPPQPPPLAATGAATAATGGYKV
```

(SEQ ID NO: 98)
Phl p 5
```
MAVHQYTVALFLAVALVAGPAASYAADLGYGPATPAAPAAGYTPATPAA

PAEAAPAGKATTEEQKLIEKINAGFKAALAAAAGVQPADKYRTFVATFG

AASNKAFAEGLSGEPKGAAESSSKAALTSKLDAAYKLAYKTAEGATPEA

KYDAYVATLSEALRIIAGTLEVHAVKPAAEEVKVIPAGELQVIEKVDAA

FKVAATAANAAPANDKFTVFEAAFNDAIKASTGGAYESYKFIPALEAAV

KQAYAATVATAPEVKYTVFETALKKAITAMSEAQKAAKPAAAATATATA

AVGAATGAATAATGGYKV
```

(SEQ ID NO: 99)
Phl p 6
```
MAAHKFMVAMFLAVAVVLGLATSPTAEGGKATTEEQKLIEDVNASFRAA

MATTANVPPADKYKTFEAAFTVSSKRNLADAVSKAPQLVPKLDEVYNAA

YNAADHAAPEDKYEAFVLHFSEALRIIAGTPEVHAVKPGA
```

(SEQ ID NO: 100)
Phl p 6
```
SKAPQLVPKLDEVYNAAYNAADHAAPEDKYEAFVLHFSEALHIIAGTPE

VHAVKPGA
```

(SEQ ID NO: 101)
Phl p 6
```
ADKYKTFEAAFTVSSKRNLADAVSKAPQLVPKLDEVYNAAYNAADHAAP

EDKYEAFVLHFSEALHIIAGTPEVHAVKPGA
```

(SEQ ID NO: 102)
Phl p 6
```
TEEQKLIEDVNASFRAAMATTANVPPADKYKTLEAAFTVSSKRNLADAV

SKAPQLVPKLDEVYNAAYNAADHAAPEDKYEAFVLHFSEALRIIAGTPE

VHAVKPGA
```

(SEQ ID NO: 103)
Phl p 6
```
MAAHKFMVAMFLAVAVVLGLATSPTAEGGKATTEEQKLIEDINASFRAA

MATTANVPPADKYKTFEAAFTVSSKRNLADAVSKAPQLVPKLDEVYNAA

YNAADHAAPEDKYEAFVLHFSEALHIIAGTPEVHAVKPGA
```

(SEQ ID NO: 104)
Phl p 6
```
MVAMFLAVAVVLGLATSPTAEGGKATTEEQKLIEDVNASFRAAMATTAN

VPPADKYKTFEAAFTVSSKRNLADAVSKAPQLVPKLDEVYNAAYNAADH

AAPEDKYEAFVLHFSEALRIIAGTPEVHAVKPGA
```

(SEQ ID NO: 105)
Phl p 7
```
MADDMERIFKRFDTNGDGKISLSELTDALRTLGSTSADEVQRMMAEIDT

DGDGFIDFNEFISFCNANPGLMKDVAKVF
```

(SEQ ID NO: 106)
Phl p 11
```
MSWQTYVDEHLMCEIEGHHLASAAILGHDGTVWAQSADFPQFKPEEITG

IMKDFDEPGHLAPTGMFVAGAKYMVIQGEPGRVIRGKKGAGGITIKKTG

QALVVGIYDEPMTPGQCNMVVERLGDYLVEQGM
```

Additional Phleum sequences (NCBI entrez accession): 458878; 548863; 2529314; 2529308; 2415702; 2415700; 2415698; 542168; 542167; 626037; 542169; 541814; 542171; 253337; 253336; 453976; 439960.

Wasp (and Related)
Vespula Sequences:

(SEQ ID NO: 107)
465054 ALLERGEN VES V 5
```
MEISGLVYLIIIVTIIDLPYGKANNYCKIKCLKGGVHTACKYGSLKPNC

GNKVVVSYGLTKQEKQDILKEHNDFRQKIARGLETRGNPGPQPPAKNMK

NLVWNDELAYVAQVWANQCQYGHDTCRDVAKYQVGQNVALTGSTAAKYD

DPVKLVKMWEDEVKDYNPKKKFSGNDFLKTGHYTQMVWANTKEVGCGSI

KYIQEKWHKHYLVCNYGPSGNFMNEELYQTK
```

(SEQ ID NO: 108)
1709545 ALLERGEN VES M 1
```
GPKCPFNSDTVSIIIETRENRNRDLYTLQTLQNHPEFKKKTITRPVVFI

THGFTSSASEKNFINLAKALVDKDNYMVISIDWQTAACTNEYPGLKYAY

YPTAASNTRLVGQYIATITQKLVKDYKISMANIRLIGHSLGAHVSGFAG

KRVQELKLGKYSEIIGLDPARPSFDSNHCSERLCETDAEYVQIIHTSNY

LGTEKLGTVDFYMNNGKNNPGCGRFFSEVCSHTRAVTYMAECIKHECCL

IGIPRSKSSQPISRCTKQECVCVGLNAKKYPSRGSFYVPVESTAPFCNN

KGKII
```

(SEQ ID NO: 109)
1352699 ALLERGEN VES V 1
```
MEENMNLKYLLLFVYFVQVLNCCYGHGDPLSYELDRGPKCPFNSDTVSI

IIETRENRNRDLYTLQTLQNHPEFKKKTITRPVVFITHGFTSSASETNF

INLAKALVDKDNYMVISIDWQTAACTNEAAGLKYLYYPTAARNTRLVGQ

YIATITQKLVKHYKISMANIRLIGHSLGAHASGFAGKKVQELKLGKYSE

IIGLDPARPSFDSNHCSERLCETDAEYVQIIHTSNYLGTEKTLGTVDFY

MNNGKNQPGCGRFFSEVCSHSRAVIYMAECIKHECCLIGIPKSKSSQPI

SSCTKQECVCVGLNAKKYPSRGSFYVPVESTAPFCNNKGKII
```

(SEQ ID NO: 110)
1346323 ALLERGEN VES V 2
```
SERPKRVFNIYVNVPTFMCHQYDLYFDEVTNFNIKRNSKDDFQGDKIAI

FYDPGEFPALLSLKDGKYKKRNGGVPQEGNITIHLQKFIENLDKIYPNR

NFSGIGVIDFERWRPIFRQNWGNMKIHKNFSIDLVRNEHPTWNKKMIEL

EASKRFEKYARFFMEETLKLAKKTRKQADWGYYGYPYCFNMSPNNLVPE

CDVTAMHENDKMSWLFNNQNVLLPSVYVRQELTPDQRIGLVQGRVKEAV
```

-continued
RISNNLKHSPKVLSYWWYVYQDETNTFLTETDVKKTFQEIVINGGDGII

IWGSSSDVNSLSKCKRLQDYLLTVLGPIAINVTEAVN (SEQ ID NO: 111)
549194 ALLERGEN VES VI
5KVNYCKIKCLKGGVHTACKYGTSTKPNCGKMVVKAYGLTEAEKQEILK

VHNDFRQKVAKGLETRGNPGPQPPAKNMNNLVWNDELANIAQVWASQCN

YGHDTCKDTEKYPVGQNIAKRSTTAALFDSPGKLVKMWENEVKDFNPNI

EWSKNNLKKTGHYTQMVWAKTKEIGCGSVKYVKDEWYTHYLVCNYGPSG

NFRNEKLYEKK

Additional vespula sequences (NCBI entrez accession):
549193; 549192; 549191; 549190; 549131; 117414; 126761; 69576; 625255; 627131; 627188; 627187; 482382; 112561; 627186; 627185; 1923233; 317645; 317647; 745570; 225764; 162551.

Tree allergen sequences (mainly birch) sequences:

(SEQ ID NO: 112)
114922 Bet v 1
MGVFNYETETTSVIPAARLFKAFILDGDNLFPKVAPQAISSVENIEGNG

GPGTIKKISFPEGFPFKYVKDRVDEVDHTNFKYNYSVIEGGPIGDTLEK

ISNEIKIVATPDGGSILKISNKYHTKGDHEVKAEQVKASKEMGETLLRA

VESYLLAHSDAYN (SEQ ID NO: 113)
130975 Bet v 2
MSWQTYVDEHLMCDIDGQASNSLASAIVGHDGSVWAQSSSFPQFKPQEI

TGIMKDFEEPGHLAPTGLHLGGIKYMVIQGEAGAVIRGKKGSGGITIKK

TGQALVFGIYEEPVTPGQCNMVVERLGDYLFDQGL (SEQ ID NO: 114)
1168696 Bet v 3
MPCSTEAMEKAGHGHASTPRKRSLSNSSFRLRSESLNTLRLRRIFDLFD

KNSDGIITVDELSRALNLLGLETDLSELESTVKSFTREGNIGLQFEDFI

SLHQSLNDSYFAYGGEDEDDNEEDMRKSILSQEEADSFGGFKVFDEDGD

GYISARELQMVLGKLGESEGSEIDRVEKMIVSVDSNRDGRVDFFEFKDM

MRSVLVRSS (SEQ ID NO: 115)
809536 Bet v 4
MADDHPQDKAERERIFKRFDANGDGKISAAELGEALKTLGSITPDEVKH

MMAEIDTDGDGFISFQEFTDFGRANRGLLKDVAKIF (SEQ ID NO: 116)
543675 Que a I - Quercus alba = oak trees
(fragment)
GVFTXESQETSVIAPAXLFKALFL (SEQ ID NO: 117)
543509 Car b I - Carpinus betulus = hornbeam
trees (fragment)
GVFNYEAETPSVIPAARLFKSYVLDGDKLIPKVAPQAIXK (SEQ ID NO: 118)
543491 Aln g I - Alnus glutinosa = alder trees
(fragment)
GVFNYEAETPSVIPAARLFKAFILDGDKLLPKVAPEAVSSVENI (SEQ ID NO: 119)
1204056 Rubisco
VQCMQVWPPLGLKKFETLSYLPPLSSEQLAKEVDYLLRKNLIPCLEFEL -continued
EHGFVYREHNRSPGYYDGRYWTMWKLPMFGCNDSSQVLKELEECKKAYP

SAFIRIIGFDDK

Additional tree allergen sequences (NCBI entrez accession number):
131919; 128193; 585564; 1942360; 2554672; 2392209; 2414158; 1321728; 1321726; 1321724; 1321722; 1321720; 1321718; 1321716; 1321714; 1321712; 3015520; 2935416; 464576; 1705843; 1168701; 1168710; 1168709; 1168708; 1168707; 1168706; 1168705; 1168704; 1168703; 1168702; 1842188; 2564228; 2564226; 2564224; 2564222; 2564220; 2051993; 1813311; 1536831; 534910; 534900; 534318; 1340000; 1339998; 2149808; 66207; 2129477; 1076249; 1076247; 629480; 481805; 81443; 1361968; 1361967; 1361966; 1361965; 1361964; 1361963; 1361962; 1361961; 1361960; 1361959; 320546; 629483; 629482; 629481; 541804; 320545; 81444; 541814; 629484; 474911; 452742; 1834387; 298737; 298736; 1584322; 1584321; 584320; 1542873; 1542871; 1542869; 1542867; 1542865; 1542863; 1542861; 1542859; 1542857; 1483232; 1483230; 1483228; 558561; 551640; 488605; 452746; 452744; 452740; 452738; 452736; 452734; 452732; 452730; 452728; 450885; 17938; 17927; 17925; 17921; 297538; 510951; 231331; 231329; 166953.

Peanut
Peanut Sequences (SEQ ID NO: 120)
1168391 Ara h 1
MRGRVSPLMLLLGILVLASVSATHAKSSPYQKKTENPCAQRCLQSCQQE

PDDLKQKACESRCTKLEYDPRCVYDPRGHTGTTNQRSPPGERTRGRQPG

DYDDDRRQPRREEGGRWGPAGPRERERREEDWRQPREDWRRPSHQQPRKI

RPEGREGEQEWGTPGSHVREETSRNNPFYFPSRRFSTRYGNQNGRIRVL

QRFDQRSRQFQNLQNHRIVQIEAKPNTLVLPKHADADNILVIQQGQATV

TVANGNNRKSFNLDEGHALRIPSGFISYILNRHDNQNLRVAKISMPVNT

PGQFEDFFPASSRDQSSYLQGFSRNTLEAAFNAEFNEIRRVLLEENAGG

EQEERGQRRWSTRSSENNEGVIVKVSKEHVEELTKHAKSVSKKGSEEEG

DITNPINLREGEPDLSNNFGKLFEVKPDKKNPQLQDLDMMLTCVEIKEG

ALMLPHFNSKAMVIVVVNKGTGNLELVAVRKEQQQRGRREEEEDEDEEE

EGSNREVRRYTARLKEGDVFIMPAAHPVAINASSELHLLGFGINAENNH

RIFLAGDKDNVIDQIEKQAKDLAFPGSGEQVEKLIKNQKESHFVSARPQ

SQSQSPSSPEKESPEKEDQEEENQGGKGPLLSILKAFN

Ragweed
Ambrosia Sequences (SEQ ID NO: 121)
113478 Amb a 1
MGIKHCCYILYFTLALVTLLQPVRSAEDLQQILPSANETRSLTTCGTYN

IIDGCWRGKADWAENRKALADCAQGFAKGTIGGKDGDIYTVTSELDDDV

ANPKEGTLRFGAAQNRPLWIIFARDMVIRLDRELAINNDKTIDGRGAKV

EIINAGFAIYNVKNIIHNIIMHDIVVNPGGLIKSHDGPPVPRKGSDGD

AIGISGGSQIWIDHCSLSKAVDGLIDAKHGSTHFTVSNCLFTQHQYLLL

FWDFDERGMLCTVAFNKFTDNVDQRMPNLRHGFVQVVNNNYERWGSYAL

-continued

GGSAGPTILSQGNRFLASDIKKEVVGRYGESAMSESINTWNWRSYMDVF

ENGAIFVPSGVDPVLTPEQNAGMIPAEPGEAVLRLTSSAGVLSCQPGAP

C (SEQ ID NO: 122)
113479 Amb a 2
MGIKHCCYILYFTLALVTLVQAGRLGEEVDILPSPNDTRRSLQGCEAHN

IIDKCWRCKPDWAENRQALGNCAQGFGKATHGGKWGDIYMVTSDQDDDV

VNPKEGTLRFGATQDRPLWIIFQRDMIIYLQQEMVVTSDKTIDGRGAKV

ELVYGGITLMNVKNVIIHNNIDIHDVRVLPGGRIKSNGGPAIPRHQSDG

DAIHVTGSSDIWIDHCTLSKSFDGLVDVNWGSTGVTISNCKFTHHEKAV

LLGASDTHFQDLKMHVTLAYNIFTNTVHERMPRCRFGFFQIVNNFYDRW

DKYAIGGSSNPTILSQGNKFVAPDFIYKKNVCLRTGAQPEPEWMTWNWRT

QNDVLENGAIFVASGSDPVLTAEQNAGMMQAEPGDMVPQLTMNAGVLTC

SPGAPC (SEQ ID NO: 123)
113477 Amb a 1.3
MGIKQCCYILYFTLALVALLQPVRSAEGVGEILPSVNETRSLQACEALN

IIDKCWRGKADWENNRQALADCAQGFAKGTYGGKWGDVYTVTSNLDDDV

ANPKEGTLRFAAAQNRPLWIIFKNDMVINLNQELVVNSDKTIDGRGVKV

EIINGGLTLMNVKNIIIHNINIHDVKVLPGGMIKSNDGPPILRQASDGD

TINVAGSSQIWIDHCSLSKSFDGLVDVTLGSTHVTISNCKFTQQSKAIL

LGADDTHVQDKGMLATVAFNMFTDNVDQRMPRCRFGFFQVVNNNYDRWG

TYAIGGSSAPTILCQGNRFLAPDDQIKKNVLARTGTGAAESMAWNWRSD

KDLLENGAIFVTSGSDPVLTPVQSAGMIPAEPGEAAIKLTSSAGVFSCH

PGAPC (SEQ ID NO: 124)
113476 Amb a 1.2
MGIKHCCYILYFTLALVTLLQPVRSAEDVEEFLPSANETRRSLKACEAH

NIIDKCWRCKADWANNRQALADCAQGFAKGTYGGKHGDVYTVTSDKDDD

VANPKEGTLRFAAAQNRPLWIIFKRNMVIHLNQELVVNSDKTIDGRGVK

VNIVNAGLTLMNVKNIIIHNINIHDIKVCPGGMIKSNDGPPILRQQSDG

DAINVAGSSQIWIDHCSLSKASDGLLDITLGSSHVTVSNCKFTQHQFVL

LLGADDTHYQDKGMLATVAFNMFTDHVDQRMPRCRFGFFQVVNNNYDRW

GTYAIGGSSAPTILSQGNRFFAPDDIIKKNVLARTGTGNAESMSWNWRT

DRDLLENGAIFLPSGSDPVLTPEQKAGMIPAEPGEAVLRLTSSAGVLSC

HQGAPC (SEQ ID NO: 125)
113475 Amb a 1.1
MGIKHCCYILYFTLALVTLLQPVRSAEDLQEILPVNETRRLTTSGAYNI

IDGCWRGKADWAENRKALADCAQGFGKGTVGGKDGDIYTVTSELDDDVA

NPKEGTLRFAAQNRPLWIIFERDMVIRLDKEMVVNSDKTIDGRGAKVE

IINAGFTLNGVKNVIIHNINMHDVKVNPGGLIKSNDGPAAPRAGSDDA

ISISGSSQIWIDHCSLSKSVDGLVDAKLGTTRLTVSNSLFTQHQFVLLF

-continued

GAGDENIEDRGMLATVAFNTFTDNVDQRMPRCRHGFFQVVNNNYDKWGS

YAIGGSASPTILSQGNRFCAPDERSKKNVLGRHGEAAAESMKWNWRTNK

DVLENGAIFVASGVDPVLTPEQSAGMIPAEPGESALSLTSSAGVLSCQP

GAPC

Cedar Sequences (SEQ ID NO: 126)
493634 Cry j IB precursor
MDSPCLVALLVFSFVIGSCFSDNPIDSCWRGDSNWAQNRMKLADCAVGF

GSSTMGGKGGDLYTVTNSDDDPVNPPGTLRYGATRDRPLWIIFSGNMNI

KLKMPMYIAGYKTFDGRGAQVYIGNGGPCVFIKRVSNVIIHGLYLYGCS

TSVLGNVLINESFGVEPVHPQDGDALTLRTATNIWIDHNSFSNSSDGLV

DVTLTSTGVTISNNLFFNHHKVMSLGHDDAYSDDKSMKVTVAFNQFGPN

CGQRMPRARYGLVHVANNNYDPWTIYAIGGSSNPTILSEGNSFTAPNES

YKKQVTIRIGCKTSSSCSNWVWQSTQDVFYNGAYFVSSGKYEGGNIYTK

KEAFNVENGNATPHLTQNAGVLTCSLSKRC (SEQ ID NO: 127)
493632 Cry j IA precursor
MDSPCLVALLVLSFVIGSCFSDNPIDSCWRGDSNWAQNRMKLADCAVGF

GSSTMGGKGGDLYTVTNSDDDPVNPAPGTLRYGATRDRPLWIIFSGNMN

IKLKMPMYIAGYKTFDGRGAQVYIGNGGPCVFIKRVSNVIIHGLHLYGC

STSVLGNVLINESFGVEPVHPQDGDALTLRTATNIWIDHNSFSNSSDGL

VDVTLSSTGVTISNNLFFNHHKVMLLGHDDAYSDDKSMKVTVAFNQFGP

NCGQRMPRARYGLVHVANNNYDPWTIYAIGGSSNPTILSEGNSFTAPNE

SYKKQVTIRIGCKTSSSCSNWVWQSTQDVFYNGAYFVSSGKYEGGNIYT

KKEAFNVENGNATPQLTKNAGVLTCSLSKRC (SEQ ID NO: 128)
1076242 Cry j II precursor - Japanese cedar
MAMKLIAPMAFLAMQLIIMAAAEDQSAQIMLDSVVEKYLRSNRSLRKVE

HSRHDAINIFNVEKYGAVGDGKHDCTEAFSTAWQAACKNPSAMLLVPGS

KKFVVNNLFFNGPCQPHFTFKVDGIIAAYQNPASWKNNRIWLQFAKLTG

FTLMGKGVIDGQGKQWWAGQCKWVNGREICNDRDRPTAIKFDFSTGLII

QGLKLMNSPEFHLVFGNCEGVKIIGISITAPRDSPNTDGIDIFASKNFH

LQKNTIGTGDDCVAIGTGSSNIVIEDLICGPGHGISIGSLGRENSRAEV

SYVHVNGAKFIDTQNGLRIKTWQGGSGMASHIIYENVEMINSENPILIN

QFYCTSASACQNQRSAVQIQDVTYKNIRGTSATAAAIQLKCSDSMPCKD

IKLSDISLKLTSGKIASCLNDNANGYFSGHVIPACKNLSPSAKRKESKS

HKHPKTVMVENMRAYDKGNRTRILLGSRPPNCTNKCHGCSPCKAKLVIV

HRIMPQEYYPQRWICSCHGKIYHP (SEQ ID NO: 129)
1076241 Cry j II protein - Japanese cedar
MAMKFIAPMAFVAMQLIIMAAAEDQSAQIMLDSDIEQYLRSNRSLRKVE

HSRHDAINIFNVEKYGAVGDGKHDCTEAFSTAWQAACKKPSAMLLVPGN

KKFVVNNLFFNGPCQPHFTFKVDGIIAAYQNPASWKNNRIWLQFAKLTG

```
FTLMGKGVIDGQGKQWWAGQCKWVNGREICNDRDRPTAIKFDFSTGLII

QGLKLMNSPEFHLVFGNCEGVKIIGISITAPRDSPNTDGIDIFASKNFH

LQKNTIGTGDDCVAIGTGSSNIVIEDLICGPGHGISIGSLGRENSRAEV

SYVHVNGAKFIDTQNGLRIKTWQGGSMASHIIYENVEMINSENPILIN

QFYCTSASACQNQRSAVQIQDVTYKNIRGTSATAAAIQLKCSDSMPCKD

IKLSDISLKLTSGKIASCLNDNANGYFSGHVIPACKNLSPSAKRKESKS

HKHPKTVMVKNMGAYDKGNRTRILLGSRPPNCTNKCHGCSPCKAKLVIV

HRIMPQEYYPQRWMCSRHGKIYHP (SEQ ID NO: 130)
541803 Cry j I precursor - Japanese cedar
MDSPCLVALLVLSFVIGSCFSDNPIDSCWRGDSNWAQNRMKLADCAVGF

GSSTMGGKGGDLYTVTNSDDDPVNPPGTLRYGATRDRPLWILFSGNMNI

KLKMPMYIAGYKTFDGRGAQVYIGNGGPCVFIKRVSNVIIHGLHLYGCS

TSVLGNVLINESFGVEPVHPQDGDALTLRTATNIWIDHNSFSNSSDGLV

DVTLSSTGVTISNNLFFNHHHKVMLLGHDDAYSDDKSMKVTVAFNQFGPN

CGQRMPRARYGLVHVANNNYDPWTIYAIGGSSNPTILSEGNSFTAPNES

YKKQVTIRIGCKTSSSCSNWVWQSTQDVFYNGAYFVSSGKYEGGNIYTK

KEAFNVENGNATPQLTKNAGVLTCSLSKRC (SEQ ID NO: 131)
541802 Cry j I precursor- Japanese cedar
MDSPCLVALLVFSFVIGSCFSDNPIDSCWRGDSNWAQNRMKLADCAVGF

GSSTMGGKGGDLYTVTNSDDDPVNPAPGTLRYGATRDRPLWIIFSGNMN

IKLKMPMYIAGYKTFDGRGAQVYIGNGGPCVFIKRVSNVIIHGLYLYGC

STSVLGNVLINESFGVEPVHPQDGDALTLRTATNIWIDHNSFSNSSDGL

VDVTLTSTGVTISNNLFFNHHHKVMSLGHDDAYSDDKSMKVTVAFNQFGP

NCGQRMPRARYGLVHVANNNYDPWTIYAIGGSSNPTILSEGNSFTAPNE

SYKKQVTIRIGCKTSSSCSNWVWQSTQDVFYNGAYFVSSGKYEGGNIYT

KKEAFNVENGNATPHLTQNAGVLTCSLSKRC
```

Dog
Canis Sequences:

```
                                (SEQ ID NO: 132)
Can f 1
MKTLLLTIGFSLIAILQAQDTPALGKDTVAVSGKWYLKAMTADQEVPEK

PDSVTPMILKAQKGGNLEAKITMLTNGQCQNITVVLHKTSEPGKYTAYE

GQRVVFIQPSPVRDHYILYCEGELHGRQIRMAKLLGRDPEQSQEALEDF

REFSRAKGLNQEILELAQSETCSPGGQ (SEQ ID NO: 133)
Serum albumin fragment
EAYKSEIAHRYNDLGEEHFRGLVL (SEQ ID NO: 134)
Serum albumin fragment
LSSAKERFKCASLQKFGDRAFKAWSVARLSQRFPKADFAEISKVVTDLT

KVHKECCHGDLLECADDRADLAKYMCENQDSISTKLKECCDKPVLEKSQ

CLAEVERDELPGDLPSLAADFVEDKEVCKNYQEAKDVFLGTFLYEYSRR

HPEYSVSLLLRLAKEYEATLEKCCATDDPPTCYAKVLDEFKPLVDEPQN

LVKTNCELFEKLGEYGFQNALLVRYTKKAPQVSTPTLVVEVSRKLGKVG

TKCCKKPESERMSCADDFLS (SEQ ID NO: 135)
Can f 2
MQLLLLTVGLALICGLQAQEGNHEEPQGGLEELSGRWHSVALASNKSDL

IKPWGHFRVFIHSMSAKDGNLHGDILIPQDGQCEKVSLTAFKTATSNKF

DLEYWGHNDLYLAEVDPKSYLILYMINQYNDDTSLVAHLMVRDLSRQQD

FLPAFESVCEDIGLHKDQIVVLSDDDRCQGSRD
```

Additional dog allergen protein (NCBI entrez accession):
Horse
Equus Sequences:

```
                                (SEQ ID NO: 136)
1575778 Equ c1
MKLLLLCLGLILVCAQQEENSDVAIRNFDISKLSGEWYSIFLASDVKEK

IEENGSMRVFVDVIRALDNSSLYAEYQTKVNGECTEFPMVFDKTEEDGV

YSLNYDGYNVFRISEFENDEHIILYLVNFDKDRPFQLFEFYAREPDVSP

EIKEEFVKIVQKRGIVKENIIDLTKIDRCFQLRGNGVAQA (SEQ ID NO: 137)
3121755 Equ c 2
SQXPQSETDYSQLSGEWNTIYGAASNIXK
```

Euroglyphus (mite)
Euroglyphus Sequences:

```
                                (SEQ ID NO: 138)
Eur m 1 (variant)
TYACSINSVSLPSELDLRSLRTVTPIRMQGGCGSCWAFSGVASTESAYL

AYRNMSLDLAEQELVDCASQNGCHGDTIPRGTEYIQQNGVVQEHYYPYV

AREQSCHRPNAQRYGLKNYCQISPPDSNKIRQALTQTHTAVAVIIGIKD

LNAFRHYDGRTIMQHDNGYQPNYHAVNIVGYGNTQGVDYWIVRNSWDTT

WGDNGYGYFAANINL (SEQ ID NO: 139)
Eur m 1 (variant)
TYACSINSVSLPSELDLRSLRTVTFIRMQGGCGSCWAFSGVASTESAYL

AYRNMSLDLAEQELVDCASQNGCHGDTIPRGIEYIQQNGVVQEHYYPYV

AREQSCHRPNAQRYGLKNYCQISPPDSNKIRQALTQTHTAVAVIIGIKD

LNAFRHYDGRTIMQHDNGYQPNYHAVNIVGYGNTQGVDYWIVRNSWDTT

WGDNGYGYFAANINL (SEQ ID NO: 140)
Eur m 1 (variant)
ETNACSINGNAPAEIDLRQMRTVTPIRMQGGCGSCWAFSGVAATESAYL

AYRNQSLDLAEQELVDCASQHGCHGDTIPRGIEYIQHNGVVQESYYRYV

AREQSCRRPNAQRFGISNYCQIYPPNANKIREALAQTHSAIAVIIGIKD

LDAFRHYDGRTIIQRDNGYQPNYHAVNIVGYSNAQGVDYWIVRNSWDTN

WGDNGYGYFAANIDL (SEQ ID NO: 141)
Eur m 1 (variant)
ETSACRINSVNVPSELDLRSLRTVTPIRMQGGCGSCWAFSGVAATESAY

LAYRNTSLDLSEQELVDCASQHGCHGDTIPRGIEYIQQNGVVEERSYPY
```

-continued
```
VAREQQCRRPNSQHYGISNYCQIYPPDVKQIREALTQTHTAIAVIIGIK
DLRAFQHYDGRTIIQHDNGYQPNYHAVNIVGYGSTQGVDYWIVRNSWDT
TWGDSGYGYFQAGNNL
```

Poa (Grass) Sequences (SEQ ID NO: 142)
113562 POLLEN ALLERGEN POA P 9
```
MAVQKYTVALFLVALVVGPAASYAADLSYGAPATPAAPAAGYTPAAPAG
AAPKATTDEQKMIEKINVGFKAAVAAAGGVPAANKYKTFVATFGAASNK
AFAEALSTEPKGAAVDSSKAALTSKLDAAYKLAYKSAEGATPEAKYDDY
VATLSEALRIIAGTLEVHGVKPAAEEVKATPAGELQVIDKVDAAFKVAA
TAANAAPANDKFTVFEAAFNDAIKASTGGAYQSYKFIPALEAAVKQSYA
ATVATAPAVKYTVFETALKKAITAMSQAQKAAKPAAAATGTATAAVGAA
TGAATAAAGGYKV
```

(SEQ ID NO: 143)
113561 POA P 9
```
MAVHQYTVALFLAVALVAGPAASYAADVGYGAPATLATPATPAAPAAGY
TPAAPAGAAPKATTDEQKLIEKINAGFKAAVAAAAGVPAVDKYKTFVAT
FGTASNKAFAEALSTEPKGAAAASSNAVLTSKLDAAYKLAYKSAEGATP
EAKYDAYVATLSEALRIIAGTLEVHAVKPAGEEVKAIPAGELQVIDKVD
AAFKVAATAANAAPANDKFTVFEAAFNDAIKASTGGAYQSYKFIEALEA
AVKQSYAATVATAPAVKYTVFETALKKAITAMSQAQKAAKPAAAVTATA
TGAVGAATGAVGAATGAATAAAGGYKTGAATPTAGGYKV
```

(SEQ ID NO: 144)
113560 POA P 9
```
MDKANGAYKTALKAASAVAPAEKFPVFQATFDKNLKEGLSGPDAVGFAK
KLDAFIQTSYLSTKAAEPKEKFDLFVLSLTEVLRFMAGAVKAPPASKFP
AKPAPKVAAYTPAAPAGAAPKATTDEQKLIEKINVGFKAAVAAAAGVPA
ASKYKTFVATFGAASNKAFAEALSTEPKGAAVASSKAVLTSKLDAAYKL
AYKSAEGATPEAKYDAYVATLSEALRIIAGTLEVHGVKPAAEEVKAIPA
GELQVIDKVDAAFKVAATAANAAPANDKFTVFEAAFNDAIKASTGGAYQ
SYKFIPALEAAVKQSYAATVATAPAVKYTVFETALKKAITAMSQAQKAA
KPAAAVTGTATSAVGAATGAATAAAGGYKV
```

Cockroach Sequences (SEQ ID NO: 145)
2833325 Cr p1
```
MKTALVFAAVVAFVAARFPDHKDYKQLADKQFLAKQRDVLRLFBRVHQH
NILNDQVEVGIPMTSKQTSATTVPPSGEAVHGVLQEGHARPRGEPFSVN
YEKHREQAIMLYDLLYFANDYDTFYKTACWARDRVNEGMFMYSFSIAVF
HRDDMQGVMLPPPYEVYPYLFVDHDVIHMAQKYWMKNAGSGEHHSHVIP
VNFTLRTQDHLLAYFTSDVNLNAFNTYYRYYYPSWYNTTLYGHNIDRRG
EQFYYTYKQIYARYFLERLSNDLPDVYPFYYSKPVKSAYNPNLRYHNGE
EMPVRPSNMYVTNFDLYYIADIKNYEKRVEDAIDFGYAFDEHMKPHSLY
HDVHGMEYLADMILEGNMDSPNFYFYGSIYHMYHSMIGHIVDPYRKMGL
APSLEHPETVLRDPVFYQLWKRVDHLFQKYKNRLPRYTHDELAFEGVKV
ENVDVGKLYTYFEQYDMSLDMAVYVNNVDQISNVDVQLAVRLNHKPFTY
NIEVSSDKAQDVYVAVFLGPKYDYLGREYDLNDRRHYFVEMDRFPYHVG
AGKTVIERNSHDSNIIAPERDSYRTFYKKVQEAYEGKSQYYVDKGHNYC
GYPENLLIPKGKKGGQAYTFYVIVTPYVKQDEHDFEPYNYKAFSYCGVG
SERKYPDNKPLGYPFDRKIYSNDFYTPNMYFKDVIIFHKKYDEVGVQGH
```

(SEQ ID NO: 146)
2231297 Cr p2
```
INEIHSIIGLPPFVPPSRRHARRGVGINGLIDDVIAILPVDELKALFQE
KLETSPDFKALYDAIRSPEFQSIISTLNAMQRSEHHQNLRDKGVDVDHF
IQLIRALFGLSRAARNLQDDLNDFLHSLEPISPRHRGLPRQRRRSARV
SAYLHADDFHKIITTIEALPEFANFYNFLKEHGLDVVDYINEIHSIIGL
PPFVPPSRRHARRGVGINGLIDDVIAILPVDELKALFQEKLETSPDFKA
LYDAIRSPEFQSIISTLNAMPEYQELLQNLRDKGVDVDHFIRVDQGTLR
TLSSGQRNLQDDLNDFLALIPTDQILAIAMDYLANDAEVQELVAYLQSD
DFHKIITTIEALPEFANFYNFLKEHGLDVVDYINEIHSIIGLPPFVPPS
QRHARRGVGINGLIDDVIAILPVDELKALFQEKLETSPDFKALYDAIDL
RSSRA
```

(SEQ ID NO: 147)
1703445 Bla g 2
```
MIGLKLVTVLFAVATITHAAELQRVPLYKLVHVFINTQYAGITKIGNQN
FLTVFDSTSCNVVVASQECVGGACVCPNLQKYEKLKPKYISDGNVQVKF
FDTGSAVGRGIEDSLTISNLTTSQQDIVLADELSQEVCILSADVVVGIA
APGCPNALKGKTVLENFVEENLIAPVFSIHHARFQDGEHFGEIIFGGSD
WKYVDGEFTYVPLVGDDSWKFRLDGVKIGDTTVAPAGTQAIIDTSKAII
VGPKAYVNPINEAIGCVVEKTTTRRICKLDCSKIPSLPDVTFVINGRNF
NISSQYYIQQNGNLCYSGFQPCGHSDHFFIGDFFVDHYYSEFNWENKTM
GFGRSVESV
```

(SEQ ID NO: 148)
1705483 Bla g 4
```
AVLALCATDTLANEDCFRHESLVPNLDYERFRGSWIIAAGTSEALTQYK
CWIDRFSYDDALVSKYTDSQGKNRTTIRGRTKFEGNKFTIDYNDKGKAF
SAPYSVLATDYENYAIVEGCPAAANGHVIYVQIRFSVRRFHPKLGDKEM
IQHYTLDQVNQHKKAIEEDLKHFNLKYEDLHSTCH
```

(SEQ ID NO: 149)
2326190 Bla g 5
```
YKLTYCPVKALGEPIRFLLSYGEKDFEDYRFQEGDWPNLKPSMPFGKTP
VLEIDGKQTHQSVAISRYLGKQFGLSGKDDWENLEIDMIVDTISDFRAA
IANYHYDADENSKQKKWDPLKKETIPYYTKKFDEVVKANGGYLAAGKLT
WADFYFVAILDYLNHMAKEDLVANQPNLKALREKVLGLPAIKAWVAKRP
PTDL
```

Additional cockroach sequences (NCBI Entrez accession numbers):
2580504; 1580797; 1580794; 1362590; 544619; 544618; 1531531; 1580792; 1166573; 1176397; 2317849.

Allergen (General) Sequences:
NCBI Accession Numbers

2739154; 3719257; 3703107; 3687326; 3643813; 3087805; 1864024; 1493836; 1480457; 2593176; 2593174; 1575778; 763532; 746485; 163827; 163823; 3080761; 163825; 3608493; 3581965; 2253610; 2231297; 2317849; 3409499; 3409498; 3409497; 3409496; 3409495; 3409494; 3409493; 3409492; 3409491; 3409490; 3409431; 3409488; 3409487; 3409486; 3409485; 3409484; 3409483; 3409482; 3409481; 3409480; 3409479; 3409478; 3409477; 3409476; 3409475; 3409474; 3409473; 3409472; 3409471; 3409470; 3409469; 3409468; 3409467; 3409466; 3409465; 3409464; 3409463; 3409462; 3409461; 3409460; 3409459; 3409458; 3409457; 3409456; 3318885; 3396070; 3367732; 1916805; 3337403; 2851457; 2851456; 1351295; 549187; 136467; 1173367; 2499810; 2498582; 2498581; 1346478; 1171009; 126608; 114091; 2506771; 1706660; 1169665; 1169531; 232086; 416318; 114922; 2497701; 1703232; 1703233; 1703233; 1703232; 3287877; 3122132; 3182907; 3121758; 3121756; 3121755; 3121746; 3121745; 3319925; 3319923; 3319921; 3319651; 3318731; 3318779; 3309647; 3309047; 3309045; 3309043; 3309041; 3309039; 3288200; 3288068; 2924494; 3256212; 3256210; 3243234; 3210053; 3210052; 3210051; 3210050; 3210049; 3210048; 3210047; 3210046; 3210045; 3210044; 3210043; 3210042; 3210041; 3210040; 3210039; 3210038; 3210037; 3210036; 3210035; 3210034; 3210033; 3210032; 3210031; 3210030; 3210029; 3210028; 3210027; 3210026; 3210025; 3210024; 3210023; 3210022; 3210021; 3210020; 3210019; 3210018; 3210017; 3210016; 3210015; 3210014; 3210013; 3210012; 3210011; 3210010; 3210009; 3210008; 3210007; 3210006; 3210005; 3210004; 3210003; 3210002; 3210001; 3210000; 3209999; 3201547; 2781152; 2392605; 2392604; 2781014; 1942360; 2554672; 2392209; 3114481; 3114480; 2981657; 3183706; 3152922; 3135503; 3135501; 3135499; 3135497; 2414158; 1321733; 1321731; 1321728; 1321726; 1321724; 1321722; 1321720; 1321718; 1321716; 1321714; 1321712; 3095075; 3062795; 3062793; 3062791; 2266625; 2266623; 2182106; 3044216; 2154736; 3021324; 3004467; 3005841; 3005839; 3004485; 3004473; 3004471; 3004469; 3004465; 2440053; 1805730; 2970629; 2959318; 2935527; 2935416; 809536; 730091; 585279; 584968; 2498195; 2833325; 2498604; 2498317; 2498299; 2493414; 2498586; 2498585; 2498576; 2497749; 2493446; 2493445; 1513216; 729944; 2498099; 548449; 465054; 465053; 465052; 548671; 548670; 548660; 548658; 548657; 2832430; 232084; 2500822; 2498118; 2498119; 2498119; 2498118; 1708296; 1708793; 416607; 416608; 416608; 416607; 2499791; 2498580; 2498579; 2498578; 2498577; 2497750; 1705483; 1703445; 1709542; 1709545; 1710531; 1352699; 1346568; 1346323; 1346322; 2507248; 11352240; 1352239; 1352237; 1352229; 1351935; 1350779; 1346806; 1346804; 1346803; 1170095; 1168701; 1352506; 1171011; 1171008; 1171005; 1171004; 1171002; 1171001; 1168710; 1168709; 1168708; 1168707; 1168706; 1168705; 1168704; 1168703; 1168702; 1168696; 1168391; 1168390; 1168348; 1173075; 1173074; 1173071; 1169290; 1163170; 1168402; 729764; 729320; 729979; 729970; 729315; 730050; 730049; 730048; 549194; 549193; 549192; 549191; 549190; 549131; 549188; 549185; 549184; 549183; 549182; 549181; 549180; 549179; 464471; 585290; 416731; 1169666; 113478; 113479; 113477; 113476; 113475; 130975; 119656; 113562; 113561; 113560; 416610; 126387; 126386; 126385; 132270; 416611; 416612; 416612; 416611; 730035; 127205; 1352238; 125887; 549186; 137395; 730036; 133174; 114090; 131112; 126949; 129293; 124757; 129501; 416636; 2801531; 2796177; 2796175; 2677826; 2735118; 2735116; 2735114; 2735112; 2735110; 2735108; 2735106; 273531; 2735102; 2735100; 2735098; 2735096; 2707295; 2154730; 2154728; 1684720; 2580504; 2465137; 2465135; 2465133; 2465131; 2465129; 2465127; 2564228; 2564226; 2564224; 2564222; 2564220; 2051993; 1313972; 1313970; 1313968; 1313966; 2443824; 2488684; 2488683; 2488682; 2488681; 2488680; 2488679; 2488678; 2326190; 2464905; 2415702; 2415700; 2415698; 2398759; 2398757; 2353266; 2338288; 1167836; 414703; 2276458; 1684718; 2293571; 1580797; 1580794; 2245508; 2245060; 1261972; 2190552; 1881574; 511953; 1532058; 1532056; 1532054; 1359436; 666007; 487661; 217308; 1731859; 217306; 217304; 1545803; 1514943; 577696; 516728; 506858; 493634; 493632; 2154734; 2154732; 543659; 1086046; 1086045; 2147643; 2147642; 1086003; 1086002; 1086001; 543675; 543623; 543509; 543491; 1364099; 2147108; 2147107; 1364001; 1085628; 631913; 631912; 631911; 2147092; 477301; 543482; 345521; 542131; 542130; 542129; 100636; 2146809; 480443; 2114497; 2144915; 72355; 71728; 319828; 1082946; 1082945; 1082944; 539716; 539715; 423193; 423192; 423191; 423190; 1079187; 627190; 627131; 627188; 627187; 482382; 1362656; 627186; 627185; 627182; 482381; 85299; 85298; 2133756; 2133755; 1079186; 627181; 32314; 32313; 112559; 112558; 1362590; 2133564; 1085122; 1073171; 627144; 627143; 627142; 627141; 280576; 102835; 102834; 102833; 102832; 84703; 84702; 84700; 84699; 84698; 84696; 477888; 477505; 102575; 102572; 478272; 2130094; 629813; 629812; 542172; 542168; 542167; 481432; 320620; 280414; 626029; 542132; 320615; 320614; 100638; 100637; 100635; 82449; 320611; 320610; 280409; 320607; 320606; 539051; 539050; 539049; 539048; 322803; 280407; 100501; 100498; 100497; 100496; 1362137; 1362136; 1362135; 1362134; 1362133; 1362132; 1362131; 1362130; 1362129; 1362128; 100478; 2129311; 1076531; 1362049; 1076486; 2129817; 2129816; 2129815; 2129814; 2129813; 2129812; 2129805; 2129804; 2129802; 2129801; 2129800; 2129799; 479902; 479901; 2129477; 1076247; 629480; 1076242; 1076241; 541803; 541802; 280372; 280371; 1361968; 1361967; 1361966; 1361965; 1361964; 1361963; 1361962; 1361961; 1361960; 1361959; 320546; 2119763; 543622; 541804; 478825; 478824; 478823; 421788; 320545; 81444; 626037; 626028; 539056; 483123; 481398; 481397; 100733; 100732; 100639; 625532; 1083651; 322674; 322673; 81719; 81718; 2118430; 2118429; 2118428; 2118427; 419801; 419800; 419799; 419798; 282991; 100691; 322995; 322994; 101824; 626077; 414553; 398830; 1311457; 1916292; 1911819; 1911818; 1911659; 1911582; 467629; 467627; 467619; 467617; 915347; 1871507; 1322185; 1322183; 317645; 317647; 1850544; 1850542; 1850540; 283117; 452742; 1842045; 1839305; 1836011; 1836010; 1829900; 1829319; 1829318; 1829317; 1829316; 1829315; 1829314; 1825459; 1803187; 159653; 1773369; 1769849; 1769847; 608690; 310877; 310875; 1438761; 1311513; 1311512; 1311511; 1311510; 1311509; 1311631; 1246120; 1246119; 1246118; 1246117; 1246116; 1478293; 1478292; 1311642; 1174278; 1174276; 1086972; 1086974; 1086976; 1086978; 1086978; 1086976; 1086974; 1086972; 999009; 999356; 999355; 994866; 994865; 913758; 913757; 913756; 913285; 913283; 926885; 807138; 632782; 601807; 546852; 633938; 544619; 544618; 453094; 451275; 451274; 407610; 407609; 404371; 409328; 299551; 299550; 264742; 261407; 255657; 250902; 250525; 1613674; 1613673; 1613672; 1613671; 1613670; 1613304; 1613303; 1613302; 1613240; 1613239; 1613238; 1612181; 1612180; 1612179; 1612178; 1612177; 1612176; 1612175; 1612174; 1612173; 1612172; 1612171; 1612170; 1612169; 1612168; 1612167; 1612166; 1612165; 1612164; 1612163; 1612162; 1612161; 1612160; 1612159;

1612158; 1612157; 1612156; 1612155; 1612154; 1612153; 1612152; 1612151; 1612150; 1612149; 1612148; 1612147; 1612146; 1612145; 1612144; 1612143; 1612142; 1612141; 1612140; 1612139; 1093120; 447712; 447711; 447710; 1587177; 158542; 1582223; 1582222; 1531531; 1580792; 886215; 1545317; 1545315; 1545313; 1545311; 1545831; 1545887; 1545885; 1545883; 1545881; 1545879; 1545877; 1545875; 166486; 1498496; 1460058; 972513; 1009442; 1009440; 1009438; 1009436; 1009434; 7413; 1421808; 551228; 452606; 32905; 1377859; 1364213; 1364212; 395407; 22690; 22688; 22686; 22684; 488605; 17680; 1052817; 1008445; 1008443; 992612; 706811; 886683; 747852; 939932; 19003; 1247377; 1247375; 1247373; 862307; 312284; 999462; 999460; 999458; 587450; 763064; 886209; 1176397; 1173557; 902012; 997915; 997914; 997913; 997912; 997911; 997910; 99790; 997908; 997907; 997906; 997905; 997904; 997903; 997902; 997901; 997900; 997319; 997318; 997317; 997316; 997315; 997314; 997313; 997312; 910984; 910983; 910982; 910981; 511604; 169631; 169629; 169627; 168316; 168314; 607633; 555616; 293902; 485371; 455288; 166447; 166445; 166443; 166435; 162551; 160780; 552080; 156719; 156715; 515957; 515956; 515955; 515954; 515953; 459163; 166953; 386678; 169865.

Particularly preferred allergens/antigens include: cat dander protein Fe1 d1; Ragweed proteins Der P1, Der P2 and Der P7; Ragweed protein amb a 1.1, a 1.2, a1.3 or a1.4; Rye grass proteins lol p1 and lol p5; Timothy grass proteins phl p1 and phl p5; Bermuda grass protein Cyn d 5; Alternaria alternate proteins Alt a 1, Alt a 2 and Enolase (Alt a 6); Birch protein Bet v1 and P14; German Cockroach proteins Bla g 1, Bla g 2, Bla g 3, Bla g 4, Bla g 5 and Bla g 6; Mugwort protein Art v 1; Russian thistle protein Sal k 1 and Sal k 2; peanut Ara h1, Ara h2, Ara h3, Ara h4, Ara h5, Ara h6, plant profilins or lipid transfer proteins or a human leukocyte antigen.

Delivery Methods

Once formulated the compositions of the invention can be delivered to a subject in vivo using a variety of known routes and techniques. For example, a composition can be provided as an injectable solution, suspension or emulsion and administered via parenteral, subcutaneous, epicutaneous, epidermal, intradermal, intramuscular, intraarterial, intraperitoneal, intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, sublingual administration, and active or passive transdermal delivery techniques.

Where a peptide of the invention is to be administered, it is preferred to administer the peptide to a site in the body where it will have the ability to contact suitable antigen presenting cells, and where it, or they, will have the opportunity to contact T cells of the individual. Where an APC is to be administered, it is preferred to administer the APC to a site in the body where it will have the ability to contact, and activate, suitable T cells of the individual.

Delivery Regimes

Administration of the peptides/polynucleotides/cells (such as the composition containing a plurality of peptides) may be by any suitable method as described above. Suitable amounts of the peptide may be determined empirically, but typically are in the range given below. A single administration of each peptide may be sufficient to have a beneficial effect for the patient, but it will be appreciated that it may be beneficial if the peptide is administered more than once, in which case typical administration regimes may be, for example, once or twice a week for 2-4 weeks every 6 months, or once a day for a week every four to six months. As will be appreciated, each peptide or polynucleotide, or combination of peptides and/or polynucleotides may be administered to a patient singly or in combination.

Dosages for administration will depend upon a number of factors including the nature of the composition, the route of administration and the schedule and timing of the administration regime. Suitable doses of a molecule of the invention may be in the order of up to 15 ng, up to 20 ng, up to 25 ng, up to 30 ng, up to 50 ng, up to 100 ng, up to 500 ng or more per administration. Suitable doses may be less than 15 ng, but at least 1 ng, or at least 2 ng, or at least 5 ng, or at least 50 ng, or least 100 ng, or at least 500 ng, or at least 1 ng, or at least 10 ng. For some molecules of the invention, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route.

Kits

The invention also relates to a combination of components described herein suitable for use in a treatment of the invention which are packaged in the form of a kit in a container. Such kits may comprise a series of components to allow for a treatment of the invention. For example, a kit may comprise one or more different peptides, polynucleotides and/or cells of the invention, or one or more peptides, polynucleotides or cells of the invention and one or more additional therapeutic agents suitable for simultaneous administration, or for sequential or separate administration. The kit may optionally contain other suitable reagent(s) or instructions and the like.

The invention is illustrated by the following Examples:

Example 1

Potential T Cell Epitopes

The regions of Amb a 1 described below were identified as potentially comprising one or more T cell epitopes:

TABLE 2

| REGION OF INTEREST | RESIDUES IN AMB A 1 (isoform 1.3) | SEQUENCE |
|---|---|---|
| A | 178-189 | GMIKSNDGPPIL (SEQ ID NO: 32) |
| B | 202-213 | GSSQIWIDHCSLSKS (SEQ ID NO: 5) |
| C | 343-354 | DKDLLENGAIFVTSGSDPVLTPVQ (SEQ ID NO: 33) |
| D | 364-375 | PVQSAGMIPAEPGEA (SEQ ID NO: 34) |

TABLE 2-continued

| REGION OF INTEREST | RESIDUES IN AMB A 1 (isoform 1.3) | SEQUENCE |
|---|---|---|
| E | 103-114 | EGTLRFAAAQNRPLW (SEQ ID NO: 35) |
| F | 130-141 | QELVVNSDKTIDGRGVKVEII (SEQ ID NO: 36) |
| G | 376-387 | GEAAIKLTSSAGVFSCHP (SEQ ID NO: 37) |
| H | 226-237 | GSTHVTISNCKF (SEQ ID NO: 22) |
| I | 280-297 | FGFFQVVNNNYDRWGTYA (SEQ ID NO: 38) |
| J | 38-48 | ETRSLQACEALN (SEQ ID NO: 39) |

The sequences provided for regions G, I and J in the priority application, GB 0815258.3 are as follows: GEAAIKLTSSAGVLSCRP(Region G, SEQ ID NO: 40), HGFFQVVNNNYDRGTYA (Region I, SEQ ID NO: 41) and ETRRLTTSGAYN (Region J, SEQ ID NO: 42). These sequences have been corrected in Table 2 such that they correspond to the relevant regions from Amb a 1 isoform 1.3 full length sequence as provided below.

The regions shown in Table 2 were then further analysed to find which of them were highly conserved between the 4 different Amb a1 isoforms as shown below (1.1, 1.2, 1.3 and 1.4). For the below sequences, the following text styles are used to indicate regions of interest: Region A, Region B, Region C, Region D, Region E, Region F, Region G, Region H, Region I, Region J (SEQ ID NO: 43)
Amb 1.1
MGIKHCCYILYFTLALVTLLQPVRSAEDLQEILPVNETRRLTTSGAYNIIDGCWRGKADWAENRKALA
DCAQGFGKGTVGGKDGDIYTVTSELDDDVANPKEGTLRFAAQNRPLWIIFERDMVIRLDKEMVVNSD
KTIDGRGAKVEIINAGFTLNGVKNVIIHNINMHDVKVNPGGLIKSNDGPAAPRAGSDGDAISISGSSQ
IWIDHCSLSKSVDGLVDAKLGTTRLTVSNSLFTQHQFVLLFGAGDENIEDRGMLATVAFNTFTDNVDQ
RMPRCRHGFFQVVNNNYDKWGSYAIGGSASPTILSQGNRFCAPDERSKKNVLGRHGEAAAESMKWNWR
TNKDVLENGAIFVASGVDPVLTPEQSAGMIPAEPGESALSLTSSAGVLSCQPGAPC (SEQ ID NO: 44)
Amb 1.2
MGIKHCCYILYFTLALVTLLQPVRSAEDVEEFLPSANETRRSLKACEAHNIIDKCWRCKADWANNRQA
LADCAQGFAKGTYGGKHGDVYTVTSDKDDDVANPKEGTLRFAAAQNRPLWIIFKRNMVIHLNQELVVN
SDKTIDGRGVKVNIVNAGLTLMNVKNIIIHNINIHDIKVCPGGMIKSNDGPPILRQQSDGDAINVAGS
SQIWIDHCSLSKASDGLLDITLGSSHVTVSNCKFTQHQFVLLLGADDTHYQDKGMLATVAFNMFTDHV
DQRMPRCRFGFFQVVNNNYDRWGTYAIGGSSAPTILSQGNRFFAPDDIIKKNVLARTGTGNAESMSWN
WRTDRDLLENGAIFLPSGSDPVLTPEQKAGMIPAEPGEAVLRLTSSAGVLSCHQGAPC (SEQ ID NO: 45)
Amb 1.3
MGIKQCCYILYFTLALVALLQPVRSAEGVGEILPSVNETRSLQACEALNIIDKCWRGKADWENNRQAL
ADCAQGFAKGTYGGKWGDVYTVTSNLDDDVANPKEGTLRFAAAQNRPLWIIFKNDMVINLNQELVVNS
DKTIDGRGVKVEIINGGLTLMNVKNIIHNINIHDVKVLPGGMIKSNDGPPILRQASDGDTINVAGSS
QIWIDHCSLSKSFDGLVDVTLGSTHVTISNCKFTQQSKAILLGADDTHVQDKGMLATVAFNMFTDNVD
QRMPRCRFGFFQVVNNNYDRWGTYAIGGSSAPTILCQGNRFLAPDDQIKKNVLARTGTGAAESMAWNW
RSDKDLLENGAIFVTSGSDPVLTPVQSAGMIPAEPGEAAIKLTSSAGVFSCHPGAPC -continued Amb 1.4 (SEQ ID NO: 46)
MGIKHCCYILYFTLALVTLLQPVRSAEDLQQILPSAN<u>ETRSLTTCGTYN</u>IIDGCWRGKADWAENRKAL ADCAQGFAKGTIGGKDGDIYTVTSELDDDVANPK<u>EGTLRFGAAQ</u>NRPLWIIFARDMVIRLD<u>RELAINN</u>

<u>DKTIDGRGAKVEII</u>NAGFAIYNVKNIIIHNIIMHDIVVNPG<u>GLIKSHDGPPVP</u>RKGSDGDAIGISGSS

QIWIDHCSLSKAVDGLIDAKH<u>GSTHFTVSNCLF</u>TQHQYLLLFWDFDERGMLCTVAFNKFTDNVDQRMP

NLRHGFVQVVNNNYERWGSYALGGSAGPTILSQGNRFLASDIKKEVVGRYGESAMSESINWNWRS*YMD*

*VFENGAIFVPSGVDPVLT*PEQNAGMIPAEPGEA*VLRLTSSAGVLSCQP*GAPC

The following peptides were considered to be highly conserved and therefore taken forward for further testing:

TABLE 3

| Peptide | Derived from region of interest | Sequence | SEQ ID NO: |
|---|---|---|---|
| RGW01 | A | GMIKSNDGPPI | 1 |
| RGW01A | A | GLIKSHDGPPV | 2 |
| RGW01B | A | GLIKSNDGPAA | 3 |
| RGW02 | B | GSSQIWIDHSSLSKS | 4 |
| RGW02A | B | GSSQIWIDHCSLSKS | 5 |
| RGW02B | B | GGSQIWIDHCSLSKA | 6 |
| RGW03 | C | KDLLENGAIFVTSG | 7 |
| RGW03A | C | DVFENGAIFVPSG | 8 |
| RGW03B | C | RDLLENGAIFLPSG | 9 |
| RGW04 | D | KAGMIPAEPGEA | 10 |
| RGW4A | D | SAGMIPAEPGEA | 11 |
| RGW05 | E | KEGTLRFAAAQNRP | 12 |
| RGW05A | E | KEGTLRFGAAQNRP | 13 |
| RGW06 | F | VVNSDKTIDGRGVKVE | 14 |
| RGW06A | F | AINNDKTIDGRGAKVE | 15 |
| RGW07 | G | GEAAIKLTSSAGVLS | 16 |
| RGW07A | G | GEAVLRLTSSAGVLS | 17 |

TABLE 3-continued

| Peptide | Derived from region of interest | Sequence | SEQ ID NO: |
|---|---|---|---|
| RGW07B | G | GESALSLTSSAGVLS | 18 |
| RGW07C | G | KGEAAIKLTSSAGVLSK | 19 |
| RGW07D | G | KGEAAIKLTSSAGVLSKK | 20 |
| RGW08 | H | GSTHVTISNSKF | 21 |
| RGW08A | H | GSTHVTISNCKF | 22 |
| RGW08B | H | GSTHFTVSNCLF | 23 |
| RGW08C | H | GSTHFTVSNSLF | 24 |
| RGW08D | H | GTTRLTVSNSLF | 25 |
| RGW09 | J | ETRRSLKTSGAYN | 26 |
| RGW10 | I | FGFFQVVNNNYD | 27 |
| RGW10A | I | HGFFQVVNNNYD | 28 |
| RGW11 | I | VNNNYDRWGTYA | 29 |
| RGW11A | I | VNNNYDKWGSYA | 30 |
| RGW11B | I | VNNNYERWGSYA | 31 |

As will be apparent, the sequences above are not necessarily identical to the native sequences of the regions of interest. In particular, the peptides of the invention may be engineered to improve solubility and/or reduce dimer formation and/or reduce the likelihood of IgE cross-linking relative to the native sequences. The following table (Table 4) provides specific illustrations of the above principles as applied by the inventors to produce the peptides of Table 3 (SEQ ID NOS: 1 to 31).

TABLE 4

| Sequence | Identificat<sup>n</sup> | pI | GRAVY | Comments |
|---|---|---|---|---|
| GMIKSNDGPPIL (SEQ ID NO: 32) | Region A | 5.84 | -0.083 | |
| GMIKSNDGPPI | RGW01 (SEQ ID: 1) | 5.84 | -0.436 | Engineered peptide has lower GRAVY score: more soluble |
| GSSQIWIDHCSLSKS (SEQ ID NO: 5) | Region B | 6.73 | -0.273 | |
| GSSQIWIDH<u>S</u>SLSKS | RGW02 (SEQ ID: 4) | 6.73 | -0.493 | Engineered peptide has ser in place of cys (avoids dimer formation) and has |

TABLE 4-continued

| Sequence | Identificat<sup>n</sup> | pI | GRAVY | Comments |
|---|---|---|---|---|
| | | | | lower GRAVY score: more soluble |
| DKDLLENGAIFVTSGSDPVL TPVQ (SEQ ID NO: 33) | Region C | | | |
| RDLLENGAIFLPSG | RGW03B (SEQ ID: 9) | | | Engineered peptide significantly shorter: avoids risk of histamine release via cross linking IgE |
| AIKLTSSAGVFSCHP (SEQ ID NO: 37) | Region G | | | |
| GEAAIKLTSSAGVLS | RGW07 (SEQ ID: 16) | 6.00 | 0.69 | Engineered peptide lacks cys in last three residues (to prevent dimer formation) and has L replacing F as occurs in 1.1, 1.2 and 1.4 |

Rows highlighted in grey in the above table represent the native sequence of a region. The peptides modified according to the invention are shown beneath each native sequence. Residues in bold and underlined represent additions to or substitutions of the native sequence.

Cytokine Assays and Selection of Preferred Combinations

Cytokine secretion profiles from PBMC's of 50 individuals were analysed in response to the peptide stimulation using the peptides of SEQ ID NOS 1 to 31. Supernatants from the cytokine release assay were tested for the presence of IL-13 and IFN-gamma, using a multiplex bead array assay.

A typical cytokine release assay requires $40 \times 10^6$ PBMC's per subject. In more detail, 250 μl of a 200 μg/ml solution of the appropriate antigen or peptide concentration is distributed into the appropriate wells of 48 well plates. Plates are the incubated in a humidified 5% CO2 incubator at 37° C. for a maximum of 4 hours. 250 μl of a $5 \times 10^6$ cell/ml PBMC suspension is then added to each well and the plates returned to the incubator for 5 days. Following stimulation, samples of culture supernatant are harvested for testing by multiplex bead assay according to standard protocols. The data was analysed for subjects having a response to Interferon gamma or IL-13>100 pg/ml and the peptides were prioritised on the basis of the % responder rate as shown below in Table 5.

TABLE 5

| | Number of responders >100 pg/ml | % responders |
|---|---|---|
| RGW 01 | 34 | 68 |
| RGW 01A | 25 | 50 |
| RGW 03 | 25 | 50 |
| RGW 01B | 24 | 48 |
| RGW 04 | 23 | 46 |
| RGW 03A | 22 | 44 |
| RGW 03B | 22 | 44 |
| RGW 10 | 21 | 42 |
| RGW 04A | 20 | 40 |
| RGW 10A | 20 | 40 |
| RGW 05 | 19 | 38 |
| RGW 02 | 18 | 36 |
| RGW 09 | 18 | 36 |
| RGW 06 | 17 | 34 |
| RGW 06A | 17 | 34 |
| RGW 11A | 17 | 34 |
| RGW 05A | 16 | 32 |
| RGW 08B | 10 | 20 |

TABLE 5-continued

| | Number of responders >100 pg/ml | % responders |
|---|---|---|
| RGW 11B | 10 | 20 |
| RGW 02B | 9 | 18 |
| RGW 07A | 9 | 18 |
| RGW 11 | 8 | 16 |
| RGW 08A | 6 | 12 |
| RGW 08D | 6 | 12 |
| RGW 02A | 5 | 10 |
| RGW 07B | 5 | 10 |
| RGW 08 | 4 | 8 |
| RGW 07 | 2 | 4 |
| RGW 08C | 2 | 4 |

Based on the above a preferred combination of the invention was selected to contain:

RGW01 (potentially substituted with RGW01A or RGW01B); and one of RGW03, RGW03A or RGW03B; and one of RGW04 or RGW04A.

From the remaining peptides, the next most potent are RGW02, RGW09, RGW06, RGW06A, RGW10 or RGW10A, RGW05 or RGW05A. A preferred peptide combination may typically comprise at least one additional peptide selected from this group.

Since solubility is a key criterion for peptides to be administered to patients, further in vitro solubility testing was performed to evaluate the solubility of peptides in an acidic environment (pH 2.97 0.1 mM HCl, 0.5% (w/v), 1-thioglycerol (ca. 46 mM), 230 mM trehalose). For example, RGW03B was found to have a solubility of 3.85 mg/ml compared to <0.62 mg/ml for RGW03. Accordingly, the inventors have determined that RGW03B is preferred over RGW03.

FIG. 1 shows the number of individuals who respond to a core mixture of RGW01, RGW03B and RGW04A. A combined analysis of the positive IFNgamma or IL-13 responses for the peptides represented in the core mixture shows that these 3 peptides provide coverage for 38/50 ragweed allergic individuals (76% of the study population). This indicates that the peptides of the core mixture bind to most MHC class II DR molecules and that these complexes are recognized by T cells in the majority of allergic individuals. The incremental effect of adding RGW02, RGW05 and RGW06A is also shown. The benefit of adding epitopes from the second group of peptides is clearly shown.

Figure 2:
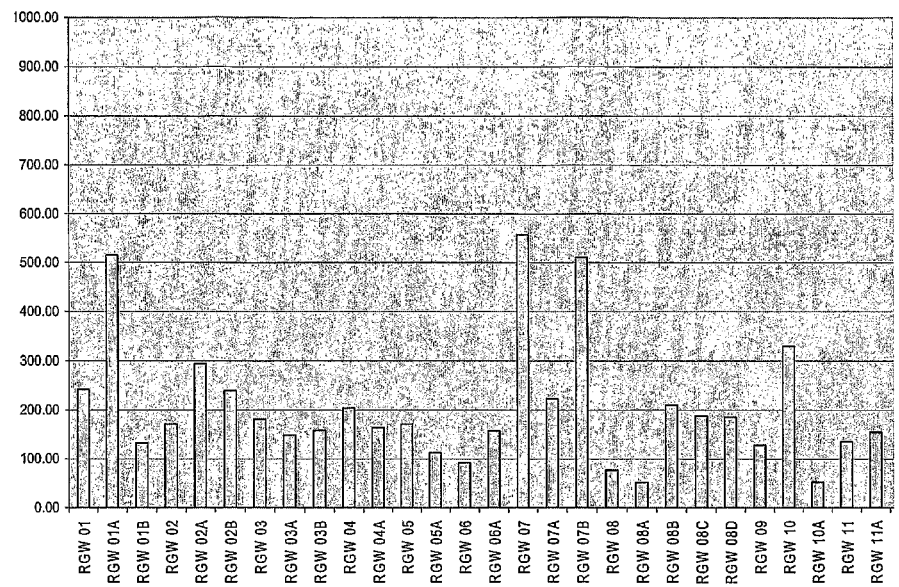
FIG. 2 shows the average production of IL-10 (pg/ml) by PBMCs from ragweed allergic individuals when stimulated with different peptides of the invention.

A further cytokine assay was performed to evaluate IL-10 release from the same panel of individuals, induced by the peptides of SEQ ID NOS. 1 to 31. Analysis of IL-10 response shows that RGW07 and RGW07B induce significant quantities of IL-10 (FIG. 2). RGW07 on its own induced IL-10 in 49/50 individuals. A preferred peptide combination may therefore typically comprise at least one additional peptide selected from the RGW07 group. A combined analysis of the positive IFNgamma or IL-13 responses for the peptides represented in the mixture of 6 peptides identified in FIG. 1 (RGW01+RGW03B+RGW04A+RGW02+RGW05+ RGW06A) together with RGW07 gave a positive IFNgamma or IL-13 response in 49/50 subjects. Thus, this peptide combination effectively covers the whole study population, and complete coverage would be expected on use of improved RGW07 solubility variants (see below). Peptide combinations comprising RGW01+RGW03B+RGW04A+RGW02+ RGW05+RGW06A) or variants thereof together with RGW07 or variants thereof also have the advantage of providing for a positive IL-10 response (see below and FIG. 3).

Figure 3:
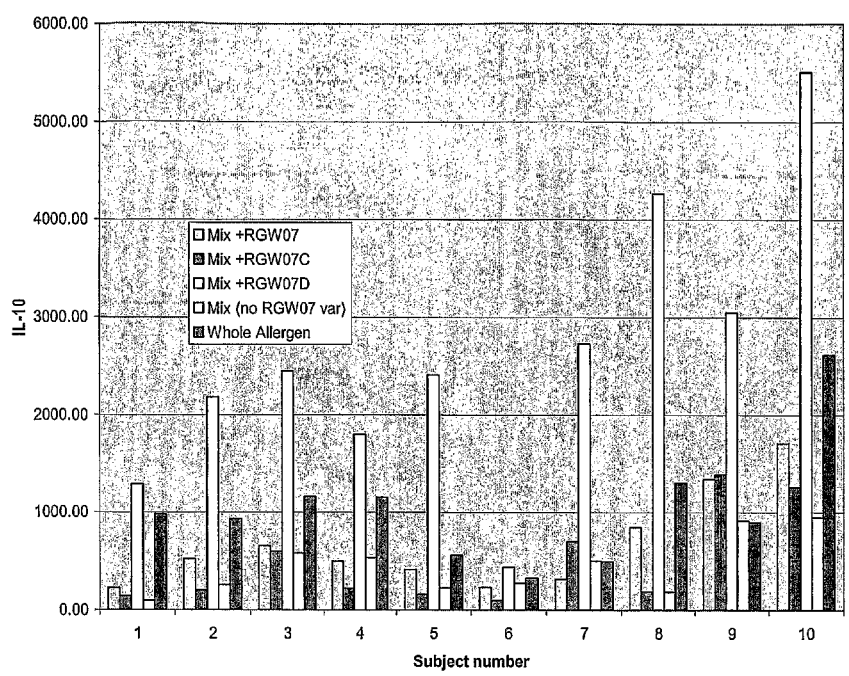
FIG. 3 shows the level of IL-10 (pg/ml) produced by PBMCs from ragweed allergic individuals when stimulated with different peptide combinations.

Solubility testing showed that RGW07 had poor solubility in an acidic environment and so additional lysine residues were added to RGW07 (indicated in Table 6). The modified peptides were tested for solubility and their ability to induce IL-10 from PBMC in the presence of the mixture of peptides identified in FIG. 1 (RGW01+RGW03B+RGW04A+ RGW02+RGW05+RGW06A). Controls included the peptide mixture with no RGW07 variant and with whole Amb a 1 allergen. The results are shown in FIG. 3.

Histamine release from fresh peripheral whole blood from ragweed allergic subjects was evaluated. Peripheral blood basophils were used as a surrogate for tissue mast cells which were not practical to assay. Blood was incubated in vitro with individual peptides identified in Example 1 (RGW01, RGW02, RGW03B, RGW04A, RGW05, RGW06A, RGW07 AND RGW07D). Additionally, responses to preferred mixtures of 7 peptides identified in Example 1 were analysed. The tested preferred mixtures of 7 peptides consisted of i) RGW01, RGW02, RGW03B, RGW04A, RGW05, RGW06A, RGW07 and ii) RGW01, RGW02, RGW03B, RGW04A, RGW05, RGW06A, and RGW07D.

Histamine release in response to whole ragweed allergen extract was measured in each subject to confirm basophil sensitisation. A positive control, representing total histamine release, generated by freeze/thawing the cells twice, was included in each assay. A negative control for spontaneous histamine release was generated by incubating cells in buffer only.

The assay was performed using the Immunotech Histamine Release Immunoassay kit according to the manufacturer's instructions. Following the in vitro challenge of blood basophils with peptides, peptide mixes, whole allergen or buffer in microtitre plate wells, supernatants were removed and the histamine in the samples converted to acyl histamine. Acylated samples were tested by a competitive acyl histamine ELISA.

Peptides were assayed for their ability to induce histamine release over a 5 log 10 range (1 to 10,000 ng/ml). The con-

TABLE 6

Solubility of RGW07 and variants

| Peptide | Sequence | Residues in Amb a 1 | Isoelectric point (pI) | GRAVY | Solubility mg/ml |
|---|---|---|---|---|---|
| RGW07 | GEAAIKLTSSAGVLS (SEQ ID NO: 16) | 376-390 | 6.00 | 0.69 | 0.7 |
| RGW07C | KGEAAIKLTSSAGVLSK (SEQ ID NO: 19) | K376-390K | 9.70 | 0.15 | 1.55 |
| RGW07D | KGEAAIKLTSSAGVLSKK (SEQ ID NO: 20) | K376-390KK | 10.00 | -0.07 | 4.26 |

Based on these analyses, RGW07D was found to be preferred both for solubility and for its ability to induce IL-10 in the presence of the other six peptides.

Example 2

Histamine Release Assay

The purpose of this assay was to identify individual peptides that are capable of activating blood basophils (as a surrogate for tissue mast cells) resulting in histamine release that may result in allergic reactions during therapy. Peptides or combinations of peptides that induce histamine release frequently may be considered unsuitable for inclusion in the peptide vaccine.

Histamine release requires the crosslinking of adjacent specific IgE molecules on the surface of the basophil. The peptides being evaluated were small (11 to 18 amino acids in length) and should not, therefore, possess significant tertiary structure that would enable them to retain the conformation of an IgE-binding epitope of the whole molecule. Furthermore, peptide monomers in solution, even if they are bound by IgE, should not be able to crosslink adjacent IgE molecules.

centration range assayed was selected based on theoretical in vivo doses of peptide that may be achieved during therapy. For example, a 31 µg dose (approximately 3 nmol/peptide equivalent) of each peptide entering a blood volume of 5 liters, would result in a blood concentration of 6 ng/ml, at the lower end of the histamine release assay dose range. Whole ragweed allergen extract was used over a slightly higher concentration range (10 to 100,000 ng/ml).

Single measurements were performed for each dilution. After completion of the ELISA, individual histamine levels were determined by interpolation from the standard curve generated in the ELISA assay. Results from samples were adjusted to allow for dilution. Where two or more consecutive dilutions of a peptide/allergen preparation elicited >15% of the total histamine release seen in the freeze thawed positive control (>15% of positive control), or where a single value of >15% of positive control was achieved at the highest concentration tested (10 ng/mL for peptides), this was considered a "positive histamine release".

A total of 49 histamine release assays were completed during the study. Of these 6 assays were rejected, due to unacceptably high levels (>15% of positive control) of spontaneous release in the medium plus buffer negative control wells. Therefore a total of 43 subjects were included in the analysis. 20 of these subjects were tested with the RGW07D peptide and the mix containing it. The study findings are summarised in Table 7.

TABLE 7

| Peptide or combination | Subjects with histamine release >15% of positive control | Mean histamine release of 43 or 20 subjects as a % of positive control at 10 µg/mL | Maximum histamine release (% of positive control at 10 µg/mL) |
|---|---|---|---|
| 1) RGW 01 | 0/43 | 1% | 0% |
| 2) RGW 03B | 0/43 | 1% | 0% |
| 3) RGW 04A | 0/43 | 0% | 0% |
| 4) RGW 05 | 0/43 | 0% | 0% |
| 5) RGW 02 | 0/43 | 1% | 0% |
| 6) RGW 06A | 0/43 | 1% | 0% |
| 7) RGW 07 | 0/43 | 1% | 0% |
| 8) Peptides 1-6 and RGW07 in combination | 0/43 | 1% | 0% |
| 9) RGW 07D | 0/20 | 3% | 0% |
| 10) Peptides 1-6 and RGW07D in combination | 2/20* | 5% | 20% |
| Ragweed allergen control | 28/43 | 25% | 78% |

*Peptides 1-6 and RGW07D in combination were >15% in two subjects only at 10 µg/ml.

Results are shown for the highest dose of peptides tested in the assay (10 µg/ml). The ragweed allergen control induced significant histamine release in 65% of the 43 subjects. Even at the lowest concentration of 10 ng/ml, the whole allergen extract induced significant histamine release in 22/43 (51%) of individuals with a mean release for the 43 subjects of 30% of positive control. The crude whole ragweed extract contains approximately 0.5% of major allergen Amb a1, emphasizing the exquisite sensitivity of the in vitro basophil assay for assessing the safety of the peptides which at 10 ug/ml are present at >10,000 fold excess over Amb a1 in the crude extract at 10 ng/ml.

The data shows that the eight individual peptides do not elicit significant histamine release from the basophils of ragweed allergic individuals when compared to whole allergen. A combination of peptides RGW01, RGW02, RGW03B, RGW04A, RGW05, RGW06A, RGW07 also failed to elicit significant histamine release in the 43 subjects.

The combination of peptides RGW01, RGW02, RGW03B, RGW04A, RGW05, RGW06A, and RGW07D gave a weak positive response in 2 individuals with values of 16% and 20% of positive control at the highest peptide concentration of 10 µg/mL. The % release values at the four lower concentrations tested were <15%, i.e. negative. Given the large excess of peptide dose tested in this assay compared to likely blood concentrations of the peptides following clinical dosing—the highest concentration tested represents >1000-fold excess over the expected blood concentrations—it is not anticipated that this peptide combination will cause significant histamine release either by IgE-mediated or direct peptide-mediated basophil or mast cell activation and degranulation.

Example 3

Clinical Trial of Peptide Combination

A preferred mixture of 7 peptides consisting of peptides RGW01, RGW02, RGW03B, RGW04A, RGW05, RGW06A, and RGW07D is tested in a randomised, placebo-controlled, blind clinical trial. The efficacy of this mixture in reducing allergic symptoms is evaluated. The study design of the clinical trial is in accordance with good clinical practice guidelines.

Ragweed-allergic subjects are screened to identify late phase skin response (LPSR) and conjunctival provocation test (CPT) scores following challenge with ragweed allergen. Details of LPSR and CPT assays are provided below. Titrations are performed in order to identify the minimally effective concentrations of whole allergen for generation of an appropriate LPSR and CPT score. Blood samples are taken to evaluate levels of ragweed-specific IgE.

Baseline skin and conjunctival responses to ragweed allergen for all subjects are established using a Baseline Challenge which takes place between 1 to 4 weeks prior to study medication administration. An intradermal injection of ragweed allergen at the minimally effective concentration identified in screening is administered into the volar surface of a selected forearm. Subjects are assessed to ensure that they experience a early phase skin response (EPSR), a CPT and a Late-Phase Skin Response (LPSR) to whole ragweed allergen, and the magnitude of the baseline reaction is recorded as follows:

15 minutes (±3 minutes) after the injection, the outline of any EPSR is drawn onto the skin with a ballpoint pen. The longest and orthogonal diameters are measured and recorded for each response, and the area of the response in each arm is calculated.

At a minimum of 30 minutes after the injection, ragweed allergen at the minimally effective concentration identified in screening is instilled into a selected eye. Subject rated itching and observer rated redness and watering is then scored after 5 minutes (±2 minutes). The scoring system is shown in Table 8 below.

Eight hours (±10 minutes) after each injection the outline of any late-phase response is drawn onto the skin with a ballpoint pen. The longest and orthogonal diameters are measured and recorded for each response, and the area of the response in each arm is calculated.

Subjects who produce a suitable baseline reaction are assigned to dosing groups, randomised and entered into the Treatment Phase.

TABLE 8

| Symptom | Score |
|---|---|
| Redness of conjunctiva (observer rated) | 0 = none<br>1 = slight (just perceptible)<br>2 = moderate (noticeable redness)<br>3 = severe (intense angry redness) |
| Watering (observer rated) | 0 = none<br>1 = slight (just perceptible)<br>2 = moderate (occasional tearing)<br>3 = severe (tears running down cheek) |
| Itching (self-evaluated) | 0 = none<br>1 = slight (occasional tingling sensation)<br>2 = moderate (noticeable itching but no need to rub eye)<br>3 = severe (itching with need to rub eye)<br>4 = unbearable (unbearable itching with a compulsive desire to rub eye) |

The Treatment Phase consists of a period of 6 weeks for each subject. During this period one group of subjects receive a single intradermal injection of either the preferred mixture (0.03, 0.3, 3, 1, 12 nmol of each peptide per dose) or diluent placebo at Treatment Phase Visit 1 on day one. Intradermal injections are made into the flexor surface of the selected forearm. A repeat administration is then performed at Treatment Phase Visits 2, 3 and 4, each two weeks apart (14±2 days). A cohort of 10 subjects receives treatment at each dose level (8 receive the preferred mixture and 2 placebo). The first cohort receives 0.03 nmol of each peptide in the mixture and each subsequent cohort in the group receives the next higher dose level.

19 to 28 weeks after the beginning of treatment subjects have their skin and conjunctival responses to whole allergen retested in a post-treatment challenge (PTC). Skin responses to ragweed allergen are assessed by measurement of the EPSR and LPSR as described above. The average area of response is calculated as described above. Conjunctival responses to ragweed allergen are assessed by measurement of the CPT as described above. Blood samples are taken for measurement of ragweed specific IgE.

The average EPSR area after treatment is compared to the baseline EPSR area for each subject. The overall change in EPSR area for all ten patients in each cohort is then evaluated. The average LPSR area after treatment is compared to the baseline LPSR area for each subject. The overall change in LPSR area for all ten patients in each cohort is then evaluated. The CPT score after treatment is compared to the baseline CPT score for each subject. The overall change in CPT score for all ten patients in each cohort is then evaluated.

FURTHER EMBODIMENTS OF THE INVENTION

I. A composition for use in preventing or treating allergy to ragweed by tolerisation comprising at least three polypeptides, wherein the polypeptides are independently selected from any of the following:
(i) a polypeptide of any of SEQ ID NO's. 1 to 31; or
(ii) a variant of a polypeptide according to (i), wherein said variant is a polypeptide of length 9 to 30 amino acids that comprises a region consisting of:
any of the sequences of (i); or
a sequence which has at least 65% homology to any of the sequences of (i) which sequence is capable of tolerising an individual to any of the sequences of (i), or
(iii) a variant of a polypeptide according to (i), wherein said variant is a polypeptide of length 9 to 30 amino acids that comprises a region consisting of a sequence that represents either:
a fragment of any of the sequences of (i); or a homologue of a fragment of any of the sequences of (i),
which sequence is capable of tolerising an individual to any of the sequences of (i) and has a length of at least 9 amino acids, and wherein said homologue has at least 65% homology to any 9 contiguous amino acids in any of the sequences of (i).

II. The composition according to item I, wherein the composition:
a) is capable of tolerising at least 50% or at least 60% of a panel of ragweed allergic individuals in the population; and/or
b) comprises at least three polypeptides selected from item I(i) or variants thereof as defined in item I(ii) or I(iii), and/or
c) comprises at least one further polypeptide up to a total of thirteen unique/different polypeptides, wherein the further polypeptides:
comprise a sequence having at least 65% sequence identity to at least 9 or more contiguous amino acids in any of SEQ ID NO: 1 to 31 above not selected in (a); and
are 9 to 30 amino acids in length; and/or
d) comprises up to a maximum of thirteen polypeptides.

III. The composition according to item I or II, comprising at least one polypeptide according to item II(c) which is 9 to 20 or 13 to 17 amino acids in length and/or wherein said polypeptide has at least 70% sequence identity to at least 9 or more contiguous amino acids in any of SEQ ID NO: 1 to 31.

IV. A composition according to any one of the preceding items, comprising at least one polypeptide selected from a polypeptide of RGW01, RGW01A or RGW01B (SEQ ID NOS: 1, 2 or 3) or a variant thereof as defined in item I(ii) or (iii).

V. A composition according to item IV, wherein the at least one polypeptide is the polypeptide RGW01, or a variant thereof.

VI. A composition according to item IV or V, comprising at least one polypeptide selected from a polypeptide of RGW03B, RGW03A or RGW03 (SEQ ID NOS: 9, 8 or 7), or a variant thereof as defined in item I(ii) or (iii);

VII. A composition according to item VI wherein the at least one polypeptide is the polypeptide RGW03B, or a variant thereof.

VIII. A composition according to any one of items IV to VII, comprising at least one polypeptide selected from a polypeptide of RGW04 or RGW04A (SEQ ID NOS: 10 or 11), or a variant thereof as defined in item I(ii) or (iii).

IX. A composition according to any one of items IV to VIII, comprising at least one polypeptide selected from a polypeptide of RGW02, RGW09, RGW06, RGW06A, RGW10 or RGW10A, RGW05 or RGW05A (SEQ ID NOS: 4, 26, 14, 15, 27, 12 or 13), or a variant thereof as defined in item I(ii) or (iii).

X. A composition according to any one of items IV to IX, comprising at least one polypeptide selected from a polypeptide of RGW07, RGW07C or RGW07D (SEQ ID NOS: 16, 19 or 20), or a variant thereof as defined in item I(ii) or (iii).

XI. A composition according to item X, wherein the at least one polypeptide is RGW07D (SEQ ID NO: 20).

XII. A composition according to any one of the preceding items consisting of:
a) at least one of the polypeptides of RGW01, RGW01A or RGW01B (SEQ ID NOS: 1, 2 or 3), or a variant thereof as defined in item I(ii) or (iii); and
b) at least one of the polypeptides of RGW03B, RGW03A or RGW03 (SEQ ID NOS: 9, 8 or 7), or a variant thereof as defined in item I(ii) or (iii); and
c) at least one of the polypeptides of RGW04 or RGW04A (SEQ ID NOS: 10 or 11), or a variant thereof as defined in item I(ii) or (iii); and optionally
d) at least one of the polypeptides of RGW02, RGW09, RGW06, RGW06A, RGW10 or RGW10A, RGW05 or RGW05A (SEQ ID NOS: 4, 26, 14, 15, 27, 12 or 13), or a variant thereof as defined in item I(ii) or (iii); and optionally
e) at least one of the polypeptides of RGW07, RGW07C or RGW07D (SEQ ID NOS: 16, 19 or 20), or a variant thereof as defined in item I(ii) or (iii).

XIII. The composition according to any one of the preceding items, wherein one or more of the polypeptides have one or more modifications selected from the following:
(i) N terminal acetylation;
(ii) C terminal amidation;
(iii) one or more hydrogen on the side chain amines of Arginine and/or Lysine replaced with a methylene group;
(iv) glycosylation; and
(v) phosphorylation.

XIV. The composition according to any one of the preceding items wherein at least one of the peptides has been engineered to be soluble such that it comprises:

i) N terminal to the residues of the peptide which flank a T cell epitope: one to six contiguous amino acids corresponding to the two to six contiguous amino acids immediately N terminal to said residues in the sequence of the protein from which the peptide derives; and/or ii) C terminal to the residues of the peptide which flank a T cell epitope: one to six contiguous amino acids corresponding to the one to six contiguous amino acids immediately C terminal to the said residues in the sequence of the protein from which the peptide derives; or iii) N and/or C terminal to the residues of the peptide which flank a T cell epitope, at least one amino acid selected from arginine, lysine, histidine, glutamate and aspartate, wherein the polypeptide has a solubility of at least 3.5 mg/ml and the T cell epitope has a solubility of less than 3.5 mg/ml.

XV. The composition according to any one of the preceding items wherein at least one of the peptides has been engineered to be soluble such that additionally:

i) any cysteine residues in the native sequence of the peptide are replaced with serine or 2-aminobutyric acid; and/or ii) any hydrophobic residues in the upto three amino acids at the N and/or C terminus of the native sequence of the peptide, which are not comprised in a T cell epitope, are deleted; and/or iii) any two consecutive amino acids comprising the sequence Asp-Gly in the upto four amino acids at the N and/or C terminus of the native sequence of the peptide, which are not comprised in a T cell epitope, are deleted.

XVI. The composition according to any one of the preceding items wherein each polypeptide has a concentration in the range of 0.03 to 200 nmol/ml, 0.3 to 200 nmol/ml or 30 to 120 nmol/ml.

XVII. A composition for use in preventing or treating allergy to ragweed by tolerisation comprising at least three polynucleotide sequences which when expressed cause the production of a composition as defined in any one of items I to XVI.

XVIII. The composition according to item XVII, wherein each polynucleotide sequence capable of expressing a different polypeptide is present in the same or different polynucleotide vectors.

XIX. A vector for use in preventing or treating allergy to ragweed by tolerisation comprising at least three polynucleotide sequences which each encode a different polypeptide as defined in item I and optionally one or more further polynucleotide sequences which encode different polypeptides as defined in item II.

XX. A vector for use in preventing or treating allergy to ragweed by tolerisation comprising between three and thirteen different polynucleotide sequences, which each encode a different polypeptide as defined in item I or II, wherein at least one polynucleotide encodes a polypeptide selected from each of the following groups of polypeptides:

a) RGW01, RGW01A or RGW01B (SEQ ID NOS: 1, 2 or 3;

b) RGW03B, RGW03A or RGW03 (SEQ ID NOS: 9, 8 or 7); and c) RGW04 or RGW04A (SEQ ID NOS: 10 or 11).

XXI. A product containing between three and thirteen polypeptides, wherein at least one polypeptide is selected from each of the following groups of polypeptides:

a) RGW01, RGW01A or RGW01B (SEQ ID NOS: 1, 2 or 3) or a variant thereof as defined in item I(ii) or (iii);

b) RGW03B, RGW03A or RGW03 (SEQ ID NOS: 9, 8 or 7) or a variant thereof as defined in item I(ii) or (iii); and c) RGW04 or RGW04A (SEQ ID NOS: 10 or 11) or a variant thereof as defined in item I(ii) or (iii);

wherein each different polypeptide is for simultaneous, separate or sequential use in preventing or treating allergy to ragweed by tolerisation.

XXII. A product containing between three and thirteen polynucleotide sequences, which each encode a different polypeptide as defined in item I or II, wherein at least one polynucleotide encodes a polypeptide selected from each of the following groups of polypeptides:

a) RGW01, RGW01A or RGW01B (SEQ ID NOS: 1, 2 or 3;

b) RGW03B, RGW03A or RGW03 (SEQ ID NOS: 9, 8 or 7); and c) RGW04 or RGW04A (SEQ ID NOS: 10 or 11);

and wherein each different polypeptide is for simultaneous, separate or sequential use in the prevention or treatment of allergy to ragweed in a human.

XXIII. A pharmaceutical formulation for use in preventing or treating allergy to ragweed by tolerisation comprising a composition according to any one of items I to XVIII; a vector according to any one of items XIX or XX; or a product according to any one of items XXI or XXII; and a pharmaceutically acceptable carrier or diluent.

XXIV. The composition, vector or product according to item XXIII, formulated for oral administration, nasal administration, epicutaneous administration, subcutaneous administration, sublingual administration, intradermal administration, buccal administration or for administration by inhalation or by injection.

XXV. The composition as defined in any one of items I to XVIII or product as defined in item XXI or XXII, additionally comprising a further polypeptide allergen for use in tolerising an individual to the further polypeptide allergen.

XXVI. An in vitro method of determining whether T cells recognize a polypeptide as defined in item I comprising contacting said T cells with said polypeptide and detecting whether said T cells are stimulated by said polypeptide.

XXVII. An in vitro method of determining whether an individual has or is at risk of a condition wherein the condition is characterized by allergic symptoms in response to a ragweed allergen, the method comprising testing whether the individual has T cells which respond to a composition as defined in any one of items I to XVIII, thereby determining whether the individual has or is at risk of the condition.

XXVIII. A method according to item XXVII wherein a T-cell immune response to said composition is measured by contacting the composition with T cells in a sample taken from the subject, under conditions which allow the composition and the T cells to interact; and determining whether or not any of the T cells are stimulated and thereby determining whether or not a T-cell immune response is present or absent.

The invention claimed is:

1. A composition suitable for use in treating allergy to ragweed comprising:
 (a) at least one polypeptide selected from the group consisting of RDLLENGAIFLPSG (SEQ ID NO: 9), DVFENGAIFVPSG (SEQ ID NO: 8), and KDLLENGAIFVTSG (SEQ ID NO: 7);
 (b) at least one polypeptide selected from the group consisting of GMIKSNDGPPI (SEQ ID NO: 1), GLIKSHDGPPV (SEQ ID NO: 2) and GLIKSNDGPAA (SEQ ID NO: 3); and
 (c) at least one polypeptide selected from the group consisting of KAGMIPAEPGEA (SEQ ID NO: 10) and SAGMIPAEPGEA (SEQ ID NO: 11),
and an effective amount of a preservative or adjuvant.

2. The composition according to claim 1, which comprises the polypeptide GMIKSNDGPPI (SEQ ID NO:1); the polypeptide RDLLENGAIFLPSG (SEQ ID NO:9); and the polypeptide SAGMIPAEPGEA (SEQ ID NO:11).

3. The composition according to claim 1, which further comprises at least one polypeptide selected from a polypeptide of GSSQIWIDHSSLSKS (SEQ ID NO: 4), ETRRSLKTSGAYN (SEQ ID NO: 26), VVNSDKTIDGRGVKVE (SEQ ID NO: 14), AINNDKTIDGRGAKVE (SEQ ID NO: 15), FGFFQVVNNNYD (SEQ ID NO: 27), HGFFQVVNNNYD (SEQ ID NO: 28), KEGTLRFAAAQNRP (SEQ ID NO: 12), or KEGTLRFGAAQNRP (SEQ ID NO: 13); and optionally further comprising a polypeptide of GEAAIKLTSSAGVLS (SEQ ID NO: 16), KGEAAIKLTSSAGVLSK (SEQ ID NO: 19), or KGEAAIKLTSSAGVLSKK (SEQ ID NO: 20).

4. The composition according to claim 1, which further comprises GMIKSNDGPPI (SEQ ID NO:1); RDLLENGAIFLPSG (SEQ ID NO:9); SAGMIPAEPGEA (SEQ ID NO:11); GSSQIWIDHSSLSKS (SEQ ID NO:4); KEGTLRFAAAQNRP (SEQ ID NO:12); AINNDKTIDGRGAKVE (SEQ ID NO:15); and KGEAAIKLTSSAGVLSKK (SEQ ID NO:20).

5. The composition according to claim 1, wherein: one or more of the polypeptides have one or more modifications selected from the group consisting of:

(a) N terminal acetylation;
(b) C terminal amidation;
(c) one or more hydrogen on the side chain amines of Arginine and/or Lysine replaced with a methylene group;
(d) glycosylation; and
(e) phosphorylation.

6. The composition according to claim 1, which is a solution in which each polypeptide has a concentration in the range of 0.03 to 200 nmol/ml.

7. The composition according to claim 1, which is a solution in which each polypeptide has a concentration in the range of 0.3 to 200 nmol/ml.

8. The composition according to claim 1, which is a solution in which each polypeptide has a concentration in the range of 30 to 200 nmol/ml.

9. The composition according to claim 1, which is a pharmaceutical formulation comprising a pharmaceutically acceptable carrier or diluent.

10. The pharmaceutical formulation according to claim 9, formulated for oral administration, nasal administration, epicutaneous administration, subcutaneous administration, sublingual administration, intradermal administration, buccal administration or for administration by inhalation or by injection.

11. A composition suitable for use in treating allergy to ragweed comprising:
   (a) at least one polypeptide selected from the group consisting of RDLLENGAIFLPSG (SEQ ID NO: 9), DVFENGAIFVPSG (SEQ ID NO: 8), and KDLLENGAIFVTSG (SEQ ID NO: 7);
   (b) at least one polypeptide selected from the group consisting of GMIKSNDGPPI (SEQ ID NO: 1), GLIKSHDGPPV (SEQ ID NO: 2) and GLIKSNDGPAA (SEQ ID NO: 3); and
   (c) at least one polypeptide selected from the group consisting of KAGMIPAEPGEA (SEQ ID NO: 10) and SAGMIPAEPGEA (SEQ ID NO: 11), and
an effective amount of a preservative or adjuvant, wherein each polypeptide is present in an amount of 100 ng to 2 mg.

* * * * *

SEQUENCE LISTING

<160> NUMBER OF SEQ ID NOS: 150

<210> SEQ ID NO 1

-continued

```
<211> LENGTH: 11
<212> TYPE: PRT
<213> ORGANISM: Ambrosia artemisiifolia

<400> SEQUENCE: 1

Gly Met Ile Lys Ser Asn Asp Gly Pro Pro Ile
1               5                   10

<210> SEQ ID NO 2
<211> LENGTH: 11
<212> TYPE: PRT
<213> ORGANISM: Ambrosia artemisiifolia

<400> SEQUENCE: 2

Gly Leu Ile Lys Ser His Asp Gly Pro Pro Val
1               5                   10

<210> SEQ ID NO 3
<211> LENGTH: 11
<212> TYPE: PRT
<213> ORGANISM: Ambrosia artemisiifolia

<400> SEQUENCE: 3

Gly Leu Ile Lys Ser Asn Asp Gly Pro Ala Ala
1               5                   10

<210> SEQ ID NO 4
<211> LENGTH: 15
<212> TYPE: PRT
<213> ORGANISM: Artificial
<220> FEATURE:
<223> OTHER INFORMATION: synthetic peptide

<400> SEQUENCE: 4

Gly Ser Ser Gln Ile Trp Ile Asp His Ser Ser Leu Ser Lys Ser
1               5                   10                  15

<210> SEQ ID NO 5
<211> LENGTH: 15
<212> TYPE: PRT
<213> ORGANISM: Ambrosia artemisiifolia

<400> SEQUENCE: 5

Gly Ser Ser Gln Ile Trp Ile Asp His Cys Ser Leu Ser Lys Ser
1               5                   10                  15

<210> SEQ ID NO 6
<211> LENGTH: 15
<212> TYPE: PRT
<213> ORGANISM: Ambrosia artemisiifolia

<400> SEQUENCE: 6

Gly Gly Ser Gln Ile Trp Ile Asp His Cys Ser Leu Ser Lys Ala
1               5                   10                  15

<210> SEQ ID NO 7
<211> LENGTH: 14
<212> TYPE: PRT
<213> ORGANISM: Ambrosia artemisiifolia

<400> SEQUENCE: 7

Lys Asp Leu Leu Glu Asn Gly Ala Ile Phe Val Thr Ser Gly
1               5                   10

<210> SEQ ID NO 8
```

```
<211> LENGTH: 13
<212> TYPE: PRT
<213> ORGANISM: Ambrosia artemisiifolia

<400> SEQUENCE: 8

Asp Val Phe Glu Asn Gly Ala Ile Phe Val Pro Ser Gly
1               5                   10

<210> SEQ ID NO 9
<211> LENGTH: 14
<212> TYPE: PRT
<213> ORGANISM: Ambrosia artemisiifolia

<400> SEQUENCE: 9

Arg Asp Leu Leu Glu Asn Gly Ala Ile Phe Leu Pro Ser Gly
1               5                   10

<210> SEQ ID NO 10
<211> LENGTH: 12
<212> TYPE: PRT
<213> ORGANISM: Ambrosia artemisiifolia

<400> SEQUENCE: 10

Lys Ala Gly Met Ile Pro Ala Glu Pro Gly Glu Ala
1               5                   10

<210> SEQ ID NO 11
<211> LENGTH: 12
<212> TYPE: PRT
<213> ORGANISM: Ambrosia artemisiifolia

<400> SEQUENCE: 11

Ser Ala Gly Met Ile Pro Ala Glu Pro Gly Glu Ala
1               5                   10

<210> SEQ ID NO 12
<211> LENGTH: 14
<212> TYPE: PRT
<213> ORGANISM: Ambrosia artemisiifolia

<400> SEQUENCE: 12

Lys Glu Gly Thr Leu Arg Phe Ala Ala Ala Gln Asn Arg Pro
1               5                   10

<210> SEQ ID NO 13
<211> LENGTH: 14
<212> TYPE: PRT
<213> ORGANISM: Ambrosia artemisiifolia

<400> SEQUENCE: 13

Lys Glu Gly Thr Leu Arg Phe Gly Ala Ala Gln Asn Arg Pro
1               5                   10

<210> SEQ ID NO 14
<211> LENGTH: 16
<212> TYPE: PRT
<213> ORGANISM: Ambrosia artemisiifolia

<400> SEQUENCE: 14

Val Val Asn Ser Asp Lys Thr Ile Asp Gly Arg Gly Val Lys Val Glu
1               5                   10                  15

<210> SEQ ID NO 15
<211> LENGTH: 16
<212> TYPE: PRT
```

-continued

<213> ORGANISM: Ambrosia artemisiifolia

<400> SEQUENCE: 15

Ala Ile Asn Asn Asp Lys Thr Ile Asp Gly Arg Gly Ala Lys Val Glu
1               5                   10                  15

<210> SEQ ID NO 16
<211> LENGTH: 15
<212> TYPE: PRT
<213> ORGANISM: Artficial
<220> FEATURE:
<223> OTHER INFORMATION: synthetic peptide

<400> SEQUENCE: 16

Gly Glu Ala Ala Ile Lys Leu Thr Ser Ser Ala Gly Val Leu Ser
1               5                   10                  15

<210> SEQ ID NO 17
<211> LENGTH: 15
<212> TYPE: PRT
<213> ORGANISM: Ambrosia artemisiifolia

<400> SEQUENCE: 17

Gly Glu Ala Val Leu Arg Leu Thr Ser Ser Ala Gly Val Leu Ser
1               5                   10                  15

<210> SEQ ID NO 18
<211> LENGTH: 15
<212> TYPE: PRT
<213> ORGANISM: Ambrosia artemisiifolia

<400> SEQUENCE: 18

Gly Glu Ser Ala Leu Ser Leu Thr Ser Ser Ala Gly Val Leu Ser
1               5                   10                  15

<210> SEQ ID NO 19
<211> LENGTH: 17
<212> TYPE: PRT
<213> ORGANISM: Artificial
<220> FEATURE:
<223> OTHER INFORMATION: synthetic peptide

<400> SEQUENCE: 19

Lys Gly Glu Ala Ala Ile Lys Leu Thr Ser Ser Ala Gly Val Leu Ser
1               5                   10                  15

Lys

<210> SEQ ID NO 20
<211> LENGTH: 18
<212> TYPE: PRT
<213> ORGANISM: Artificial
<220> FEATURE:
<223> OTHER INFORMATION: synthetic peptide

<400> SEQUENCE: 20

Lys Gly Glu Ala Ala Ile Lys Leu Thr Ser Ser Ala Gly Val Leu
1               5                   10                  15

Ser Lys Lys

<210> SEQ ID NO 21
<211> LENGTH: 12
<212> TYPE: PRT
<213> ORGANISM: Artificial
<220> FEATURE:
<223> OTHER INFORMATION: synthetic peptide

```
<400> SEQUENCE: 21

Gly Ser Thr His Val Thr Ile Ser Asn Ser Lys Phe
1               5                   10

<210> SEQ ID NO 22
<211> LENGTH: 12
<212> TYPE: PRT
<213> ORGANISM: Ambrosia artemisiifolia

<400> SEQUENCE: 22

Gly Ser Thr His Val Thr Ile Ser Asn Cys Lys Phe
1               5                   10

<210> SEQ ID NO 23
<211> LENGTH: 12
<212> TYPE: PRT
<213> ORGANISM: Ambrosia artemisiifolia

<400> SEQUENCE: 23

Gly Ser Thr His Phe Thr Val Ser Asn Cys Leu Phe
1               5                   10

<210> SEQ ID NO 24
<211> LENGTH: 12
<212> TYPE: PRT
<213> ORGANISM: Artificial
<220> FEATURE:
<223> OTHER INFORMATION: synthetic peptide

<400> SEQUENCE: 24

Gly Ser Thr His Phe Thr Val Ser Asn Ser Leu Phe
1               5                   10

<210> SEQ ID NO 25
<211> LENGTH: 12
<212> TYPE: PRT
<213> ORGANISM: Ambrosia artemisiifolia

<400> SEQUENCE: 25

Gly Thr Thr Arg Leu Thr Val Ser Asn Ser Leu Phe
1               5                   10

<210> SEQ ID NO 26
<211> LENGTH: 13
<212> TYPE: PRT
<213> ORGANISM: Artficial
<220> FEATURE:
<223> OTHER INFORMATION: synthetic peptide

<400> SEQUENCE: 26

Glu Thr Arg Arg Ser Leu Lys Thr Ser Gly Ala Tyr Asn
1               5                   10

<210> SEQ ID NO 27
<211> LENGTH: 12
<212> TYPE: PRT
<213> ORGANISM: Ambrosia artemisiifolia

<400> SEQUENCE: 27

Phe Gly Phe Phe Gln Val Val Asn Asn Asn Tyr Asp
1               5                   10

<210> SEQ ID NO 28
<211> LENGTH: 12
```

```
<212> TYPE: PRT
<213> ORGANISM: Ambrosia artemisiifolia

<400> SEQUENCE: 28

His Gly Phe Phe Gln Val Val Asn Asn Asn Tyr Asp
1               5                   10

<210> SEQ ID NO 29
<211> LENGTH: 12
<212> TYPE: PRT
<213> ORGANISM: Ambrosia artemisiifolia

<400> SEQUENCE: 29

Val Asn Asn Asn Tyr Asp Arg Trp Gly Thr Tyr Ala
1               5                   10

<210> SEQ ID NO 30
<211> LENGTH: 12
<212> TYPE: PRT
<213> ORGANISM: Ambrosia artemisiifolia

<400> SEQUENCE: 30

Val Asn Asn Asn Tyr Asp Lys Trp Gly Ser Tyr Ala
1               5                   10

<210> SEQ ID NO 31
<211> LENGTH: 12
<212> TYPE: PRT
<213> ORGANISM: Ambrosia artemisiifolia

<400> SEQUENCE: 31

Val Asn Asn Asn Tyr Glu Arg Trp Gly Ser Tyr Ala
1               5                   10

<210> SEQ ID NO 32
<211> LENGTH: 12
<212> TYPE: PRT
<213> ORGANISM: Ambrosia artemisiifolia

<400> SEQUENCE: 32

Gly Met Ile Lys Ser Asn Asp Gly Pro Pro Ile Leu
1               5                   10

<210> SEQ ID NO 33
<211> LENGTH: 24
<212> TYPE: PRT
<213> ORGANISM: Ambrosia artemisiifolia

<400> SEQUENCE: 33

Asp Lys Asp Leu Leu Glu Asn Gly Ala Ile Phe Val Thr Ser Gly Ser
1               5                   10                  15

Asp Pro Val Leu Thr Pro Val Gln
            20

<210> SEQ ID NO 34
<211> LENGTH: 15
<212> TYPE: PRT
<213> ORGANISM: Ambrosia artemisiifolia

<400> SEQUENCE: 34

Pro Val Gln Ser Ala Gly Met Ile Pro Ala Glu Pro Gly Glu Ala
1               5                   10                  15

<210> SEQ ID NO 35
```

```
<211> LENGTH: 15
<212> TYPE: PRT
<213> ORGANISM: Ambrosia artemisiifolia

<400> SEQUENCE: 35

Glu Gly Thr Leu Arg Phe Ala Ala Ala Gln Asn Arg Pro Leu Trp
1               5                   10                  15

<210> SEQ ID NO 36
<211> LENGTH: 21
<212> TYPE: PRT
<213> ORGANISM: Ambrosia artemisiifolia

<400> SEQUENCE: 36

Gln Glu Leu Val Val Asn Ser Asp Lys Thr Ile Asp Gly Arg Gly Val
1               5                   10                  15

Lys Val Glu Ile Ile
            20

<210> SEQ ID NO 37
<211> LENGTH: 18
<212> TYPE: PRT
<213> ORGANISM: Ambrosia artemisiifolia

<400> SEQUENCE: 37

Gly Glu Ala Ala Ile Lys Leu Thr Ser Ser Ala Gly Val Phe Ser Cys His Pro
1               5                   10                  15

<210> SEQ ID NO 38
<211> LENGTH: 18
<212> TYPE: PRT
<213> ORGANISM: Ambrosia artemisiifolia

<400> SEQUENCE: 38

Phe Gly Phe Phe Gln Val Val Asn Asn Asn Tyr Asp Arg Trp Gly Thr Tyr Ala
1               5                   10                  15

<210> SEQ ID NO 39
<211> LENGTH: 12
<212> TYPE: PRT
<213> ORGANISM: Ambrosia artemisiifolia

<400> SEQUENCE: 39

Glu Thr Arg Ser Leu Gln Ala Cys Glu Ala Leu Asn
1               5                   10

<210> SEQ ID NO 40
<211> LENGTH: 18
<212> TYPE: PRT
<213> ORGANISM: Ambrosia artemisiifolia

<400> SEQUENCE: 40

Gly Glu Ala Ala Ile Lys Leu Thr Ser Ser Ala Gly Val Leu Ser Cys
1               5                   10                  15

Arg Pro

<210> SEQ ID NO 41
<211> LENGTH: 17
<212> TYPE: PRT
<213> ORGANISM: Ambrosia artemisiifolia

<400> SEQUENCE: 41

His Gly Phe Phe Gln Val Val Asn Asn Asn Tyr Asp Arg Gly Thr Tyr
1               5                   10                  15
```

Ala

<210> SEQ ID NO 42
<211> LENGTH: 12
<212> TYPE: PRT
<213> ORGANISM: Ambrosia artemisiifolia

<400> SEQUENCE: 42

```
Glu Thr Arg Arg Leu Thr Thr Ser Gly Ala Tyr Asn
1               5                   10
```

<210> SEQ ID NO 43
<211> LENGTH: 396
<212> TYPE: PRT
<213> ORGANISM: Ambrosia artemisiifolia

<400> SEQUENCE: 43

```
Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
            20                  25                  30

Leu Pro Val Asn Glu Thr Arg Arg Leu Thr Thr Ser Gly Ala Tyr Asn
        35                  40                  45

Ile Ile Asp Gly Cys Trp Arg Gly Lys Ala Asp Trp Ala Glu Asn Arg
    50                  55                  60

Lys Ala Leu Ala Asp Cys Ala Gln Gly Phe Gly Lys Gly Thr Val Gly
65                  70                  75                  80

Gly Lys Asp Gly Asp Ile Tyr Thr Val Thr Ser Glu Leu Asp Asp
                85                  90                  95

Val Ala Asn Pro Lys Glu Gly Thr Leu Arg Phe Gly Ala Ala Gln Asn
            100                 105                 110

Arg Pro Leu Trp Ile Ile Phe Glu Arg Asp Met Val Ile Arg Leu Asp
        115                 120                 125

Lys Glu Met Val Val Asn Ser Asp Lys Thr Ile Asp Gly Arg Gly Ala
    130                 135                 140

Lys Val Glu Ile Ile Asn Ala Gly Phe Thr Leu Asn Gly Val Lys Asn
145                 150                 155                 160

Val Ile Ile His Asn Ile Asn Met His Asp Val Lys Val Asn Pro Gly
                165                 170                 175

Gly Leu Ile Lys Ser Asn Asp Gly Pro Ala Ala Pro Arg Ala Gly Ser
            180                 185                 190

Asp Gly Asp Ala Ile Ser Ile Ser Gly Ser Ser Gln Ile Trp Ile Asp
        195                 200                 205

His Cys Ser Leu Ser Lys Ser Val Asp Gly Leu Val Asp Ala Lys Leu
    210                 215                 220

Gly Thr Thr Arg Leu Thr Val Ser Asn Ser Leu Phe Thr Gln His Gln
225                 230                 235                 240

Phe Val Leu Leu Phe Gly Ala Gly Asp Glu Asn Ile Glu Asp Arg Gly
                245                 250                 255

Met Leu Ala Thr Val Ala Phe Asn Thr Phe Thr Asp Asn Val Asp Gln
            260                 265                 270

Arg Met Pro Arg Cys Arg His Gly Phe Phe Gln Val Val Asn Asn Asn
        275                 280                 285

Tyr Asp Lys Trp Gly Ser Tyr Ala Ile Gly Gly Ser Ala Ser Pro Thr
    290                 295                 300

Ile Leu Ser Gln Gly Asn Arg Phe Cys Ala Pro Asp Glu Arg Ser Lys
```

```
            305                 310                 315                 320
Lys Asn Val Leu Gly Arg His Gly Glu Ala Ala Glu Ser Met Lys
                325                 330                 335

Trp Asn Trp Arg Thr Asn Lys Asp Val Leu Glu Asn Gly Ala Ile Phe
                340                 345                 350

Val Ala Ser Gly Val Asp Pro Val Leu Thr Pro Glu Ser Ala Gly
                355                 360                 365

Met Ile Pro Ala Glu Pro Gly Glu Ser Ala Leu Ser Leu Thr Ser Ser
370                 375                 380

Ala Gly Val Leu Ser Cys Gln Pro Gly Ala Pro Cys
385                 390                 395

<210> SEQ ID NO 44
<211> LENGTH: 398
<212> TYPE: PRT
<213> ORGANISM: Ambrosia artemisiifolia

<400> SEQUENCE: 44

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Val Glu Glu Phe
                20                  25                  30

Leu Pro Ser Ala Asn Glu Thr Arg Arg Ser Leu Lys Ala Cys Glu Ala
            35                  40                  45

His Asn Ile Ile Asp Lys Cys Trp Arg Cys Lys Ala Asp Trp Ala Asn
        50                  55                  60

Asn Arg Gln Ala Leu Ala Asp Cys Ala Gln Gly Phe Ala Lys Gly Thr
65                  70                  75                  80

Tyr Gly Gly Lys His Gly Asp Val Tyr Thr Val Thr Ser Asp Lys Asp
                85                  90                  95

Asp Asp Val Ala Asn Pro Lys Glu Gly Thr Leu Arg Phe Ala Ala Ala
            100                 105                 110

Gln Asn Arg Pro Leu Trp Ile Ile Phe Lys Arg Asn Met Val Ile His
        115                 120                 125

Leu Asn Gln Glu Leu Val Val Asn Ser Asp Lys Thr Ile Asp Gly Arg
    130                 135                 140

Gly Val Lys Val Asn Ile Val Asn Ala Gly Leu Thr Leu Met Asn Val
145                 150                 155                 160

Lys Asn Ile Ile Ile His Asn Ile Asn Ile His Asp Ile Lys Val Cys
                165                 170                 175

Pro Gly Gly Met Ile Lys Ser Asn Asp Gly Pro Pro Ile Leu Arg Gln
            180                 185                 190

Gln Ser Asp Gly Asp Ala Ile Asn Val Ala Gly Ser Ser Gln Ile Trp
        195                 200                 205

Ile Asp His Cys Ser Leu Ser Lys Ala Ser Asp Gly Leu Leu Asp Ile
    210                 215                 220

Thr Leu Gly Ser Ser His Val Thr Val Ser Asn Cys Lys Phe Thr Gln
225                 230                 235                 240

His Gln Phe Val Leu Leu Leu Gly Ala Asp Asp Thr His Tyr Gln Asp
                245                 250                 255

Lys Gly Met Leu Ala Thr Val Ala Phe Asn Met Phe Thr Asp His Val
            260                 265                 270

Asp Gln Arg Met Pro Arg Cys Arg Phe Gly Phe Phe Gln Val Val Asn
        275                 280                 285
```

```
Asn Asn Tyr Asp Arg Trp Gly Thr Tyr Ala Ile Gly Gly Ser Ser Ala
    290                 295                 300
Pro Thr Ile Leu Ser Gln Gly Asn Arg Phe Phe Ala Pro Asp Asp Ile
305                 310                 315                 320
Ile Lys Lys Asn Val Leu Ala Arg Thr Gly Thr Gly Asn Ala Glu Ser
                325                 330                 335
Met Ser Trp Asn Trp Arg Thr Asp Arg Asp Leu Leu Glu Asn Gly Ala
            340                 345                 350
Ile Phe Leu Pro Ser Gly Ser Asp Pro Val Leu Thr Pro Glu Gln Lys
        355                 360                 365
Ala Gly Met Ile Pro Ala Glu Pro Gly Glu Ala Val Leu Arg Leu Thr
370                 375                 380
Ser Ser Ala Gly Val Leu Ser Cys His Gln Gly Ala Pro Cys
385                 390                 395

<210> SEQ ID NO 45
<211> LENGTH: 397
<212> TYPE: PRT
<213> ORGANISM: Ambrosia artemisiifolia

<400> SEQUENCE: 45

Met Gly Ile Lys Gln Cys Cys Tyr Ile Leu Tyr Phe Thr Leu Ala Leu
1               5                   10                  15
Val Ala Leu Leu Gln Pro Val Arg Ser Ala Glu Gly Val Gly Glu Ile
            20                  25                  30
Leu Pro Ser Val Asn Glu Thr Arg Ser Leu Gln Ala Cys Glu Ala Leu
        35                  40                  45
Asn Ile Ile Asp Lys Cys Trp Arg Gly Lys Ala Asp Trp Glu Asn Asn
    50                  55                  60
Arg Gln Ala Leu Ala Asp Cys Ala Gln Gly Phe Ala Lys Gly Thr Tyr
65                  70                  75                  80
Gly Gly Lys Trp Gly Asp Val Tyr Thr Val Thr Ser Asn Leu Asp Asp
                85                  90                  95
Asp Val Ala Asn Pro Lys Glu Gly Thr Leu Arg Phe Ala Ala Ala Gln
            100                 105                 110
Asn Arg Pro Leu Trp Ile Ile Phe Lys Asn Asp Met Val Ile Asn Leu
        115                 120                 125
Asn Gln Glu Leu Val Val Asn Ser Asp Lys Thr Ile Asp Gly Arg Gly
    130                 135                 140
Val Lys Val Glu Ile Ile Asn Gly Gly Leu Thr Leu Met Asn Val Lys
145                 150                 155                 160
Asn Ile Ile Ile His Asn Ile Asn Ile His Asp Val Lys Val Leu Pro
                165                 170                 175
Gly Gly Met Ile Lys Ser Asn Asp Gly Pro Pro Ile Leu Arg Gln Ala
            180                 185                 190
Ser Asp Gly Asp Thr Ile Asn Val Ala Gly Ser Ser Gln Ile Trp Ile
        195                 200                 205
Asp His Cys Ser Leu Ser Lys Ser Phe Asp Gly Leu Val Asp Val Thr
    210                 215                 220
Leu Gly Ser Thr His Val Thr Ile Ser Asn Cys Lys Phe Thr Gln Gln
225                 230                 235                 240
Ser Lys Ala Ile Leu Leu Gly Ala Asp Asp Thr His Val Gln Asp Lys
                245                 250                 255
Gly Met Leu Ala Thr Val Ala Phe Asn Met Phe Thr Asp Asn Val Asp
            260                 265                 270
```

```
Gln Arg Met Pro Arg Cys Arg Phe Gly Phe Gln Val Val Asn Asn
            275                 280                 285

Asn Tyr Asp Arg Trp Gly Thr Tyr Ala Ile Gly Gly Ser Ser Ala Pro
290                 295                 300

Thr Ile Leu Cys Gln Gly Asn Arg Phe Leu Ala Pro Asp Asp Gln Ile
305                 310                 315                 320

Lys Lys Asn Val Leu Ala Arg Thr Gly Thr Gly Ala Ala Glu Ser Met
            325                 330                 335

Ala Trp Asn Trp Arg Ser Asp Lys Asp Leu Leu Glu Asn Gly Ala Ile
            340                 345                 350

Phe Val Thr Ser Gly Ser Asp Pro Val Leu Thr Pro Val Gln Ser Ala
            355                 360                 365

Gly Met Ile Pro Ala Glu Pro Gly Glu Ala Ala Ile Lys Leu Thr Ser
            370                 375                 380

Ser Ala Gly Val Phe Ser Cys His Pro Gly Ala Pro Cys
385                 390                 395

<210> SEQ ID NO 46
<211> LENGTH: 392
<212> TYPE: PRT
<213> ORGANISM: Ambrosia artemisiifolia

<400> SEQUENCE: 46

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Gln Ile
            20                  25                  30

Leu Pro Ser Ala Asn Glu Thr Arg Ser Leu Thr Thr Cys Gly Thr Tyr
            35                  40                  45

Asn Ile Ile Asp Gly Cys Trp Arg Gly Lys Ala Asp Trp Ala Glu Asn
50                  55                  60

Arg Lys Ala Leu Ala Asp Cys Ala Gln Gly Phe Ala Lys Gly Thr Ile
65                  70                  75                  80

Gly Gly Lys Asp Gly Asp Ile Tyr Thr Val Thr Ser Glu Leu Asp Asp
            85                  90                  95

Asp Val Ala Asn Pro Lys Glu Gly Thr Leu Arg Phe Gly Ala Ala Gln
            100                 105                 110

Asn Arg Pro Leu Trp Ile Ile Phe Ala Arg Asp Met Val Ile Arg Leu
            115                 120                 125

Asp Arg Glu Leu Ala Ile Asn Asn Asp Lys Thr Ile Asp Gly Arg Gly
            130                 135                 140

Ala Lys Val Glu Ile Ile Asn Ala Gly Phe Ala Ile Tyr Asn Val Lys
145                 150                 155                 160

Asn Ile Ile Ile His Asn Ile Ile Met His Asp Ile Val Asn Pro
            165                 170                 175

Gly Gly Leu Ile Lys Ser His Asp Gly Pro Pro Val Pro Arg Lys Gly
            180                 185                 190

Ser Asp Gly Asp Ala Ile Gly Ile Ser Gly Gly Ser Gln Ile Trp Ile
            195                 200                 205

Asp His Cys Ser Leu Ser Lys Ala Val Asp Gly Leu Ile Asp Ala Lys
            210                 215                 220

His Gly Ser Thr His Phe Thr Val Ser Asn Cys Leu Phe Thr Gln His
225                 230                 235                 240

Gln Tyr Leu Leu Leu Phe Trp Asp Phe Asp Glu Arg Gly Met Leu Cys
```

```
                    245                 250                 255
Thr Val Ala Phe Asn Lys Phe Thr Asp Asn Val Asp Gln Arg Met Pro
                260                 265                 270

Asn Leu Arg His Gly Phe Val Gln Val Asn Asn Asn Tyr Glu Arg
            275                 280                 285

Trp Gly Ser Tyr Ala Leu Gly Ser Ala Gly Pro Thr Ile Leu Ser
        290                 295                 300

Gln Gly Asn Arg Phe Leu Ala Ser Asp Ile Lys Lys Glu Val Val Gly
305                 310                 315                 320

Arg Tyr Gly Glu Ser Ala Met Ser Glu Ser Ile Asn Trp Asn Trp Arg
                325                 330                 335

Ser Tyr Met Asp Val Phe Glu Asn Gly Ala Ile Phe Val Pro Ser Gly
                340                 345                 350

Val Asp Pro Val Leu Thr Pro Glu Gln Asn Ala Gly Met Ile Pro Ala
                355                 360                 365

Glu Pro Gly Glu Ala Val Leu Arg Leu Thr Ser Ser Ala Gly Val Leu
            370                 375                 380

Ser Cys Gln Pro Gly Ala Pro Cys
385                 390

<210> SEQ ID NO 47
<211> LENGTH: 320
<212> TYPE: PRT
<213> ORGANISM: Dermatophagoides pteronyssinus

<400> SEQUENCE: 47

Met Lys Ile Val Leu Ala Ile Ala Ser Leu Leu Ala Leu Ser Ala Val
1               5                   10                  15

Tyr Ala Arg Pro Ser Ser Ile Lys Thr Phe Glu Glu Tyr Lys Lys Ala
                20                  25                  30

Phe Asn Lys Ser Tyr Ala Thr Phe Glu Asp Glu Glu Ala Ala Arg Lys
            35                  40                  45

Asn Phe Leu Glu Ser Val Lys Tyr Val Gln Ser Asn Gly Gly Ala Ile
        50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Cys Trp Ala Phe Ser Gly Val Ala Ala Thr Glu Ser Ala
    130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
    210                 215                 220
```

```
Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
            260                 265                 270

Val Gly Tyr Ser Asn Ala Gln Gly Val Asp Tyr Trp Ile Val Arg Asn
        275                 280                 285

Ser Trp Asp Thr Asn Trp Gly Asp Asn Gly Tyr Gly Tyr Phe Ala Ala
    290                 295                 300

Asn Ile Asp Leu Met Met Ile Glu Glu Tyr Pro Tyr Val Val Ile Leu
305                 310                 315                 320

<210> SEQ ID NO 48
<211> LENGTH: 146
<212> TYPE: PRT
<213> ORGANISM: Dermatophagoides pteronyssinus

<400> SEQUENCE: 48

Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
                20                  25                  30

Val Leu Val Pro Gly Cys His Gly Ser Glu Pro Cys Ile Ile His Arg
            35                  40                  45

Gly Lys Pro Phe Gln Leu Glu Ala Val Phe Glu Ala Asn Gln Asn Thr
        50                  55                  60

Lys Thr Ala Lys Ile Glu Ile Lys Ala Ser Ile Asp Gly Leu Glu Val
65                  70                  75                  80

Asp Val Pro Gly Ile Asp Pro Asn Ala Cys His Tyr Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Val Met
        115                 120                 125

Gly Asp Asp Gly Val Leu Ala Cys Ala Ile Ala Thr His Ala Lys Ile
    130                 135                 140

Arg Asp
145

<210> SEQ ID NO 49
<211> LENGTH: 261
<212> TYPE: PRT
<213> ORGANISM: Dermatophagoides pteronyssinus

<400> SEQUENCE: 49

Met Ile Ile Tyr Asn Ile Leu Ile Val Leu Leu Leu Ala Ile Asn Thr
1               5                   10                  15

Leu Ala Asn Pro Ile Leu Pro Ala Ser Pro Asn Ala Thr Ile Val Gly
                20                  25                  30

Gly Glu Lys Ala Leu Ala Gly Glu Cys Pro Tyr Gln Ile Ser Leu Gln
            35                  40                  45

Ser Ser Ser His Phe Cys Gly Gly Thr Ile Leu Asp Glu Tyr Trp Ile
        50                  55                  60

Leu Thr Ala Ala His Cys Val Ala Gly Gln Thr Ala Ser Lys Leu Ser
65                  70                  75                  80
```

```
Ile Arg Tyr Asn Ser Leu Lys His Ser Leu Gly Gly Glu Lys Ile Ser
                85                  90                  95

Val Ala Lys Ile Phe Ala His Glu Lys Tyr Asp Ser Tyr Gln Ile Asp
            100                 105                 110

Asn Asp Ile Ala Leu Ile Lys Leu Lys Ser Pro Met Lys Leu Asn Gln
        115                 120                 125

Lys Asn Ala Lys Ala Val Gly Leu Pro Ala Lys Gly Ser Asp Val Lys
130                 135                 140

Val Gly Asp Gln Val Arg Val Ser Gly Trp Gly Tyr Leu Glu Glu Gly
145                 150                 155                 160

Ser Tyr Ser Leu Pro Ser Glu Leu Arg Arg Val Asp Ile Ala Val Val
                165                 170                 175

Ser Arg Lys Glu Cys Asn Glu Leu Tyr Ser Lys Ala Asn Ala Glu Val
            180                 185                 190

Thr Asp Asn Met Ile Cys Gly Gly Asp Val Ala Asn Gly Gly Lys Asp
        195                 200                 205

Ser Cys Gln Gly Asp Ser Gly Gly Pro Val Val Asp Val Lys Asn Asn
    210                 215                 220

Gln Val Val Gly Ile Val Ser Trp Gly Tyr Gly Cys Ala Arg Lys Gly
225                 230                 235                 240

Tyr Pro Gly Val Tyr Thr Arg Val Gly Asn Phe Ile Asp Trp Ile Glu
                245                 250                 255

Ser Lys Arg Ser Gln
            260

<210> SEQ ID NO 50
<211> LENGTH: 19
<212> TYPE: PRT
<213> ORGANISM: Dermatophagoides pteronyssinus
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = any amino acid

<400> SEQUENCE: 50

Lys Tyr Xaa Asn Pro His Phe Ile Gly Xaa Arg Ser Val Ile Thr Xaa
1               5                   10                  15

Leu Met Glu

<210> SEQ ID NO 51
<211> LENGTH: 132
<212> TYPE: PRT
<213> ORGANISM: Dermatophagoides pteronyssinus

<400> SEQUENCE: 51

Met Lys Phe Ile Ile Ala Phe Phe Val Ala Thr Leu Ala Val Met Thr
1               5                   10                  15

Val Ser Gly Glu Asp Lys Lys His Asp Tyr Gln Asn Glu Phe Asp Phe
                20                  25                  30

Leu Leu Met Glu Arg Ile His Glu Gln Ile Lys Lys Gly Glu Leu Ala
            35                  40                  45

Leu Phe Tyr Leu Gln Glu Gln Ile Asn His Phe Glu Glu Lys Pro Thr
```

```
            50                  55                  60

Lys Glu Met Lys Asp Lys Ile Val Ala Glu Met Asp Thr Ile Ile Ala
 65                  70                  75                  80

Met Ile Asp Gly Val Arg Gly Val Leu Asp Arg Leu Met Gln Arg Lys
                 85                  90                  95

Asp Leu Asp Ile Phe Glu Gln Tyr Asn Leu Met Ala Lys Lys Ser
            100                 105                 110

Gly Asp Ile Leu Glu Arg Asp Leu Lys Lys Glu Ala Arg Val Lys
        115                 120                 125

Lys Ile Glu Val
        130

<210> SEQ ID NO 52
<211> LENGTH: 20
<212> TYPE: PRT
<213> ORGANISM: Dermatophagoides pteronyssinus
<220> FEATURE:
<221> NAME/KEY: MISC_FEATURE
<222> LOCATION: (4)..(4)
<223> OTHER INFORMATION: Xaa = any amino acid

<400> SEQUENCE: 52

Ala Ile Gly Xaa Gln Pro Ala Ala Glu Ala Glu Ala Pro Phe Gln Ile
 1               5                  10                  15

Ser Leu Met Lys
            20

<210> SEQ ID NO 53
<211> LENGTH: 215
<212> TYPE: PRT
<213> ORGANISM: Dermatophagoides pteronyssinus

<400> SEQUENCE: 53

Met Met Lys Leu Leu Leu Ile Ala Ala Ala Ala Phe Val Ala Val Ser
 1               5                  10                  15

Ala Asp Pro Ile His Tyr Asp Lys Ile Thr Glu Glu Ile Asn Lys Ala
            20                  25                  30

Val Asp Glu Ala Val Ala Ala Ile Glu Lys Ser Glu Thr Phe Asp Pro
        35                  40                  45

Met Lys Val Pro Asp His Ser Asp Lys Phe Glu Arg His Ile Gly Ile
    50                  55                  60

Ile Asp Leu Lys Gly Glu Leu Asp Met Arg Asn Ile Gln Val Arg Gly
 65                  70                  75                  80

Leu Lys Gln Met Lys Arg Val Gly Asp Ala Asn Val Lys Ser Glu Asp
                 85                  90                  95

Gly Val Val Lys Ala His Leu Leu Val Gly Val His Asp Asp Val Val
            100                 105                 110

Ser Met Glu Tyr Asp Leu Ala Tyr Lys Leu Gly Asp Leu His Pro Asn
        115                 120                 125

Thr His Val Ile Ser Asp Ile Gln Asp Phe Val Val Glu Leu Ser Leu
    130                 135                 140

Glu Val Ser Glu Glu Gly Asn Met Thr Leu Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Ala Val Leu Ser Asp Val Leu Thr Ala Ile Phe Gln Asp
            180                 185                 190
```

```
Thr Val Arg Ala Glu Met Thr Lys Val Leu Ala Pro Ala Phe Lys Lys
            195                 200                 205

Glu Leu Glu Arg Asn Asn Gln
        210                 215

<210> SEQ ID NO 54
<211> LENGTH: 18
<212> TYPE: PRT
<213> ORGANISM: Dermatophagoides pteronyssinus

<400> SEQUENCE: 54

Ile Val Gly Gly Ser Asn Ala Ser Pro Gly Asp Ala Val Tyr Gln Ile
1               5                   10                  15

Ala Leu

<210> SEQ ID NO 55
<211> LENGTH: 319
<212> TYPE: PRT
<213> ORGANISM: Dermatophagoides farinae

<400> SEQUENCE: 55

Met Lys Phe Val Leu Ala Ile Ala Ser Leu Leu Val Leu Thr Val Tyr
1               5                   10                  15

Ala Arg Pro Ala Ser Ile Lys Thr Phe Glu Phe Lys Lys Ala Phe Asn
            20                  25                  30

Lys Asn Tyr Ala Thr Val Glu Glu Glu Val Ala Arg Lys Asn Phe
        35                  40                  45

Leu Glu Ser Leu Lys Tyr Val Glu Ala Asn Lys Gly Ala Ile Asn His
    50                  55                  60

Leu Ser Asp Leu Ser Leu Asp Glu Phe Lys Asn Arg Tyr Leu Met Ser
65                  70                  75                  80

Ala Glu Ala Phe Glu Gln Leu Lys Thr Gln Phe Asp Leu Asn Ala Glu
                85                  90                  95

Thr Ser Ala Cys Arg Ile Asn Ser Val Asn Val Pro Ser Glu Leu Asp
            100                 105                 110

Leu Arg Ser Leu Arg Thr Val Thr Pro Ile Arg Met Gln Gly Gly Cys
        115                 120                 125

Gly Ser Cys Trp Ala Phe Ser Gly Val Ala Ala Thr Glu Ser Ala Tyr
    130                 135                 140

Leu Ala Tyr Arg Asn Thr Ser Leu Asp Leu Ser Glu Gln Glu Leu Val
145                 150                 155                 160

Asp Cys Ala Ser Gln His Gly Cys His Gly Asp Thr Ile Pro Arg Gly
                165                 170                 175

Ile Glu Tyr Ile Gln Gln Asn Gly Val Val Glu Glu Arg Ser Tyr Pro
            180                 185                 190

Tyr Val Ala Arg Glu Gln Arg Cys Arg Arg Pro Asn Ser Gln His Tyr
        195                 200                 205

Gly Ile Ser Asn Tyr Cys Gln Ile Tyr Pro Pro Asp Val Lys Gln Ile
    210                 215                 220

Arg Glu Ala Leu Thr Gln Thr His Thr Ala Ile Ala Val Ile Ile Gly
225                 230                 235                 240

Ile Lys Asp Leu Arg Ala Phe Gln His Tyr Asp Gly Arg Thr Ile Ile
                245                 250                 255

Gln His Asp Asn Gly Tyr Gln Pro Asn Tyr His Ala Val Asn Ile Val
            260                 265                 270

Gly Tyr Gly Ser Thr Gln Gly Asp Asp Tyr Trp Ile Val Arg Asn Ser
```

```
                    275                 280                 285
Trp Asp Thr Thr Trp Gly Asp Ser Gly Tyr Gly Tyr Phe Gln Ala Gly
    290                 295                 300

Asn Asn Leu Met Met Ile Glu Gln Tyr Pro Tyr Val Val Ile Met
305                 310                 315
```

<210> SEQ ID NO 56
<211> LENGTH: 146
<212> TYPE: PRT
<213> ORGANISM: Dermatophagoides farinae

<400> SEQUENCE: 56

```
Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
    50                  55                  60

Lys Thr Ala Lys Ile Glu Ile Lys Ala Ser Leu Asp Gly Leu Glu Ile
65                  70                  75                  80

Asp Val Pro Gly Ile Asp Thr Asn Ala Cys His Phe Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Leu Ile
        115                 120                 125

Gly Asp Asn Gly Val Leu Ala Cys Ala Ile Ala Thr His Gly Lys Ile
    130                 135                 140

Arg Asp
145
```

<210> SEQ ID NO 57
<211> LENGTH: 259
<212> TYPE: PRT
<213> ORGANISM: Dermatophagoides farinae

<400> SEQUENCE: 57

```
Met Met Ile Leu Thr Ile Val Val Leu Leu Ala Ala Asn Ile Leu Ala
1               5                   10                  15

Thr Pro Ile Leu Pro Ser Ser Pro Asn Ala Thr Ile Val Gly Gly Val
            20                  25                  30

Lys Ala Gln Ala Gly Asp Cys Pro Tyr Gln Ile Ser Leu Gln Ser Ser
        35                  40                  45

Ser His Phe Cys Gly Gly Ser Ile Leu Asp Glu Tyr Trp Ile Leu Thr
    50                  55                  60

Ala Ala His Cys Val Asn Gly Gln Ser Ala Lys Lys Leu Ser Ile Arg
65                  70                  75                  80

Tyr Asn Thr Leu Lys His Ala Ser Gly Gly Glu Lys Ile Gln Val Ala
                85                  90                  95

Glu Ile Tyr Gln His Glu Asn Tyr Asp Ser Met Thr Ile Asp Asn Asp
            100                 105                 110

Val Ala Leu Ile Lys Leu Lys Thr Pro Met Thr Leu Asp Gln Thr Asn
        115                 120                 125

Ala Lys Pro Val Pro Leu Pro Ala Gln Gly Ser Asp Val Lys Val Gly
```

```
                    130                 135                 140
Asp Lys Ile Arg Val Ser Gly Trp Gly Tyr Leu Gln Glu Gly Ser Tyr
145                 150                 155                 160

Ser Leu Pro Ser Glu Leu Gln Arg Val Asp Ile Asp Val Val Ser Arg
                    165                 170                 175

Glu Gln Cys Asp Gln Leu Tyr Ser Lys Ala Gly Ala Asp Val Ser Glu
                180                 185                 190

Asn Met Ile Cys Gly Gly Asp Val Ala Asn Gly Val Asp Ser Cys
                195                 200                 205

Gln Gly Asp Ser Gly Gly Pro Val Val Asp Val Ala Thr Lys Gln Ile
            210                 215                 220

Val Gly Ile Val Ser Trp Gly Tyr Gly Cys Ala Arg Lys Gly Tyr Pro
225                 230                 235                 240

Gly Val Tyr Thr Arg Val Gly Asn Phe Val Asp Trp Ile Glu Ser Lys
                245                 250                 255

Arg Ser Gln
```

<210> SEQ ID NO 58
<211> LENGTH: 20
<212> TYPE: PRT
<213> ORGANISM: Dermatophagoides farinae

<400> SEQUENCE: 58

```
Ala Val Gly Gly Gln Asp Ala Asp Leu Ala Glu Ala Pro Phe Gln Ile
1               5                   10                  15

Ser Leu Leu Lys
            20
```

<210> SEQ ID NO 59
<211> LENGTH: 213
<212> TYPE: PRT
<213> ORGANISM: Dermatophagoides farinae

<400> SEQUENCE: 59

```
Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
                20                  25                  30

Ile Asp Asp Ala Ile Ala Ala Ile Glu Gln Ser Glu Thr Ile Asp Pro
            35                  40                  45

Met Lys Val Pro Asp His Ala Asp Lys Phe Glu Arg His Val Gly Ile
        50                  55                  60

Val Asp Phe Lys Gly Glu Leu Ala Met Arg Asn Ile Glu Ala Arg Gly
65                  70                  75                  80

Leu Lys Gln Met Lys Arg Gln Gly Asp Ala Asn Val Lys Gly Glu Glu
                85                  90                  95

Gly Ile Val Lys Ala His Leu Leu Ile Gly Val His Asp Asp Ile Val
            100                 105                 110

Ser Met Glu Tyr Asp Leu Ala Tyr Lys Leu Gly Asp Leu His Pro Thr
        115                 120                 125

Thr His Val Ile Ser Asp Ile Gln Asp Phe Val Val Ala Leu Ser Leu
    130                 135                 140

Glu Ile Ser Asp Glu Gly Asn Ile Thr Met Thr Ser Phe Glu Val Arg
145                 150                 155                 160

Gln Phe Ala Asn Val Val Asn His Ile Gly Gly Leu Ser Ile Leu Asp
                165                 170                 175
```

```
Pro Ile Phe Gly Val Leu Ser Asp Val Leu Thr Ala Ile Phe Gln Asp
            180                 185                 190

Thr Val Arg Lys Glu Met Thr Lys Val Leu Ala Pro Ala Phe Lys Arg
        195                 200                 205

Glu Leu Glu Lys Asn
        210

<210> SEQ ID NO 60
<211> LENGTH: 138
<212> TYPE: PRT
<213> ORGANISM: Hevea brasiliensis

<400> SEQUENCE: 60

Met Ala Glu Asp Glu Asn Gln Gln Gly Gln Gly Glu Gly Leu Lys
1               5                   10                  15

Tyr Leu Gly Phe Val Gln Asp Ala Ala Thr Tyr Ala Val Thr Thr Phe
            20                  25                  30

Ser Asn Val Tyr Leu Phe Ala Lys Asp Lys Ser Gly Pro Leu Gln Pro
        35                  40                  45

Gly Val Asp Ile Ile Glu Gly Pro Val Lys Asn Val Ala Val Pro Leu
    50                  55                  60

Tyr Asn Arg Phe Ser Tyr Ile Pro Asn Gly Ala Leu Lys Phe Val Asp
65                  70                  75                  80

Ser Thr Val Val Ala Ser Val Thr Ile Ile Asp Arg Ser Leu Pro Pro
                85                  90                  95

Ile Val Lys Asp Ala Ser Ile Gln Val Val Ser Ala Ile Arg Ala Ala
            100                 105                 110

Pro Glu Ala Ala Arg Ser Leu Ala Ser Ser Leu Pro Gly Gln Thr Lys
        115                 120                 125

Ile Leu Ala Lys Val Phe Tyr Gly Glu Asn
    130                 135

<210> SEQ ID NO 61
<211> LENGTH: 204
<212> TYPE: PRT
<213> ORGANISM: Hevea brasiliensis

<400> SEQUENCE: 61

Met Ala Glu Glu Val Glu Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
            20                  25                  30

Tyr Ala Lys Asp Ile Ser Gly Pro Leu Lys Pro Gly Val Asp Thr Ile
        35                  40                  45

Glu Asn Val Val Lys Thr Val Thr Pro Val Tyr Tyr Ile Pro Leu
    50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
            100                 105                 110

Ser Val Phe Asn Thr Gly Val Gln Glu Gly Ala Lys Ala Leu Tyr Ala
        115                 120                 125

Asn Leu Glu Pro Lys Ala Glu Gln Tyr Ala Val Ile Thr Trp Arg Ala
    130                 135                 140
```

```
Leu Asn Lys Leu Pro Leu Val Pro Gln Val Ala Asn Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
        195                 200
```

<210> SEQ ID NO 62
<211> LENGTH: 263
<212> TYPE: PRT
<213> ORGANISM: Lolium perenne

<400> SEQUENCE: 62

```
Met Ala Ser Ser Ser Val Leu Leu Val Ala Leu Phe Ala Val
1               5                   10                  15

Phe Leu Gly Ser Ala His Gly Ile Ala Lys Val Pro Pro Gly Pro Asn
                20                  25                  30

Ile Thr Ala Glu Tyr Gly Asp Lys Trp Leu Asp Ala Lys Ser Thr Trp
            35                  40                  45

Tyr Gly Lys Pro Thr Gly Ala Gly Pro Lys Asp Asn Gly Gly Ala Cys
50                  55                  60

Gly Tyr Lys Asn Val Asp Lys Ala Pro Phe Asn Gly Met Thr Gly Cys
65                  70                  75                  80

Gly Asn Thr Pro Ile Phe Lys Asp Gly Arg Gly Cys Gly Ser Cys Phe
                85                  90                  95

Glu Ile Lys Cys Thr Lys Pro Glu Ser Cys Ser Gly Glu Ala Val Thr
            100                 105                 110

Val Thr Ile Thr Asp Asp Asn Glu Glu Pro Ile Ala Pro Tyr His Phe
        115                 120                 125

Asp Leu Ser Gly His Ala Phe Gly Ser Met Ala Lys Lys Gly Glu Glu
    130                 135                 140

Gln Asn Val Arg Ser Ala Gly Glu Leu Glu Leu Gln Phe Arg Arg Val
145                 150                 155                 160

Lys Cys Lys Tyr Pro Asp Asp Thr Lys Pro Thr Phe His Val Glu Lys
                165                 170                 175

Ala Ser Asn Pro Asn Tyr Leu Ala Ile Leu Val Lys Tyr Val Asp Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Val Trp Arg Ile Asp Thr
    210                 215                 220

Pro Asp Lys Leu Thr Gly Pro Phe Thr Val Arg Tyr Thr Thr Glu Gly
225                 230                 235                 240

Gly Thr Lys Ser Glu Phe Glu Asp Val Ile Pro Glu Gly Trp Lys Ala
                245                 250                 255

Asp Thr Ser Tyr Ser Ala Lys
            260
```

<210> SEQ ID NO 63
<211> LENGTH: 97
<212> TYPE: PRT
<213> ORGANISM: Lolium perenne

<400> SEQUENCE: 63

-continued

Ala Ala Pro Val Glu Phe Thr Val Glu Lys Gly Ser Asp Glu Lys Asn
1               5                   10                  15

Leu Ala Leu Ser Ile Lys Tyr Asn Lys Glu Gly Asp Ser Met Ala Glu
                20                  25                  30

Val Glu Leu Lys Glu His Gly Ser Asn Glu Trp Leu Ala Leu Lys Lys
            35                  40                  45

Asn Gly Asp Gly Val Trp Glu Ile Lys Ser Asp Lys Pro Leu Lys Gly
        50                  55                  60

Pro Phe Asn Phe Arg Phe Val Ser Glu Lys Gly Met Arg Asn Val Phe
65              70                  75                  80

Asp Asp Val Val Pro Ala Asp Phe Lys Val Gly Thr Thr Tyr Lys Pro
                85                  90                  95

Glu

<210> SEQ ID NO 64
<211> LENGTH: 97
<212> TYPE: PRT
<213> ORGANISM: Lolium perenne

<400> SEQUENCE: 64

Thr Lys Val Asp Leu Thr Val Glu Lys Gly Ser Asp Ala Lys Thr Leu
1               5                   10                  15

Val Leu Asn Ile Lys Tyr Thr Arg Pro Gly Asp Thr Leu Ala Glu Val
                20                  25                  30

Glu Leu Arg Gln His Gly Ser Glu Gly Trp Glu Pro Met Thr Lys Lys
            35                  40                  45

Gly Asn Leu Trp Glu Val Lys Ser Ala Lys Pro Leu Thr Gly Pro Met
        50                  55                  60

Asn Phe Arg Phe Leu Ser Lys Gly Gly Met Lys Asn Val Phe Asp Glu
65              70                  75                  80

Val Ile Pro Thr Ala Phe Thr Val Gly Lys Thr Tyr Thr Pro Glu Tyr
                85                  90                  95

Asn

<210> SEQ ID NO 65
<211> LENGTH: 308
<212> TYPE: PRT
<213> ORGANISM: Lolium perenne

<400> SEQUENCE: 65

Met Ala Val Gln Lys Tyr Thr Val Ala Leu Phe Leu Arg Arg Gly Pro
1               5                   10                  15

Arg Gly Gly Pro Gly Arg Ser Tyr Ala Ala Asp Ala Gly Tyr Thr Pro
                20                  25                  30

Ala Ala Ala Ala Thr Pro Ala Thr Pro Ala Ala Thr Pro Ala Gly Gly
            35                  40                  45

Trp Arg Glu Gly Asp Asp Arg Arg Ala Glu Ala Ala Gly Gly Arg Gln
        50                  55                  60

Arg Leu Ala Ser Arg Gln Pro Trp Pro Leu Pro Thr Pro Leu Arg
65              70                  75                  80

Arg Thr Ser Ser Arg Ser Ser Arg Pro Pro Ser Pro Ser Pro Pro Arg
                85                  90                  95

Ala Ser Ser Pro Thr Ser Ala Ala Lys Ala Pro Gly Leu Ile Pro Lys
                100                 105                 110

Leu Asp Thr Ala Tyr Asp Val Ala Tyr Lys Ala Ala Glu Ala His Pro

```
                  115                 120                 125
Arg Gly Gln Val Arg Arg Leu Arg His Cys Pro His Arg Ser Leu Arg
130                 135                 140

Val Ile Ala Gly Ala Leu Glu Val His Ala Val Lys Pro Ala Thr Glu
145                 150                 155                 160

Glu Val Leu Ala Ala Lys Ile Pro Thr Gly Glu Leu Gln Ile Val Asp
                    165                 170                 175

Lys Ile Asp Ala Ala Phe Lys Ile Ala Ala Thr Ala Ala Asn Ala Ala
                180                 185                 190

Pro Thr Asn Asp Lys Phe Thr Val Phe Glu Ser Ala Phe Asn Lys Ala
                    195                 200                 205

Leu Asn Glu Cys Thr Gly Gly Ala Met Arg Pro Thr Ser Ser Ser Pro
210                 215                 220

Pro Ser Arg Pro Arg Ser Ser Arg Pro Thr Pro Pro Ser Pro Ala
225                 230                 235                 240

Ala Pro Glu Val Lys Tyr Ala Val Phe Glu Ala Ala Leu Thr Lys Ala
                    245                 250                 255

Ile Thr Ala Met Thr Gln Ala Gln Lys Ala Gly Lys Pro Ala Ala Ala
                260                 265                 270

Ala Ala Thr Ala Ala Ala Thr Val Ala Thr Ala Ala Thr Ala Ala
                275                 280                 285

Ala Val Leu Pro Pro Pro Leu Leu Val Val Gln Ser Leu Ile Ser Leu
290                 295                 300

Leu Ile Tyr Tyr
305

<210> SEQ ID NO 66
<211> LENGTH: 339
<212> TYPE: PRT
<213> ORGANISM: Lolium perenne

<400> SEQUENCE: 66

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
                20                  25                  30

Ala Thr Pro Ala Thr Pro Ala Ala Pro Ala Thr Ala Ala Thr Pro Ala
            35                  40                  45

Thr Pro Ala Thr Pro Ala Thr Pro Ala Ala Val Pro Ser Gly Lys Ala
50                  55                  60

Thr Thr Glu Glu Gln Lys Leu Ile Glu Lys Ile Asn Ala Gly Phe Lys
65                  70                  75                  80

Ala Ala Val Ala Ala Ala Val Pro Pro Ala Asp Lys Tyr Lys
                85                  90                  95

Thr Phe Val Glu Thr Phe Gly Thr Ala Thr Asn Lys Ala Phe Val Glu
                    100                 105                 110

Gly Leu Ala Ser Gly Tyr Ala Asp Gln Ser Lys Asn Gln Leu Thr Ser
                115                 120                 125

Lys Leu Asp Ala Ala Leu Lys Leu Ala Tyr Glu Ala Ala Gln Gly Ala
                130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                    165                 170                 175
```

```
Ala Glu Glu Val Lys Val Gly Ala Ile Pro Ala Ala Glu Val Gln Leu
            180                 185                 190

Ile Asp Lys Val Asp Ala Ala Tyr Arg Thr Ala Ala Thr Ala Ala Asn
        195                 200                 205

Ala Ala Pro Ala Asn Asp Lys Phe Thr Val Phe Glu Asn Thr Phe Asn
    210                 215                 220

Asn Ala Ile Lys Val Ser Leu Gly Ala Ala Tyr Asp Ser Tyr Lys Phe
225                 230                 235                 240

Ile Pro Thr Leu Val Ala Ala Val Lys Gln Ala Tyr Ala Ala Lys Gln
                245                 250                 255

Ala Thr Ala Pro Glu Val Lys Tyr Thr Val Ser Glu Thr Ala Leu Lys
            260                 265                 270

Lys Ala Val Thr Ala Met Ser Glu Ala Glu Lys Glu Ala Thr Pro Ala
        275                 280                 285

Ala Ala Ala Thr Ala Thr Pro Thr Pro Ala Ala Ala Thr Ala Thr Ala
    290                 295                 300

Thr Pro Ala Ala Ala Tyr Ala Thr Ala Thr Pro Ala Ala Ala Thr Ala
305                 310                 315                 320

Thr Ala Thr Pro Ala Ala Ala Thr Ala Thr Pro Ala Ala Ala Gly Gly
                325                 330                 335

Tyr Lys Val

<210> SEQ ID NO 67
<211> LENGTH: 339
<212> TYPE: PRT
<213> ORGANISM: Lolium perenne

<400> SEQUENCE: 67

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
            20                  25                  30

Ala Thr Pro Ala Thr Pro Ala Ala Pro Ala Thr Ala Ala Thr Pro Ala
        35                  40                  45

Thr Pro Ala Thr Pro Ala Thr Pro Ala Ala Val Pro Ser Gly Lys Ala
    50                  55                  60

Thr Thr Glu Glu Gln Lys Leu Ile Glu Lys Ile Asn Ala Gly Phe Lys
65                  70                  75                  80

Ala Ala Val Ala Ala Ala Val Val Pro Pro Ala Asp Lys Tyr Lys
                85                  90                  95

Thr Phe Val Glu Thr Phe Gly Thr Ala Thr Asn Lys Ala Phe Val Glu
            100                 105                 110

Gly Leu Ala Ser Gly Tyr Ala Asp Gln Ser Lys Asn Gln Leu Thr Ser
        115                 120                 125

Lys Leu Asp Ala Ala Leu Lys Leu Ala Tyr Glu Ala Ala Gln Gly Ala
    130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
            180                 185                 190

Ile Asp Lys Val Asp Ala Ala Tyr Arg Thr Ala Ala Thr Ala Ala Asn
        195                 200                 205
```

```
Ala Ala Pro Ala Asn Asp Lys Phe Thr Val Phe Glu Asn Thr Phe Asn
    210                 215                 220

Asn Ala Ile Lys Val Ser Leu Gly Ala Ala Tyr Asp Ser Tyr Lys Phe
225                 230                 235                 240

Ile Pro Thr Leu Val Ala Ala Val Lys Gln Ala Tyr Ala Ala Lys Gln
                245                 250                 255

Ala Thr Ala Pro Glu Val Lys Tyr Thr Val Ser Glu Thr Ala Leu Lys
            260                 265                 270

Lys Ala Val Thr Ala Met Ser Glu Ala Glu Lys Glu Ala Thr Pro Ala
        275                 280                 285

Ala Ala Ala Thr Ala Thr Pro Thr Pro Ala Ala Thr Ala Thr Ala
    290                 295                 300

Thr Pro Ala Ala Ala Tyr Ala Thr Ala Thr Pro Ala Ala Ala Thr Ala
305                 310                 315                 320

Thr Ala Thr Pro Ala Ala Ala Thr Ala Thr Pro Ala Ala Ala Gly Gly
                325                 330                 335

Tyr Lys Val
```

<210> SEQ ID NO 68
<211> LENGTH: 134
<212> TYPE: PRT
<213> ORGANISM: Lolium perenne
<220> FEATURE:
<221> NAME/KEY: MISC_FEATURE
<222> LOCATION: (103)..(103)
<223> OTHER INFORMATION: Xaa = any amino acid

<400> SEQUENCE: 68

```
Asp Lys Gly Pro Gly Phe Val Val Thr Gly Arg Val Tyr Cys Asp Pro
1               5                   10                  15

Cys Arg Ala Gly Phe Glu Thr Asn Val Ser His Asn Val Glu Gly Ala
            20                  25                  30

Thr Val Ala Val Asp Cys Arg Pro Phe Asp Gly Gly Glu Ser Lys Leu
        35                  40                  45

Lys Ala Glu Ala Thr Thr Asp Lys Asp Gly Trp Tyr Lys Ile Glu Ile
    50                  55                  60

Asp Gln Asp His Gln Glu Glu Ile Cys Glu Val Val Leu Ala Lys Ser
65                  70                  75                  80

Pro Asp Lys Ser Cys Ser Glu Ile Glu Glu Phe Arg Asp Arg Ala Arg
                85                  90                  95

Val Pro Leu Thr Ser Asn Xaa Gly Ile Lys Gln Gln Gly Ile Arg Tyr
            100                 105                 110

Ala Asn Pro Ile Ala Phe Phe Arg Lys Glu Pro Leu Lys Glu Cys Gly
        115                 120                 125

Gly Ile Leu Gln Ala Tyr
            130
```

<210> SEQ ID NO 69
<211> LENGTH: 145
<212> TYPE: PRT
<213> ORGANISM: Olea europaea

<400> SEQUENCE: 69

```
Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
            20                  25                  30
```

```
Phe Ile Pro Gly Ala Ser Leu Arg Leu Gln Cys Lys Asp Lys Glu Asn
             35                  40                  45

Gly Asp Val Thr Phe Thr Glu Val Gly Tyr Thr Arg Ala Glu Gly Leu
 50                  55                  60

Tyr Ser Met Leu Val Glu Arg Asp His Lys Asn Glu Phe Cys Glu Ile
 65                  70                  75                  80

Thr Leu Ile Ser Ser Gly Arg Lys Asp Cys Asn Glu Ile Pro Thr Glu
             85                  90                  95

Gly Trp Ala Lys Pro Ser Leu Lys Phe Lys Leu Asn Thr Val Asn Gly
            100                 105                 110

Thr Thr Arg Thr Val Asn Pro Leu Gly Phe Phe Lys Lys Glu Ala Leu
            115                 120                 125

Pro Lys Cys Ala Gln Val Tyr Asn Lys Leu Gly Met Tyr Pro Pro Asn
            130                 135                 140

Met
145

<210> SEQ ID NO 70
<211> LENGTH: 133
<212> TYPE: PRT
<213> ORGANISM: Parietaria judaica

<400> SEQUENCE: 70

Met Arg Thr Val Ser Met Ala Ala Leu Val Val Ile Ala Ala Ala Leu
 1               5                  10                  15

Ala Trp Thr Ser Ser Ala Glu Pro Ala Pro Ala Pro Ala Pro Gly Glu
             20                  25                  30

Glu Ala Cys Gly Lys Val Val Gln Asp Ile Met Pro Cys Leu His Phe
             35                  40                  45

Val Lys Gly Glu Glu Lys Glu Pro Ser Lys Glu Cys Cys Ser Gly Thr
 50                  55                  60

Lys Lys Leu Ser Glu Glu Val Lys Thr Thr Glu Gln Lys Arg Glu Ala
 65                  70                  75                  80

Cys Lys Cys Ile Val Arg Ala Thr Lys Gly Ile Ser Gly Ile Lys Asn
             85                  90                  95

Glu Leu Val Ala Glu Val Pro Lys Lys Cys Asp Ile Lys Thr Thr Leu
            100                 105                 110

Pro Pro Ile Thr Ala Asp Phe Asp Cys Ser Lys Ile Gln Ser Thr Ile
            115                 120                 125

Phe Arg Gly Tyr Tyr
    130

<210> SEQ ID NO 71
<211> LENGTH: 133
<212> TYPE: PRT
<213> ORGANISM: Parietaria judaica

<400> SEQUENCE: 71

Met Val Arg Ala Leu Met Pro Cys Leu Pro Phe Val Gln Gly Lys Glu
 1               5                  10                  15

Lys Glu Pro Ser Lys Gly Cys Cys Ser Gly Ala Lys Arg Leu Asp Gly
             20                  25                  30

Glu Thr Lys Thr Gly Pro Gln Arg Val His Ala Cys Glu Cys Ile Gln
             35                  40                  45

Thr Ala Met Lys Thr Tyr Ser Asp Ile Asp Gly Lys Leu Val Ser Glu
 50                  55                  60
```

```
Val Pro Lys His Cys Gly Ile Val Asp Ser Lys Leu Pro Pro Ile Asp
 65                  70                  75                  80

Val Asn Met Asp Cys Lys Thr Val Gly Val Pro Arg Gln Pro Gln
                 85                  90                  95

Leu Pro Val Ser Leu Arg His Gly Pro Val Thr Gly Pro Ser Asp Pro
            100                 105                 110

Ala His Lys Ala Arg Leu Glu Arg Pro Gln Ile Arg Val Pro Pro
            115                 120                 125

Ala Pro Glu Lys Ala
            130

<210> SEQ ID NO 72
<211> LENGTH: 133
<212> TYPE: PRT
<213> ORGANISM: Parietaria judaica

<400> SEQUENCE: 72

Met Arg Thr Val Ser Met Ala Ala Leu Val Val Ile Ala Ala Leu
  1               5                  10                  15

Ala Trp Thr Ser Ser Ala Glu Leu Ala Ser Pro Ala Pro Gly Glu
                 20                  25                  30

Gly Pro Cys Gly Lys Val Val His Ile Met Pro Cys Leu Lys Phe
             35                  40                  45

Val Lys Gly Glu Lys Glu Pro Ser Lys Ser Cys Cys Ser Gly Thr
 50                  55                  60

Lys Lys Leu Ser Glu Glu Val Lys Thr Thr Glu Gln Lys Arg Glu Ala
 65                  70                  75                  80

Cys Lys Cys Ile Val Ala Ala Thr Lys Gly Ile Ser Gly Ile Lys Asn
                 85                  90                  95

Glu Leu Val Ala Glu Val Pro Lys Lys Cys Gly Ile Thr Thr Leu
            100                 105                 110

Pro Pro Ile Thr Ala Asp Phe Asp Cys Ser Lys Ile Glu Ser Thr Ile
            115                 120                 125

Phe Arg Gly Tyr Tyr
            130

<210> SEQ ID NO 73
<211> LENGTH: 176
<212> TYPE: PRT
<213> ORGANISM: Parietaria judaica

<400> SEQUENCE: 73

Met Arg Thr Val Ser Ala Pro Ser Ala Val Ala Leu Val Val Ile Val
  1               5                  10                  15

Ala Ala Gly Leu Ala Trp Thr Ser Leu Ala Ser Val Ala Pro Pro Ala
                 20                  25                  30

Pro Ala Pro Gly Ser Glu Glu Thr Cys Gly Thr Val Val Arg Ala Leu
             35                  40                  45

Met Pro Cys Leu Pro Phe Val Gln Gly Lys Glu Lys Glu Pro Ser Lys
 50                  55                  60

Gly Cys Cys Ser Gly Ala Lys Arg Leu Asp Gly Glu Thr Lys Thr Gly
 65                  70                  75                  80

Leu Gln Arg Val His Ala Cys Glu Cys Ile Gln Thr Ala Met Lys Thr
                 85                  90                  95

Tyr Ser Asp Ile Asp Gly Lys Leu Val Ser Glu Val Pro Lys His Cys
            100                 105                 110
```

```
Gly Ile Val Asp Ser Lys Leu Pro Pro Ile Asp Val Asn Met Asp Cys
            115                 120                 125

Lys Thr Leu Gly Val Val Pro Arg Gln Pro Gln Leu Pro Val Ser Leu
        130                 135                 140

Arg His Gly Pro Val Thr Gly Pro Ser Asp Pro Ala His Lys Ala Arg
145                 150                 155                 160

Leu Glu Arg Pro Gln Ile Arg Val Pro Pro Ala Pro Glu Lys Ala
                165                 170                 175

<210> SEQ ID NO 74
<211> LENGTH: 138
<212> TYPE: PRT
<213> ORGANISM: Parietaria judaica

<400> SEQUENCE: 74

Met Arg Thr Val Ser Ala Arg Ser Ser Val Ala Leu Val Val Ile Val
1               5                   10                  15

Ala Ala Val Leu Val Trp Thr Ser Ser Ala Ser Val Ala Pro Ala Pro
            20                  25                  30

Ala Pro Gly Ser Glu Glu Thr Cys Gly Thr Val Val Gly Ala Leu Met
        35                  40                  45

Pro Cys Leu Pro Phe Val Gln Gly Lys Glu Lys Glu Pro Ser Lys Gly
    50                  55                  60

Cys Cys Ser Gly Ala Lys Arg Leu Asp Gly Glu Thr Lys Thr Gly Pro
65                  70                  75                  80

Gln Arg Val His Ala Cys Glu Cys Ile Gln Thr Ala Met Lys Thr Tyr
                85                  90                  95

Ser Asp Ile Asp Gly Lys Leu Val Ser Glu Val Pro Lys His Cys Gly
            100                 105                 110

Ile Val Asp Ser Lys Leu Pro Pro Ile Asp Val Asn Met Asp Cys Lys
        115                 120                 125

Thr Leu Gly Val Leu His Tyr Lys Gly Asn
    130                 135

<210> SEQ ID NO 75
<211> LENGTH: 143
<212> TYPE: PRT
<213> ORGANISM: Parietaria judaica

<400> SEQUENCE: 75

Met Val Arg Ala Leu Met Pro Cys Leu Pro Phe Val Gln Gly Lys Glu
1               5                   10                  15

Lys Glu Pro Ser Lys Gly Cys Cys Ser Gly Ala Lys Arg Leu Asp Gly
            20                  25                  30

Glu Thr Lys Thr Gly Pro Gln Arg Val His Ala Cys Glu Cys Ile Gln
        35                  40                  45

Thr Ala Met Lys Thr Tyr Ser Asp Ile Asp Gly Lys Leu Val Ser Glu
    50                  55                  60

Val Pro Lys His Cys Gly Ile Val Asp Ser Lys Leu Pro Pro Ile Asp
65                  70                  75                  80

Val Asn Met Asp Cys Lys Thr Val Gly Val Pro Arg Gln Pro Gln
                85                  90                  95

Leu Pro Val Ser Leu Arg His Gly Pro Val Thr Gly Pro Ser Arg Ser
            100                 105                 110

Arg Pro Pro Thr Lys His Gly Trp Arg Asp Pro Arg Leu Glu Phe Arg
        115                 120                 125
```

```
Pro Pro His Arg Lys Lys Pro Asn Pro Ala Phe Ser Thr Leu Gly
        130                 135                 140
```

<210> SEQ ID NO 76
<211> LENGTH: 263
<212> TYPE: PRT
<213> ORGANISM: Phleum pratense

<400> SEQUENCE: 76

```
Met Ala Ser Ser Ser Val Leu Leu Val Val Leu Phe Ala Val
1               5                   10                  15

Phe Leu Gly Ser Ala Tyr Gly Ile Pro Lys Val Pro Gly Pro Asn
            20                  25                  30

Ile Thr Ala Thr Tyr Gly Asp Lys Trp Leu Asp Ala Lys Ser Thr Trp
            35                  40                  45

Tyr Gly Lys Pro Thr Gly Ala Gly Pro Lys Asp Asn Gly Gly Ala Cys
    50                  55                  60

Gly Tyr Lys Asp Val Asp Lys Pro Pro Phe Ser Gly Met Thr Gly Cys
65                  70                  75                  80

Gly Asn Thr Pro Ile Phe Lys Ser Gly Arg Gly Cys Gly Ser Cys Phe
                85                  90                  95

Glu Ile Lys Cys Thr Lys Pro Glu Ala Cys Ser Gly Glu Pro Val Val
            100                 105                 110

Val His Ile Thr Asp Asp Asn Glu Glu Pro Ile Ala Pro Tyr His Phe
            115                 120                 125

Asp Leu Ser Gly His Ala Phe Gly Ala Met Ala Lys Lys Gly Asp Glu
        130                 135                 140

Gln Lys Leu Arg Ser Ala Gly Glu Leu Glu Leu Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Tyr Val Asn Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Ile Trp Arg Ile Asp Thr
210                 215                 220

Pro Asp Lys Leu Thr Gly Pro Phe Thr Val Arg Tyr Thr Thr Glu Gly
225                 230                 235                 240

Gly Thr Lys Thr Glu Ala Glu Asp Val Ile Pro Glu Gly Trp Lys Ala
                245                 250                 255

Asp Thr Ser Tyr Glu Ser Lys
                260
```

<210> SEQ ID NO 77
<211> LENGTH: 262
<212> TYPE: PRT
<213> ORGANISM: Phleum pratense

<400> SEQUENCE: 77

```
Met Ala Ser Ser Ser Ser Val Leu Leu Val Val Ala Leu Phe Ala Val
1               5                   10                  15

Phe Leu Gly Ser Ala His Gly Ile Pro Lys Val Pro Pro Gly Pro Asn
            20                  25                  30

Ile Thr Ala Thr Tyr Gly Asp Lys Trp Leu Asp Ala Lys Ser Thr Trp
            35                  40                  45
```

```
Tyr Gly Lys Pro Thr Ala Ala Gly Pro Lys Asp Asn Gly Gly Ala Cys
         50                  55                  60

Gly Tyr Lys Asp Val Asp Lys Pro Pro Phe Ser Gly Met Thr Gly Cys
 65                  70                  75                  80

Gly Asn Thr Pro Ile Phe Lys Ser Gly Arg Gly Cys Gly Ser Cys Phe
                 85                  90                  95

Glu Ile Lys Cys Thr Lys Pro Glu Ala Cys Ser Gly Glu Pro Val Val
            100                 105                 110

Val His Ile Thr Asp Asp Asn Glu Pro Ile Ala Ala Tyr His Phe
            115                 120                 125

Asp Leu Ser Gly Ile Ala Phe Gly Ser Met Ala Lys Lys Gly Asp Glu
        130                 135                 140

Gln Lys Leu Arg Ser Ala Gly Glu Val Glu Ile Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Phe Ser Gly Asp
            180                 185                 190

Gly Asp Val Val Ala Val Asp Ile Lys Glu Lys Gly Lys Asp Lys Trp
        195                 200                 205

Ile Ala Leu Lys Glu Ser Trp Gly Ala Ile Trp Arg Ile Asp Thr Pro
210                 215                 220

Glu Val Leu Lys Gly Pro Phe Thr Val Arg Tyr Thr Thr Glu Gly Gly
225                 230                 235                 240

Thr Lys Ala Arg Ala Lys Asp Val Ile Pro Glu Gly Trp Lys Ala Asp
                245                 250                 255

Thr Ala Tyr Glu Ser Lys
            260

<210> SEQ ID NO 78
<211> LENGTH: 122
<212> TYPE: PRT
<213> ORGANISM: Phleum pratense

<400> SEQUENCE: 78

Met Ser Met Ala Ser Ser Ser Ser Ser Leu Leu Ala Met Ala Val
 1               5                  10                  15

Leu Ala Ala Leu Phe Ala Gly Ala Trp Cys Val Pro Lys Val Thr Phe
                 20                  25                  30

Thr Val Glu Lys Gly Ser Asn Glu Lys His Leu Ala Val Leu Val Lys
            35                  40                  45

Tyr Glu Gly Asp Thr Met Ala Glu Val Glu Leu Arg Glu His Gly Ser
 50                  55                  60

Asp Glu Trp Val Ala Met Thr Lys Gly Glu Gly Val Trp Thr Phe
 65                  70                  75                  80

Asp Ser Glu Glu Pro Leu Gln Gly Pro Phe Asn Phe Arg Phe Leu Thr
                 85                  90                  95

Glu Lys Gly Met Lys Asn Val Phe Asp Asp Val Val Pro Glu Lys Tyr
            100                 105                 110

Thr Ile Gly Ala Thr Tyr Ala Pro Glu Glu
            115                 120

<210> SEQ ID NO 79
<211> LENGTH: 276
<212> TYPE: PRT
<213> ORGANISM: Phleum pratense
```

<400> SEQUENCE: 79

```
Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
            20                  25                  30

Lys Ile Asn Asp Gly Phe Lys Ala Ala Leu Ala Ala Ala Ala Gly Val
        35                  40                  45

Pro Pro Ala Asp Lys Tyr Lys Thr Phe Val Ala Thr Phe Gly Ala Ala
    50                  55                  60

Ser Asn Lys Ala Phe Ala Glu Gly Leu Ser Ala Glu Pro Lys Gly Ala
65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
            100                 105                 110

Tyr Asp Ala Tyr Val Ala Thr Leu Ser Glu Ala Leu Arg Ile Ile Ala
        115                 120                 125

Gly Thr Leu Glu Val His Ala Val Lys Pro Ala Ala Glu Glu Val Lys
    130                 135                 140

Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
            180                 185                 190

Gly Gly Ala Tyr Glu Ser Tyr Lys Phe Ile Pro Ala Leu Glu Ala Ala
        195                 200                 205

Val Lys Gln Ala Tyr Ala Ala Thr Val Ala Thr Ala Pro Glu Val Lys
    210                 215                 220

Tyr Thr Val Phe Glu Thr Ala Leu Lys Lys Ala Phe Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
            260                 265                 270

Gly Tyr Lys Val
        275
```

<210> SEQ ID NO 80
<211> LENGTH: 276
<212> TYPE: PRT
<213> ORGANISM: Phleum pratense

<400> SEQUENCE: 80

```
Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
            20                  25                  30

Lys Ile Asn Asp Gly Phe Lys Ala Ala Leu Ala Ala Ala Ala Gly Val
        35                  40                  45

Pro Pro Ala Asp Lys Tyr Lys Thr Phe Val Ala Thr Phe Gly Ala Ala
    50                  55                  60

Ser Asn Lys Ala Phe Ala Glu Gly Leu Ser Ala Glu Pro Lys Gly Ala
65                  70                  75                  80
```

```
Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
            100                 105                 110

Tyr Asp Ala Tyr Val Ala Thr Leu Ser Glu Ala Leu Arg Ile Ile Ala
        115                 120                 125

Gly Thr Leu Glu Val His Ala Val Lys Pro Ala Ala Glu Glu Val Lys
    130                 135                 140

Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
            180                 185                 190

Gly Gly Ala Tyr Glu Ser Tyr Lys Phe Ile Pro Ala Leu Glu Ala Ala
        195                 200                 205

Val Lys Gln Ala Tyr Ala Ala Thr Val Ala Thr Ala Pro Glu Val Lys
210                 215                 220

Tyr Thr Val Phe Glu Thr Ala Leu Lys Lys Ala Ile Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
            260                 265                 270

Gly Tyr Lys Val
        275

<210> SEQ ID NO 81
<211> LENGTH: 284
<212> TYPE: PRT
<213> ORGANISM: Phleum pratense

<400> SEQUENCE: 81

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
            20                  25                  30

Gly Ala Ala Ala Gly Lys Ala Thr Thr Glu Glu Gln Lys Leu Ile Glu
        35                  40                  45

Asp Ile Asn Val Gly Phe Lys Ala Val Ala Ala Ala Ala Ser Val
    50                  55                  60

Pro Ala Ala Asp Lys Phe Lys Thr Phe Glu Ala Ala Phe Thr Ser Ser
65                  70                  75                  80

Ser Lys Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
            100                 105                 110

Ala Lys Phe Asp Ser Phe Val Ala Ser Leu Thr Glu Ala Leu Arg Val
        115                 120                 125

Ile Ala Gly Ala Leu Glu Val His Ala Val Lys Pro Val Thr Glu Glu
    130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Ala Thr Ala Pro
```

-continued

```
                165                 170                 175
Ala Asp Asp Lys Phe Thr Val Phe Glu Ala Ala Phe Asn Lys Ala Ile
            180                 185                 190
Lys Glu Ser Thr Gly Gly Ala Tyr Asp Thr Tyr Lys Cys Ile Pro Ser
            195                 200                 205
Leu Glu Ala Ala Val Lys Gln Ala Tyr Ala Ala Thr Val Ala Ala Ala
            210                 215                 220
Pro Gln Val Lys Tyr Ala Val Phe Glu Ala Ala Leu Thr Lys Ala Ile
225                 230                 235                 240
Thr Ala Met Ser Glu Val Gln Lys Val Ser Gln Pro Ala Thr Gly Ala
            245                 250                 255
Ala Thr Val Ala Ala Gly Ala Ala Thr Thr Ala Ala Gly Ala Ala Ser
            260                 265                 270
Gly Ala Ala Thr Val Ala Ala Gly Gly Tyr Lys Val
            275                 280

<210> SEQ ID NO 82
<211> LENGTH: 286
<212> TYPE: PRT
<213> ORGANISM: Phleum pratense

<400> SEQUENCE: 82

Ala Asp Leu Gly Tyr Gly Pro Ala Thr Pro Ala Ala Pro Ala Ala Gly
1               5                   10                  15
Tyr Thr Pro Ala Thr Pro Ala Ala Pro Ala Gly Ala Asp Ala Ala Gly
            20                  25                  30
Lys Ala Thr Thr Glu Glu Gln Lys Leu Ile Glu Lys Ile Asn Ala Gly
            35                  40                  45
Phe Lys Ala Ala Leu Ala Gly Ala Gly Val Gln Pro Ala Asp Lys Tyr
        50                  55                  60
Arg Thr Phe Val Ala Thr Phe Gly Pro Ala Ser Asn Lys Ala Phe Ala
65                  70                  75                  80
Glu Gly Leu Ser Gly Glu Pro Lys Gly Ala Ala Glu Ser Ser Ser Lys
                85                  90                  95
Ala Ala Leu Thr Ser Lys Leu Asp Ala Ala Tyr Lys Leu Ala Tyr Lys
            100                 105                 110
Thr Ala Glu Gly Ala Thr Pro Glu Ala Lys Tyr Asp Ala Tyr Val Ala
            115                 120                 125
Thr Leu Ser Glu Ala Leu Arg Ile Ile Ala Gly Thr Leu Glu Val His
        130                 135                 140
Ala Val Lys Pro Ala Ala Glu Glu Val Lys Val Ile Pro Ala Gly Glu
145                 150                 155                 160
Leu Gln Val Ile Glu Lys Val Asp Ala Ala Phe Lys Val Ala Ala Thr
                165                 170                 175
Ala Ala Asn Ala Ala Pro Ala Asn Asp Lys Phe Thr Val Phe Glu Ala
            180                 185                 190
Ala Phe Asn Asp Glu Ile Lys Ala Ser Thr Gly Gly Ala Tyr Glu Ser
            195                 200                 205
Tyr Lys Phe Ile Pro Ala Leu Glu Ala Ala Val Lys Gln Ala Tyr Ala
        210                 215                 220
Ala Thr Val Ala Thr Ala Pro Glu Val Lys Tyr Thr Val Phe Glu Thr
225                 230                 235                 240
Ala Leu Lys Lys Ala Ile Thr Ala Met Ser Glu Ala Gln Lys Ala Ala
                245                 250                 255
```

```
Lys Pro Ala Ala Ala Thr Ala Thr Ala Ala Val Gly Ala
        260                 265                 270

Ala Thr Gly Ala Ala Thr Ala Thr Gly Gly Tyr Lys Val
        275                 280                 285

<210> SEQ ID NO 83
<211> LENGTH: 287
<212> TYPE: PRT
<213> ORGANISM: Phleum pratense

<400> SEQUENCE: 83

Met Ala Val Gln Lys Tyr Thr Val Ala Leu Phe Leu Ala Val Ala Leu
1               5                   10                  15

Val Ala Gly Pro Ala Ala Ser Tyr Ala Ala Asp Ala Gly Tyr Ala Pro
                20                  25                  30

Ala Thr Pro Ala Ala Ala Gly Ala Glu Ala Gly Lys Ala Thr Thr Glu
            35                  40                  45

Glu Gln Lys Leu Ile Glu Asp Ile Asn Val Gly Phe Lys Ala Ala Val
        50                  55                  60

Ala Ala Ala Ala Ser Val Pro Ala Ala Asp Lys Phe Lys Thr Phe Glu
65                  70                  75                  80

Ala Ala Phe Thr Ser Ser Ser Lys Ala Ala Thr Ala Lys Ala Pro Gly
                85                  90                  95

Leu Val Pro Lys Leu Asp Ala Ala Tyr Ser Val Ser Tyr Lys Ala Ala
            100                 105                 110

Val Gly Ala Thr Pro Glu Ala Lys Phe Asp Ser Phe Val Ala Ser Leu
        115                 120                 125

Thr Glu Ala Leu Arg Val Ile Ala Gly Ala Leu Glu Val His Ala Val
130                 135                 140

Lys Pro Val Thr Glu Glu Pro Gly Met Ala Lys Ile Pro Ala Gly Glu
145                 150                 155                 160

Leu Gln Ile Ile Asp Lys Ile Asp Ala Ala Phe Lys Val Ala Ala Thr
                165                 170                 175

Ala Ala Ala Thr Ala Pro Ala Asp Thr Val Phe Glu Ala Ala Phe Asn
            180                 185                 190

Lys Ala Ile Lys Glu Ser Thr Gly Gly Ala Tyr Asp Thr Tyr Lys Cys
        195                 200                 205

Ile Pro Ser Leu Glu Ala Ala Val Lys Gln Ala Tyr Ala Ala Thr Val
210                 215                 220

Ala Ala Ala Pro Gln Val Lys Tyr Ala Val Phe Glu Ala Ala Leu Thr
225                 230                 235                 240

Lys Ala Ile Thr Ala Met Ser Glu Val Gln Lys Val Ser Gln Pro Ala
                245                 250                 255

Thr Gly Ala Ala Thr Val Ala Ala Gly Ala Ala Thr Thr Ala Ala Gly
            260                 265                 270

Ala Ala Ser Gly Ala Ala Thr Val Ala Ala Gly Gly Tyr Lys Val
        275                 280                 285

<210> SEQ ID NO 84
<211> LENGTH: 290
<212> TYPE: PRT
<213> ORGANISM: Phleum pratense

<400> SEQUENCE: 84

Met Ala Val Gln Lys Tyr Thr Val Ala Leu Phe Leu Ala Val Ala Leu
1               5                   10                  15
```

```
Val Ala Gly Pro Ala Ala Ser Tyr Ala Asp Ala Gly Tyr Ala Pro
            20                  25                  30

Ala Thr Pro Ala Ala Ala Gly Ala Glu Ala Gly Lys Ala Thr Thr Glu
        35                  40                  45

Glu Gln Lys Leu Ile Glu Asp Ile Asn Val Gly Phe Lys Ala Ala Val
    50                  55                  60

Ala Ala Ala Ala Ser Val Pro Ala Ala Asp Lys Phe Lys Thr Phe Glu
65                  70                  75                  80

Ala Ala Phe Thr Ser Ser Ser Lys Ala Ala Thr Ala Lys Ala Pro Gly
                85                  90                  95

Leu Val Pro Lys Leu Asp Ala Ala Tyr Ser Val Ala Tyr Lys Ala Ala
            100                 105                 110

Val Gly Ala Thr Pro Glu Ala Lys Phe Asp Ser Phe Val Ala Ser Leu
        115                 120                 125

Thr Glu Ala Leu Arg Val Ile Ala Gly Ala Leu Glu Val His Ala Val
    130                 135                 140

Lys Pro Val Thr Glu Asp Pro Ala Trp Pro Lys Ile Pro Ala Gly Glu
145                 150                 155                 160

Leu Gln Ile Ile Asp Lys Ile Asp Ala Ala Phe Lys Val Ala Ala Thr
                165                 170                 175

Ala Ala Ala Thr Ala Pro Ala Asp Asp Lys Phe Thr Val Phe Glu Ala
            180                 185                 190

Ala Phe Asn Lys Ala Ile Lys Glu Ser Thr Gly Gly Ala Tyr Asp Thr
        195                 200                 205

Tyr Lys Cys Ile Pro Ser Leu Glu Ala Ala Val Lys Gln Ala Tyr Ala
    210                 215                 220

Ala Thr Val Ala Ala Pro Gln Val Lys Tyr Ala Val Phe Glu Ala
225                 230                 235                 240

Ala Leu Thr Lys Ala Ile Thr Ala Met Ser Glu Val Gln Lys Val Ser
                245                 250                 255

Gln Pro Ala Thr Gly Ala Ala Thr Val Ala Ala Gly Ala Thr Thr
            260                 265                 270

Ala Thr Gly Ala Ala Ser Gly Ala Ala Thr Val Ala Ala Gly Gly Tyr
        275                 280                 285

Lys Val
    290

<210> SEQ ID NO 85
<211> LENGTH: 265
<212> TYPE: PRT
<213> ORGANISM: Phleum pratense

<400> SEQUENCE: 85

Ala Asp Ala Gly Tyr Ala Pro Ala Thr Pro Ala Ala Gly Ala Glu
1               5                   10                  15

Ala Gly Lys Ala Thr Thr Glu Glu Gln Lys Leu Ile Glu Asp Ile Asn
            20                  25                  30

Val Gly Phe Lys Ala Ala Val Ala Ala Ala Ala Ser Val Pro Ala Ala
        35                  40                  45

Asp Lys Phe Lys Thr Phe Glu Ala Ala Phe Thr Ser Ser Ser Lys Ala
    50                  55                  60

Ala Thr Ala Lys Ala Pro Gly Leu Val Pro Lys Leu Asp Ala Ala Tyr
65                  70                  75                  80

Ser Val Ala Tyr Lys Ala Ala Val Gly Ala Thr Pro Glu Ala Lys Phe
                85                  90                  95
```

```
Asp Ser Phe Val Ala Ser Leu Thr Glu Ala Leu Arg Val Ile Ala Gly
            100                 105                 110

Ala Leu Glu Val His Ala Val Lys Pro Val Thr Glu Glu Pro Gly Met
        115                 120                 125

Ala Lys Ile Pro Ala Gly Glu Leu Gln Ile Ile Asp Lys Ile Asp Ala
130                 135                 140

Ala Phe Lys Val Ala Ala Thr Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175

Thr Gly Gly Ala Tyr Asp Thr Tyr Lys Cys Ile Pro Ser Leu Glu Ala
            180                 185                 190

Ala Val Lys Gln Ala Tyr Ala Ala Thr Val Ala Ala Pro Gln Val
        195                 200                 205

Lys Tyr Ala Val Phe Glu Ala Ala Leu Thr Lys Ala Ile Thr Ala Met
210                 215                 220

Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
                245                 250                 255

Thr Val Ala Ala Gly Gly Tyr Lys Val
            260                 265

<210> SEQ ID NO 86
<211> LENGTH: 295
<212> TYPE: PRT
<213> ORGANISM: Phleum pratense

<400> SEQUENCE: 86

Ser Val Lys Arg Ser Asn Gly Ser Ala Glu Val His Arg Gly Ala Val
1               5                   10                  15

Pro Arg Arg Gly Pro Arg Gly Gly Pro Gly Arg Ser Tyr Ala Ala Asp
            20                  25                  30

Ala Gly Tyr Ala Pro Ala Thr Pro Ala Ala Gly Ala Glu Ala Gly
        35                  40                  45

Lys Ala Thr Thr Glu Glu Gln Lys Leu Ile Glu Asp Ile Asn Val Gly
    50                  55                  60

Phe Lys Ala Ala Val Ala Ala Ala Ser Val Pro Ala Ala Asp Lys
65                  70                  75                  80

Phe Lys Thr Phe Glu Ala Ala Phe Thr Ser Ser Ser Lys Ala Ala Thr
                85                  90                  95

Ala Lys Ala Pro Gly Leu Val Pro Lys Leu Asp Ala Ala Tyr Ser Val
            100                 105                 110

Ala Tyr Lys Ala Ala Val Gly Ala Thr Pro Glu Ala Lys Phe Asp Ser
        115                 120                 125

Phe Val Ala Ser Leu Thr Glu Ala Leu Arg Val Ile Ala Gly Ala Leu
130                 135                 140

Glu Val His Ala Val Lys Pro Val Thr Glu Glu Pro Gly Met Ala Lys
145                 150                 155                 160

Ile Pro Ala Gly Glu Leu Gln Ile Ile Asp Lys Ile Asp Ala Ala Phe
                165                 170                 175

Lys Val Ala Ala Thr Ala Ala Thr Ala Pro Ala Asp Asp Lys Phe
            180                 185                 190

Thr Val Phe Glu Ala Ala Phe Asn Lys Ala Ile Lys Glu Ser Thr Gly
```

-continued

```
                195                 200                 205
Gly Ala Tyr Asp Thr Tyr Lys Cys Ile Pro Ser Leu Glu Ala Ala Val
    210                 215                 220

Lys Gln Ala Tyr Ala Ala Thr Val Ala Ala Pro Gln Val Lys Tyr
225                 230                 235                 240

Ala Val Phe Glu Ala Ala Leu Thr Lys Ala Ile Thr Ala Met Ser Glu
                245                 250                 255

Val Gln Lys Val Ser Gln Pro Ala Thr Gly Ala Ala Thr Val Ala Ala
            260                 265                 270

Gly Ala Ala Thr Thr Ala Ala Gly Ala Ala Ser Gly Ala Ala Thr Val
                275                 280                 285

Ala Ala Gly Gly Tyr Lys Val
    290                 295

<210> SEQ ID NO 87
<211> LENGTH: 312
<212> TYPE: PRT
<213> ORGANISM: Phleum pratense

<400> SEQUENCE: 87

Met Ala Val His Gln Tyr Thr Val Ala Leu Phe Leu Ala Val Ala Leu
1               5                   10                  15

Val Ala Gly Pro Ala Gly Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
        35                  40                  45

Ala Pro Ala Gly Ala Glu Pro Ala Gly Lys Ala Thr Thr Glu Glu Gln
    50                  55                  60

Lys Leu Ile Glu Lys Ile Asn Ala Gly Phe Lys Ala Ala Leu Ala Ala
65                  70                  75                  80

Ala Ala Gly Val Pro Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
    130                 135                 140

Pro Glu Ala Lys Tyr Asp Ala Tyr Val Ala Thr Val Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Ala Asn Ala Ala Pro
        195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
            260                 265                 270
```

```
Thr Ala Met Ser Glu Ala Gln Lys Ala Ala Lys Pro Ala Ala Ala
            275                 280                 285

Thr Ala Thr Ala Thr Ala Val Gly Ala Ala Thr Gly Ala Ala Thr
            290                 295                 300

Ala Ala Thr Gly Gly Tyr Lys Val
305                 310
```

```
<210> SEQ ID NO 88
<211> LENGTH: 276
<212> TYPE: PRT
<213> ORGANISM: Phleum pratense

<400> SEQUENCE: 88

Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
                20                  25                  30

Lys Ile Asn Asp Gly Phe Lys Ala Ala Leu Ala Ala Ala Ala Gly Val
            35                  40                  45

Pro Pro Ala Asp Lys Tyr Lys Thr Phe Val Ala Thr Phe Gly Ala Ala
    50                  55                  60

Ser Asn Lys Ala Phe Ala Glu Gly Leu Ser Ala Glu Pro Lys Gly Ala
65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
            100                 105                 110

Tyr Asp Ala Tyr Val Ala Thr Leu Ser Glu Ala Leu Arg Ile Ile Ala
        115                 120                 125

Gly Thr Leu Glu Val His Ala Val Lys Pro Ala Ala Glu Glu Val Lys
    130                 135                 140

Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
            180                 185                 190

Gly Gly Ala Tyr Glu Ser Tyr Lys Phe Ile Pro Ala Leu Glu Ala Ala
        195                 200                 205

Val Lys Gln Ala Tyr Ala Ala Thr Val Ala Thr Ala Pro Glu Val Lys
    210                 215                 220

Tyr Thr Val Phe Glu Thr Ala Leu Lys Lys Ala Phe Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
            260                 265                 270

Gly Tyr Lys Val
            275
```

```
<210> SEQ ID NO 89
<211> LENGTH: 284
<212> TYPE: PRT
<213> ORGANISM: Phleum pratense

<400> SEQUENCE: 89
```

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
            20                  25                  30

Gly Ala Ala Ala Gly Lys Ala Thr Thr Glu Glu Gln Lys Leu Ile Glu
        35                  40                  45

Asp Ile Asn Val Gly Phe Lys Ala Ala Val Ala Ala Ala Ala Ser Val
    50                  55                  60

Pro Ala Ala Asp Lys Phe Lys Thr Phe Glu Ala Ala Phe Thr Ser Ser
65                  70                  75                  80

Ser Lys Ala Ala Ala Lys Ala Pro Gly Leu Val Pro Lys Leu Asp
            85                  90                  95

Ala Ala Tyr Ser Val Ala Tyr Lys Ala Ala Val Gly Ala Thr Pro Glu
            100                 105                 110

Ala Lys Phe Asp Ser Phe Val Ala Ser Leu Thr Glu Ala Leu Arg Val
        115                 120                 125

Ile Ala Gly Ala Leu Glu Val His Ala Val Lys Pro Val Thr Glu Glu
    130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Ala Thr Ala Pro
                165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
        195                 200                 205

Leu Glu Ala Ala Val Lys Gln Ala Tyr Ala Ala Thr Val Ala Ala Ala
    210                 215                 220

Pro Gln Val Lys Tyr Ala Val Phe Glu Ala Ala Leu Thr Lys Ala Ile
225                 230                 235                 240

Thr Ala Met Ser Glu Val Gln Lys Val Ser Gln Pro Ala Thr Gly Ala
                245                 250                 255

Ala Thr Val Ala Ala Gly Ala Ala Thr Thr Ala Ala Gly Ala Ala Ser
            260                 265                 270

Gly Ala Ala Thr Val Ala Ala Gly Gly Tyr Lys Val
        275                 280

<210> SEQ ID NO 90
<211> LENGTH: 286
<212> TYPE: PRT
<213> ORGANISM: Phleum pratense

<400> SEQUENCE: 90

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
            20                  25                  30

Lys Ala Thr Thr Glu Glu Gln Lys Leu Ile Glu Lys Ile Asn Ala Gly
        35                  40                  45

Phe Lys Ala Ala Leu Ala Gly Ala Gly Val Gln Pro Ala Asp Lys Tyr
    50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
            85                  90                  95

```
Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
            115                 120                 125

Thr Leu Ser Glu Ala Leu Arg Ile Ile Ala Gly Thr Leu Glu Val His
        130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Ala Ala Ala Ala Thr Ala Thr Ala Thr Ala Ala Val Gly Ala
            260                 265                 270

Ala Thr Gly Ala Ala Thr Ala Ala Thr Gly Gly Tyr Lys Val
        275                 280                 285

<210> SEQ ID NO 91
<211> LENGTH: 281
<212> TYPE: PRT
<213> ORGANISM: Phleum pratense

<400> SEQUENCE: 91

Ala Val Pro Arg Arg Gly Pro Arg Gly Gly Pro Gly Arg Ser Tyr Ala
1               5                   10                  15

Ala Asp Ala Gly Tyr Ala Pro Ala Thr Pro Ala Ala Ala Gly Ala Glu
            20                  25                  30

Ala Gly Lys Ala Thr Thr Glu Glu Gln Lys Leu Ile Glu Asp Ile Asn
        35                  40                  45

Val Gly Phe Lys Ala Ala Val Ala Ala Ala Ser Val Pro Ala Gly
    50                  55                  60

Asp Lys Phe Lys Thr Phe Glu Ala Ala Phe Thr Ser Ser Ser Lys Ala
65                  70                  75                  80

Ala Thr Ala Lys Ala Pro Gly Leu Val Pro Lys Leu Asp Ala Ala Tyr
                85                  90                  95

Ser Val Ala Tyr Lys Ala Ala Val Gly Ala Thr Pro Glu Ala Lys Phe
            100                 105                 110

Asp Ser Phe Val Ala Ser Leu Thr Glu Ala Leu Arg Val Ile Ala Gly
        115                 120                 125

Ala Leu Glu Val His Ala Val Lys Pro Val Thr Glu Glu Pro Gly Met
    130                 135                 140

Ala Lys Ile Pro Ala Gly Glu Leu Gln Ile Ile Asp Lys Ile Asp Ala
145                 150                 155                 160

Ala Phe Lys Val Ala Ala Thr Ala Ala Thr Ala Pro Ala Asp Asp
                165                 170                 175

Lys Phe Thr Val Phe Glu Ala Ala Phe Asn Lys Ala Ile Lys Glu Ser
```

```
            180                 185                 190
Thr Gly Gly Ala Tyr Asp Thr Tyr Lys Cys Ile Pro Ser Leu Glu Ala
                195                 200                 205
Ala Val Lys Gln Ala Tyr Ala Ala Thr Val Ala Ala Pro Gln Val
    210                 215                 220
Lys Tyr Ala Val Phe Glu Ala Ala Leu Thr Lys Ala Ile Thr Ala Met
225                 230                 235                 240
Ser Glu Val Gln Lys Val Ser Gln Pro Ala Thr Gly Ala Ala Thr Val
                245                 250                 255
Ala Ala Gly Ala Ala Thr Thr Ala Thr Gly Ala Ala Ser Gly Ala Ala
            260                 265                 270
Thr Val Ala Ala Gly Gly Tyr Lys Val
            275                 280

<210> SEQ ID NO 92
<211> LENGTH: 280
<212> TYPE: PRT
<213> ORGANISM: Phleum pratense

<400> SEQUENCE: 92

Met Ala Val Pro Arg Arg Gly Pro Arg Gly Pro Gly Arg Ser Tyr
1               5                   10                  15
Thr Ala Asp Ala Gly Tyr Ala Pro Ala Thr Pro Ala Ala Gly Ala
                20                  25                  30
Ala Ala Gly Lys Ala Thr Thr Glu Glu Gln Lys Leu Ile Glu Asp Ile
            35                  40                  45
Asn Val Gly Phe Lys Ala Ala Val Ala Ala Arg Gln Arg Pro Ala Ala
    50                  55                  60
Asp Lys Phe Lys Thr Phe Glu Ala Ala Ser Pro Arg His Pro Arg Pro
65                  70                  75                  80
Leu Arg Gln Gly Ala Gly Leu Val Pro Lys Leu Asp Ala Ala Tyr Ser
                85                  90                  95
Val Ala Tyr Lys Ala Ala Val Gly Ala Thr Pro Glu Ala Lys Phe Asp
                100                 105                 110
Ser Phe Val Ala Ser Leu Thr Glu Ala Leu Arg Val Ile Ala Gly Ala
            115                 120                 125
Leu Glu Val His Ala Val Lys Pro Val Thr Glu Glu Pro Gly Met Ala
        130                 135                 140
Lys Ile Pro Ala Gly Glu Leu Gln Ile Ile Asp Lys Ile Asp Ala Ala
145                 150                 155                 160
Phe Lys Val Ala Ala Thr Ala Ala Thr Ala Pro Ala Asp Asp Lys
                165                 170                 175
Phe Thr Val Phe Glu Ala Ala Phe Asn Lys Ala Ile Lys Glu Ser Thr
            180                 185                 190
Gly Gly Ala Tyr Asp Thr Tyr Lys Cys Ile Pro Ser Leu Glu Ala Ala
                195                 200                 205
Val Lys Gln Ala Tyr Ala Ala Thr Val Ala Ala Ala Glu Val Lys
    210                 215                 220
Tyr Ala Val Phe Glu Ala Ala Leu Thr Lys Ala Ile Thr Ala Met Ser
225                 230                 235                 240
Glu Val Gln Lys Val Ser Gln Pro Ala Thr Gly Ala Ala Thr Val Ala
                245                 250                 255
Ala Gly Ala Ala Thr Thr Ala Ala Gly Ala Ala Ser Gly Ala Ala Thr
            260                 265                 270
```

-continued

```
Val Ala Ala Gly Gly Tyr Lys Val
            275             280

<210> SEQ ID NO 93
<211> LENGTH: 312
<212> TYPE: PRT
<213> ORGANISM: Phleum pratense

<400> SEQUENCE: 93

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
            35                  40                  45

Ala Pro Ala Glu Ala Ala Pro Ala Gly Lys Ala Thr Thr Glu Glu Gln
        50                  55                  60

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
            115                 120                 125

Leu Asp Ala Ala Tyr Lys Leu Ala Tyr Lys Thr Ala Glu Gly Ala Thr
        130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Ala Asn Ala Ala Pro
        195                 200                 205

Ala Asn Asp Lys Phe Thr Val Phe Glu Ala Ala Phe Asn Asp Ala Ile
        210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
            260                 265                 270

Thr Ala Met Ser Glu Ala Gln Lys Ala Lys Pro Ala Ala Ala Ala
            275                 280                 285

Thr Ala Thr Ala Thr Ala Ala Val Gly Ala Ala Thr Gly Ala Ala Thr
        290                 295                 300

Ala Ala Thr Gly Gly Tyr Lys Val
305                 310

<210> SEQ ID NO 94
<211> LENGTH: 257
<212> TYPE: PRT
<213> ORGANISM: Phleum pratense

<400> SEQUENCE: 94
```

Glu Ala Pro Ala Gly Lys Ala Thr Thr Glu Gln Lys Leu Ile Glu
1               5                   10                  15

Lys Ile Asn Ala Gly Phe Lys Ala Ala Leu Ala Arg Arg Leu Gln Pro
            20                  25                  30

Ala Asp Lys Tyr Arg Thr Phe Val Ala Thr Phe Gly Pro Ala Ser Asn
            35                  40                  45

Lys Ala Phe Ala Glu Gly Leu Ser Gly Glu Pro Lys Gly Ala Ala Glu
50                  55                  60

Ser Ser Ser Lys Ala Ala Leu Thr Ser Lys Leu Asp Ala Ala Tyr Lys
65                  70                  75                  80

Leu Ala Tyr Lys Thr Ala Glu Gly Ala Thr Pro Glu Ala Lys Tyr Asp
            85                  90                  95

Ala Tyr Val Ala Thr Leu Ser Glu Ala Leu Arg Ile Ile Ala Gly Thr
            100                 105                 110

Leu Glu Val His Ala Val Lys Pro Ala Ala Glu Glu Val Lys Val Ile
            115                 120                 125

Pro Ala Ala Glu Leu Gln Val Ile Glu Lys Val Asp Ala Ala Phe Lys
            130                 135                 140

Val Ala Ala Thr Ala Ala Asn Ala Ala Pro Ala Asn Asp Lys Phe Thr
145                 150                 155                 160

Val Phe Glu Ala Ala Phe Asn Asp Glu Ile Lys Ala Ser Thr Gly Gly
            165                 170                 175

Ala Tyr Glu Ser Tyr Lys Phe Ile Pro Ala Leu Glu Ala Ala Val Lys
            180                 185                 190

Gln Ala Tyr Ala Ala Thr Val Ala Thr Ala Pro Glu Val Lys Tyr Thr
            195                 200                 205

Val Phe Glu Thr Ala Leu Lys Lys Ala Ile Thr Ala Met Ser Glu Ala
            210                 215                 220

Gln Lys Ala Ala Lys Pro Pro Leu Pro Pro Pro Gln Pro Pro
225                 230                 235                 240

Pro Leu Ala Ala Thr Gly Ala Ala Thr Ala Ala Thr Gly Gly Tyr Lys
            245                 250                 255

Val

<210> SEQ ID NO 95
<211> LENGTH: 312
<212> TYPE: PRT
<213> ORGANISM: Phleum pratense

<400> SEQUENCE: 95

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
            35                  40                  45

Ala Pro Ala Glu Ala Ala Pro Ala Gly Lys Ala Thr Thr Glu Glu Gln
50                  55                  60

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
            85                  90                  95

Phe Gly Ala Ala Ser Asn Lys Ala Phe Ala Glu Gly Leu Ser Gly Glu
            100                 105                 110

```
Pro Lys Gly Ala Ala Glu Ser Ser Lys Ala Ala Leu Thr Ser Lys
            115                 120                 125

Leu Asp Ala Ala Tyr Lys Leu Ala Tyr Lys Thr Ala Glu Gly Ala Thr
130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
                180                 185                 190

Val Asp Ala Ala Phe Lys Val Ala Ala Thr Ala Ala Asn Ala Ala Pro
                195                 200                 205

Ala Asn Asp Lys Phe Thr Val Phe Glu Ala Ala Phe Asn Asp Ala Ile
            210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
                260                 265                 270

Thr Ala Met Ser Glu Ala Gln Lys Ala Ala Lys Pro Ala Ala Ala Ala
            275                 280                 285

Thr Ala Thr Ala Thr Ala Val Gly Ala Ala Thr Gly Ala Ala Ala Thr
            290                 295                 300

Ala Ala Thr Gly Gly Tyr Lys Val
305                 310

<210> SEQ ID NO 96
<211> LENGTH: 280
<212> TYPE: PRT
<213> ORGANISM: Phleum pratense

<400> SEQUENCE: 96

Met Ala Val Pro Arg Gly Pro Arg Gly Pro Gly Arg Ser Tyr
1               5                   10                  15

Thr Ala Asp Ala Gly Tyr Ala Pro Ala Thr Pro Ala Ala Ala Gly Ala
                20                  25                  30

Ala Ala Gly Lys Ala Thr Thr Glu Glu Gln Lys Leu Ile Glu Asp Ile
            35                  40                  45

Asn Val Gly Phe Lys Ala Val Ala Ala Arg Gln Arg Pro Ala Ala
        50                  55                  60

Asp Lys Phe Lys Thr Phe Glu Ala Ala Ser Pro Arg His Pro Arg Pro
65                  70                  75                  80

Leu Arg Gln Gly Ala Gly Leu Val Pro Lys Leu Asp Ala Ala Tyr Ser
                85                  90                  95

Val Ala Tyr Lys Ala Ala Val Gly Ala Thr Pro Glu Ala Lys Phe Asp
                100                 105                 110

Ser Phe Val Ala Ser Leu Thr Glu Ala Leu Arg Val Ile Ala Gly Ala
            115                 120                 125

Leu Glu Val His Ala Val Lys Pro Val Thr Glu Glu Pro Gly Met Ala
            130                 135                 140

Lys Ile Pro Ala Gly Glu Leu Gln Ile Ile Asp Lys Ile Asp Ala Ala
145                 150                 155                 160

Phe Lys Val Ala Ala Thr Ala Ala Ala Thr Ala Pro Ala Asp Asp Lys
                165                 170                 175
```

```
Phe Thr Val Phe Glu Ala Ala Phe Asn Lys Ala Ile Lys Glu Ser Thr
            180                 185                 190

Gly Gly Ala Tyr Asp Thr Tyr Lys Cys Ile Pro Ser Leu Glu Ala Ala
        195                 200                 205

Val Lys Gln Ala Tyr Ala Ala Thr Val Ala Ala Ala Glu Val Lys
    210                 215                 220

Tyr Ala Val Phe Glu Ala Ala Leu Thr Lys Ala Ile Thr Ala Met Ser
225                 230                 235                 240

Glu Val Gln Lys Val Ser Gln Pro Ala Thr Gly Ala Ala Thr Val Ala
                245                 250                 255

Ala Gly Ala Ala Thr Thr Ala Ala Gly Ala Ala Ser Gly Ala Ala Thr
                260                 265                 270

Val Ala Ala Gly Gly Tyr Lys Val
    275                 280

<210> SEQ ID NO 97
<211> LENGTH: 285
<212> TYPE: PRT
<213> ORGANISM: Phleum pratense

<400> SEQUENCE: 97

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
                20                  25                  30

Lys Ala Thr Thr Glu Glu Gln Lys Leu Ile Glu Lys Ile Asn Ala Gly
            35                  40                  45

Phe Lys Ala Ala Leu Ala Gly Ala Gly Val Gln Pro Ala Asp Lys Tyr
    50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
                85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
        115                 120                 125

Thr Leu Ser Glu Ala Leu Arg Ile Ile Ala Gly Thr Leu Glu Val His
    130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Pro Pro Leu Pro Pro Pro Gln Pro Pro Leu Ala Ala
```

```
                    260                 265                 270
Thr Gly Ala Ala Thr Ala Ala Thr Gly Gly Tyr Lys Val
            275                 280                 285

<210> SEQ ID NO 98
<211> LENGTH: 312
<212> TYPE: PRT
<213> ORGANISM: Phleum pratense

<400> SEQUENCE: 98

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
        35                  40                  45

Ala Pro Ala Glu Ala Ala Pro Ala Gly Lys Ala Thr Thr Glu Glu Gln
    50                  55                  60

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Leu Thr Ser Lys
        115                 120                 125

Leu Asp Ala Ala Tyr Lys Leu Ala Tyr Lys Thr Ala Glu Gly Ala Thr
    130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Ala Asn Ala Ala Pro
        195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
            260                 265                 270

Thr Ala Met Ser Glu Ala Gln Lys Ala Ala Lys Pro Ala Ala Ala Ala
        275                 280                 285

Thr Ala Thr Ala Thr Ala Ala Val Gly Ala Ala Thr Gly Ala Ala Thr
    290                 295                 300

Ala Ala Thr Gly Gly Tyr Lys Val
305                 310

<210> SEQ ID NO 99
<211> LENGTH: 138
<212> TYPE: PRT
<213> ORGANISM: Phleum pratense
```

-continued

```
<400> SEQUENCE: 99

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu Arg Ile Ile Ala Gly Thr
        115                 120                 125

Pro Glu Val His Ala Val Lys Pro Gly Ala
    130                 135

<210> SEQ ID NO 100
<211> LENGTH: 57
<212> TYPE: PRT
<213> ORGANISM: Phleum pratense

<400> SEQUENCE: 100

Ser Lys Ala Pro Gln Leu Val Pro Lys Leu Asp Glu Val Tyr Asn Ala
1               5                   10                  15

Ala Tyr Asn Ala Ala Asp His Ala Ala Pro Glu Asp Lys Tyr Glu Ala
            20                  25                  30

Phe Val Leu His Phe Ser Glu Ala Leu His Ile Ile Ala Gly Thr Pro
        35                  40                  45

Glu Val His Ala Val Lys Pro Gly Ala
    50                  55

<210> SEQ ID NO 101
<211> LENGTH: 80
<212> TYPE: PRT
<213> ORGANISM: Phleum pratense

<400> SEQUENCE: 101

Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
            20                  25                  30

Leu Asp Glu Val Tyr Asn Ala Ala Tyr Asn Ala Ala Asp His Ala Ala
        35                  40                  45

Pro Glu Asp Lys Tyr Glu Ala Phe Val Leu His Phe Ser Glu Ala Leu
    50                  55                  60

His Ile Ile Ala Gly Thr Pro Glu Val His Ala Val Lys Pro Gly Ala
65                  70                  75                  80

<210> SEQ ID NO 102
<211> LENGTH: 106
<212> TYPE: PRT
<213> ORGANISM: Phleum pratense

<400> SEQUENCE: 102
```

```
Thr Glu Glu Gln Lys Leu Ile Glu Asp Val Asn Ala Ser Phe Arg Ala
1               5                   10                  15

Ala Met Ala Thr Thr Ala Asn Val Pro Pro Ala Asp Lys Tyr Lys Thr
                20                  25                  30

Leu Glu Ala Ala Phe Thr Val Ser Ser Lys Arg Asn Leu Ala Asp Ala
            35                  40                  45

Val Ser Lys Ala Pro Gln Leu Val Pro Lys Leu Asp Glu Val Tyr Asn
50                  55                  60

Ala Ala Tyr Asn Ala Ala Asp His Ala Ala Pro Glu Asp Lys Tyr Glu
65                  70                  75                  80

Ala Phe Val Leu His Phe Ser Glu Ala Leu Arg Ile Ile Ala Gly Thr
                85                  90                  95

Pro Glu Val His Ala Val Lys Pro Gly Ala
            100                 105
```

<210> SEQ ID NO 103
<211> LENGTH: 138
<212> TYPE: PRT
<213> ORGANISM: Phleum pratense

<400> SEQUENCE: 103

```
Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
                20                  25                  30

Thr Glu Glu Gln Lys Leu Ile Glu Asp Ile Asn Ala Ser Phe Arg Ala
            35                  40                  45

Ala Met Ala Thr Thr Ala Asn Val Pro Pro Ala Asp Lys Tyr Lys Thr
50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
                100                 105                 110

Ala Phe Val Leu His Phe Ser Glu Ala Leu His Ile Ile Ala Gly Thr
            115                 120                 125

Pro Glu Val His Ala Val Lys Pro Gly Ala
            130                 135
```

<210> SEQ ID NO 104
<211> LENGTH: 132
<212> TYPE: PRT
<213> ORGANISM: Phleum pratense

<400> SEQUENCE: 104

```
Met Val Ala Met Phe Leu Ala Val Ala Val Leu Gly Leu Ala Thr
1               5                   10                  15

Ser Pro Thr Ala Glu Gly Gly Lys Ala Thr Thr Glu Glu Gln Lys Leu
                20                  25                  30

Ile Glu Asp Val Asn Ala Ser Phe Arg Ala Ala Met Ala Thr Thr Ala
            35                  40                  45

Asn Val Pro Pro Ala Asp Lys Tyr Lys Thr Phe Glu Ala Ala Phe Thr
50                  55                  60

Val Ser Ser Lys Arg Asn Leu Ala Asp Ala Val Ser Lys Ala Pro Gln
65                  70                  75                  80
```

```
Leu Val Pro Lys Leu Asp Glu Val Tyr Asn Ala Ala Tyr Asn Ala Ala
                85                  90                  95

Asp His Ala Ala Pro Glu Asp Lys Tyr Glu Ala Phe Val Leu His Phe
            100                 105                 110

Ser Glu Ala Leu Arg Ile Ile Ala Gly Thr Pro Glu Val His Ala Val
        115                 120                 125

Lys Pro Gly Ala
    130

<210> SEQ ID NO 105
<211> LENGTH: 78
<212> TYPE: PRT
<213> ORGANISM: Phleum pratense

<400> SEQUENCE: 105

Met Ala Asp Asp Met Glu Arg Ile Phe Lys Arg Phe Asp Thr Asn Gly
1               5                   10                  15

Asp Gly Lys Ile Ser Leu Ser Glu Leu Thr Asp Ala Leu Arg Thr Leu
            20                  25                  30

Gly Ser Thr Ser Ala Asp Glu Val Gln Arg Met Met Ala Glu Ile Asp
        35                  40                  45

Thr Asp Gly Asp Gly Phe Ile Asp Phe Asn Glu Phe Ile Ser Phe Cys
    50                  55                  60

Asn Ala Asn Pro Gly Leu Met Lys Asp Val Ala Lys Val Phe
65                  70                  75

<210> SEQ ID NO 106
<211> LENGTH: 131
<212> TYPE: PRT
<213> ORGANISM: Phleum pratense

<400> SEQUENCE: 106

Met Ser Trp Gln Thr Tyr Val Asp Glu His Leu Met Cys Glu Ile Glu
1               5                   10                  15

Gly His His Leu Ala Ser Ala Ala Ile Leu Gly His Asp Gly Thr Val
            20                  25                  30

Trp Ala Gln Ser Ala Asp Phe Pro Gln Phe Lys Pro Glu Glu Ile Thr
        35                  40                  45

Gly Ile Met Lys Asp Phe Asp Glu Pro Gly His Leu Ala Pro Thr Gly
    50                  55                  60

Met Phe Val Ala Gly Ala Lys Tyr Met Val Ile Gln Gly Glu Pro Gly
65                  70                  75                  80

Arg Val Ile Arg Gly Lys Lys Gly Ala Gly Gly Ile Thr Ile Lys Lys
            85                  90                  95

Thr Gly Gln Ala Leu Val Val Gly Ile Tyr Asp Glu Pro Met Thr Pro
        100                 105                 110

Gly Gln Cys Asn Met Val Val Glu Arg Leu Gly Asp Tyr Leu Val Glu
    115                 120                 125

Gln Gly Met
    130

<210> SEQ ID NO 107
<211> LENGTH: 227
<212> TYPE: PRT
<213> ORGANISM: Vespula vulgaris

<400> SEQUENCE: 107
```

Met Glu Ile Ser Gly Leu Val Tyr Leu Ile Ile Val Thr Ile Ile
1               5                   10                  15

Asp Leu Pro Tyr Gly Lys Ala Asn Asn Tyr Cys Lys Ile Lys Cys Leu
            20                  25                  30

Lys Gly Gly Val His Thr Ala Cys Lys Tyr Gly Ser Leu Lys Pro Asn
        35                  40                  45

Cys Gly Asn Lys Val Val Ser Tyr Gly Leu Thr Lys Gln Glu Lys
    50                  55                  60

Gln Asp Ile Leu Lys Glu His Asn Asp Phe Arg Gln Lys Ile Ala Arg
65                  70                  75                  80

Gly Leu Glu Thr Arg Gly Asn Pro Gly Pro Gln Pro Ala Lys Asn
                85                  90                  95

Met Lys Asn Leu Val Trp Asn Asp Glu Leu Ala Tyr Val Ala Gln Val
            100                 105                 110

Trp Ala Asn Gln Cys Gln Tyr Gly His Asp Thr Cys Arg Asp Val Ala
            115                 120                 125

Lys Tyr Gln Val Gly Gln Asn Val Ala Leu Thr Gly Ser Thr Ala Ala
        130                 135                 140

Lys Tyr Asp Asp Pro Val Lys Leu Val Lys Met Trp Glu Asp Glu Val
145                 150                 155                 160

Lys Asp Tyr Asn Pro Lys Lys Phe Ser Gly Asn Asp Phe Leu Lys
                165                 170                 175

Thr Gly His Tyr Thr Gln Met Val Trp Ala Asn Thr Lys Glu Val Gly
            180                 185                 190

Cys Gly Ser Ile Lys Tyr Ile Gln Glu Lys Trp His Lys His Tyr Leu
        195                 200                 205

Val Cys Asn Tyr Gly Pro Ser Gly Asn Phe Met Asn Glu Glu Leu Tyr
    210                 215                 220

Gln Thr Lys
225

<210> SEQ ID NO 108
<211> LENGTH: 300
<212> TYPE: PRT
<213> ORGANISM: Vespula maculifrons

<400> SEQUENCE: 108

Gly Pro Lys Cys Pro Phe Asn Ser Asp Thr Val Ser Ile Ile Glu
1               5                   10                  15

Thr Arg Glu Asn Arg Asn Arg Asp Leu Tyr Thr Leu Gln Thr Leu Gln
            20                  25                  30

Asn His Pro Glu Phe Lys Lys Lys Thr Ile Thr Arg Pro Val Val Phe
        35                  40                  45

Ile Thr His Gly Phe Thr Ser Ser Ala Ser Glu Lys Asn Phe Ile Asn
    50                  55                  60

Leu Ala Lys Ala Leu Val Asp Lys Asp Asn Tyr Met Val Ile Ser Ile
65                  70                  75                  80

Asp Trp Gln Thr Ala Ala Cys Thr Asn Glu Tyr Pro Gly Leu Lys Tyr
            85                  90                  95

Ala Tyr Tyr Pro Thr Ala Ala Ser Asn Thr Arg Leu Val Gly Gln Tyr
            100                 105                 110

Ile Ala Thr Ile Thr Gln Lys Leu Val Lys Asp Tyr Lys Ile Ser Met
            115                 120                 125

Ala Asn Ile Arg Leu Ile Gly His Ser Leu Gly Ala His Val Ser Gly
        130                 135                 140

Phe Ala Gly Lys Arg Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
            165                 170                 175

Ser Glu Arg Leu Cys Glu Thr Asp Ala Glu Tyr Val Gln Ile Ile His
        180                 185                 190

Thr Ser Asn Tyr Leu Gly Thr Glu Lys Ile Leu Gly Thr Val Asp Phe
    195                 200                 205

Tyr Met Asn Asn Gly Lys Asn Asn Pro Gly Cys Gly Arg Phe Phe Ser
210                 215                 220

Glu Val Cys Ser His Thr Arg Ala Val Ile Tyr Met Ala Glu Cys Ile
225                 230                 235                 240

Lys His Glu Cys Cys Leu Ile Gly Ile Pro Arg Ser Lys Ser Ser Gln
                245                 250                 255

Pro Ile Ser Arg Cys Thr Lys Gln Glu Cys Val Cys Val Gly Leu Asn
            260                 265                 270

Ala Lys Lys Tyr Pro Ser Arg Gly Ser Phe Tyr Val Pro Val Glu Ser
        275                 280                 285

Thr Ala Pro Phe Cys Asn Asn Lys Gly Lys Ile Ile
    290                 295                 300

<210> SEQ ID NO 109
<211> LENGTH: 336
<212> TYPE: PRT
<213> ORGANISM: Vespula vulgaris

<400> SEQUENCE: 109

Met Glu Glu Asn Met Asn Leu Lys Tyr Leu Leu Phe Val Tyr Phe
1               5                   10                  15

Val Gln Val Leu Asn Cys Cys Tyr Gly His Gly Asp Pro Leu Ser Tyr
                20                  25                  30

Glu Leu Asp Arg Gly Pro Lys Cys Pro Phe Asn Ser Asp Thr Val Ser
            35                  40                  45

Ile Ile Ile Glu Thr Arg Glu Asn Arg Asn Arg Asp Leu Tyr Thr Leu
50                  55                  60

Gln Thr Leu Gln Asn His Pro Glu Phe Lys Lys Lys Thr Ile Thr Arg
65                  70                  75                  80

Pro Val Val Phe Ile Thr His Gly Phe Thr Ser Ser Ala Ser Glu Thr
                85                  90                  95

Asn Phe Ile Asn Leu Ala Lys Ala Leu Val Asp Lys Asp Asn Tyr Met
            100                 105                 110

Val Ile Ser Ile Asp Trp Gln Thr Ala Ala Cys Thr Asn Glu Ala Ala
        115                 120                 125

Gly Leu Lys Tyr Leu Tyr Tyr Pro Thr Ala Ala Arg Asn Thr Arg Leu
130                 135                 140

Val Gly Gln Tyr Ile Ala Thr Ile Thr Gln Lys Leu Val Lys His Tyr
145                 150                 155                 160

Lys Ile Ser Met Ala Asn Ile Arg Leu Ile Gly His Ser Leu Gly Ala
                165                 170                 175

His Ala Ser Gly Phe Ala Gly Lys Lys Val Gln Glu Leu Lys Leu Gly
            180                 185                 190

Lys Tyr Ser Glu Ile Ile Gly Leu Asp Pro Ala Arg Pro Ser Phe Asp
        195                 200                 205

Ser Asn His Cys Ser Glu Arg Leu Cys Glu Thr Asp Ala Glu Tyr Val

```
              210                 215                 220
Gln Ile Ile His Thr Ser Asn Tyr Leu Gly Thr Glu Lys Thr Leu Gly
225                 230                 235                 240

Thr Val Asp Phe Tyr Met Asn Asn Gly Lys Asn Gln Pro Gly Cys Gly
                245                 250                 255

Arg Phe Phe Ser Glu Val Cys Ser His Ser Arg Ala Val Ile Tyr Met
                260                 265                 270

Ala Glu Cys Ile Lys His Glu Cys Cys Leu Ile Gly Ile Pro Lys Ser
                275                 280                 285

Lys Ser Ser Gln Pro Ile Ser Ser Cys Thr Lys Gln Glu Cys Val Cys
                290                 295                 300

Val Gly Leu Asn Ala Lys Lys Tyr Pro Ser Arg Gly Ser Phe Tyr Val
305                 310                 315                 320

Pro Val Glu Ser Thr Ala Pro Phe Cys Asn Asn Lys Gly Lys Ile Ile
                325                 330                 335

<210> SEQ ID NO 110
<211> LENGTH: 331
<212> TYPE: PRT
<213> ORGANISM: Vespula vulgaris

<400> SEQUENCE: 110

Ser Glu Arg Pro Lys Arg Val Phe Asn Ile Tyr Trp Asn Val Pro Thr
1               5                   10                  15

Phe Met Cys His Gln Tyr Asp Leu Tyr Phe Asp Glu Val Thr Asn Phe
                20                  25                  30

Asn Ile Lys Arg Asn Ser Lys Asp Asp Phe Gln Gly Asp Lys Ile Ala
                35                  40                  45

Ile Phe Tyr Asp Pro Gly Glu Phe Pro Ala Leu Leu Ser Leu Lys Asp
50                  55                  60

Gly Lys Tyr Lys Lys Arg Asn Gly Gly Val Pro Gln Glu Gly Asn Ile
65                  70                  75                  80

Thr Ile His Leu Gln Lys Phe Ile Glu Asn Leu Asp Lys Ile Tyr Pro
                85                  90                  95

Asn Arg Asn Phe Ser Gly Ile Gly Val Ile Asp Phe Glu Arg Trp Arg
                100                 105                 110

Pro Ile Phe Arg Gln Asn Trp Gly Asn Met Lys Ile His Lys Asn Phe
                115                 120                 125

Ser Ile Asp Leu Val Arg Asn Glu His Pro Thr Trp Asn Lys Lys Met
130                 135                 140

Ile Glu Leu Glu Ala Ser Lys Arg Phe Glu Lys Tyr Ala Arg Phe Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
                180                 185                 190

Leu Val Pro Glu Cys Asp Val Thr Ala Met His Glu Asn Asp Lys Met
                195                 200                 205

Ser Trp Leu Phe Asn Asn Gln Asn Val Leu Leu Pro Ser Val Tyr Val
                210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys
                245                 250                 255
```

```
Val Leu Ser Tyr Trp Trp Tyr Val Tyr Gln Asp Glu Thr Asn Thr Phe
            260                 265                 270

Leu Thr Glu Thr Asp Val Lys Lys Thr Phe Gln Glu Ile Val Ile Asn
            275                 280                 285

Gly Gly Asp Gly Ile Ile Ile Trp Gly Ser Ser Ser Asp Val Asn Ser
            290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
            325                 330

<210> SEQ ID NO 111
<211> LENGTH: 206
<212> TYPE: PRT
<213> ORGANISM: Vespula vulgaris

<400> SEQUENCE: 111

Lys Val Asn Tyr Cys Lys Ile Lys Cys Leu Lys Gly Gly Val His Thr
1               5                   10                  15

Ala Cys Lys Tyr Gly Thr Ser Thr Lys Pro Asn Cys Gly Lys Met Val
            20                  25                  30

Val Lys Ala Tyr Gly Leu Thr Glu Ala Glu Lys Gln Glu Ile Leu Lys
            35                  40                  45

Val His Asn Asp Phe Arg Gln Lys Val Ala Lys Gly Leu Glu Thr Arg
        50                  55                  60

Gly Asn Pro Gly Pro Gln Pro Pro Ala Lys Asn Met Asn Asn Leu Val
65                  70                  75                  80

Trp Asn Asp Glu Leu Ala Asn Ile Ala Gln Val Trp Ala Ser Gln Cys
                85                  90                  95

Asn Tyr Gly His Asp Thr Cys Lys Asp Thr Glu Lys Tyr Pro Val Gly
            100                 105                 110

Gln Asn Ile Ala Lys Arg Ser Thr Thr Ala Ala Leu Phe Asp Ser Pro
            115                 120                 125

Gly Lys Leu Val Lys Met Trp Glu Asn Glu Val Lys Asp Phe Asn Pro
        130                 135                 140

Asn Ile Glu Trp Ser Lys Asn Leu Lys Lys Thr Gly His Tyr Thr
145                 150                 155                 160

Gln Met Val Trp Ala Lys Thr Lys Glu Ile Gly Cys Gly Ser Val Lys
            165                 170                 175

Tyr Val Lys Asp Glu Trp Tyr Thr His Tyr Leu Val Cys Asn Tyr Gly
            180                 185                 190

Pro Ser Gly Asn Phe Arg Asn Glu Lys Leu Tyr Glu Lys Lys
            195                 200                 205

<210> SEQ ID NO 112
<211> LENGTH: 160
<212> TYPE: PRT
<213> ORGANISM: Betula pendula

<400> SEQUENCE: 112

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
            35                  40                  45
```

```
Gly Gly Pro Gly Thr Ile Lys Lys Ile Ser Phe Pro Glu Gly Phe Pro
 50                  55                  60

Phe Lys Tyr Val Lys Asp Arg Val Asp Glu Val Asp His Thr Asn Phe
 65                  70                  75                  80

Lys Tyr Asn Tyr Ser Val Ile Glu Gly Gly Pro Ile Gly Asp Thr Leu
                 85                  90                  95

Glu Lys Ile Ser Asn Glu Ile Lys Ile Val Ala Thr Pro Asp Gly Gly
                100                 105                 110

Ser Ile Leu Lys Ile Ser Asn Lys Tyr His Thr Lys Gly Asp His Glu
                115                 120                 125

Val Lys Ala Glu Gln Val Lys Ala Ser Lys Glu Met Gly Glu Thr Leu
130                 135                 140

Leu Arg Ala Val Glu Ser Tyr Leu Leu Ala His Ser Asp Ala Tyr Asn
145                 150                 155                 160

<210> SEQ ID NO 113
<211> LENGTH: 133
<212> TYPE: PRT
<213> ORGANISM: Betula pendula

<400> SEQUENCE: 113

Met Ser Trp Gln Thr Tyr Val Asp Glu His Leu Met Cys Asp Ile Asp
 1               5                  10                  15

Gly Gln Ala Ser Asn Ser Leu Ala Ser Ala Ile Val Gly His Asp Gly
                20                  25                  30

Ser Val Trp Ala Gln Ser Ser Phe Pro Gln Phe Lys Pro Gln Glu
                35                  40                  45

Ile Thr Gly Ile Met Lys Asp Phe Glu Glu Pro Gly His Leu Ala Pro
 50                  55                  60

Thr Gly Leu His Leu Gly Gly Ile Lys Tyr Met Val Ile Gln Gly Glu
 65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
                100                 105                 110

Thr Pro Gly Gln Cys Asn Met Val Val Glu Arg Leu Gly Asp Tyr Leu
                115                 120                 125

Ile Asp Gln Gly Leu
            130

<210> SEQ ID NO 114
<211> LENGTH: 205
<212> TYPE: PRT
<213> ORGANISM: Betula pendula

<400> SEQUENCE: 114

Met Pro Cys Ser Thr Glu Ala Met Glu Lys Ala Gly His Gly His Ala
 1               5                  10                  15

Ser Thr Pro Arg Lys Arg Ser Leu Asn Ser Ser Phe Arg Leu Arg
                20                  25                  30

Ser Glu Ser Leu Asn Thr Leu Arg Leu Arg Arg Ile Phe Asp Leu Phe
                35                  40                  45

Asp Lys Asn Ser Asp Gly Ile Ile Thr Val Asp Glu Leu Ser Arg Ala
                50                  55                  60

Leu Asn Leu Leu Gly Leu Glu Thr Asp Leu Ser Glu Leu Glu Ser Thr
 65                  70                  75                  80
```

```
Val Lys Ser Phe Thr Arg Glu Gly Asn Ile Gly Leu Gln Phe Glu Asp
                85                  90                  95

Phe Ile Ser Leu His Gln Ser Leu Asn Asp Ser Tyr Phe Ala Tyr Gly
            100                 105                 110

Gly Glu Asp Glu Asp Asp Asn Glu Glu Asp Met Arg Lys Ser Ile Leu
        115                 120                 125

Ser Gln Glu Glu Ala Asp Ser Phe Gly Gly Phe Lys Val Phe Asp Glu
    130                 135                 140

Asp Gly Asp Gly Tyr Ile Ser Ala Arg Glu Leu Gln Met Val Leu Gly
145                 150                 155                 160

Lys Leu Gly Phe Ser Glu Gly Ser Glu Ile Asp Arg Val Glu Lys Met
                165                 170                 175

Ile Val Ser Val Asp Ser Asn Arg Asp Gly Arg Val Asp Phe Phe Glu
            180                 185                 190

Phe Lys Asp Met Met Arg Ser Val Leu Val Arg Ser Ser
            195                 200                 205

<210> SEQ ID NO 115
<211> LENGTH: 85
<212> TYPE: PRT
<213> ORGANISM: Betula pendula

<400> SEQUENCE: 115

Met Ala Asp Asp His Pro Gln Asp Lys Ala Glu Arg Glu Arg Ile Phe
1               5                   10                  15

Lys Arg Phe Asp Ala Asn Gly Asp Gly Lys Ile Ser Ala Ala Glu Leu
                20                  25                  30

Gly Glu Ala Leu Lys Thr Leu Gly Ser Ile Thr Pro Asp Glu Val Lys
            35                  40                  45

His Met Met Ala Glu Ile Asp Thr Asp Gly Asp Gly Phe Ile Ser Phe
        50                  55                  60

Gln Glu Phe Thr Asp Phe Gly Arg Ala Asn Arg Gly Leu Leu Lys Asp
65                  70                  75                  80

Val Ala Lys Ile Phe
                85

<210> SEQ ID NO 116
<211> LENGTH: 24
<212> TYPE: PRT
<213> ORGANISM: Quercus alba
<220> FEATURE:
<221> NAME/KEY: MISC_FEATURE
<222> LOCATION: (5)..(5)
<223> OTHER INFORMATION: Xaa = unknown amino acid
<220> FEATURE:
<221> NAME/KEY: MISC_FEATURE
<222> LOCATION: (17)..(17)
<223> OTHER INFORMATION: Xaa = unknown amino acid

<400> SEQUENCE: 116

Gly Val Phe Thr Xaa Glu Ser Gln Glu Thr Ser Val Ile Ala Pro Ala
1               5                   10                  15

Xaa Leu Phe Lys Ala Leu Phe Leu
                20

<210> SEQ ID NO 117
<211> LENGTH: 40
<212> TYPE: PRT
<213> ORGANISM: Carpinus betulus
<220> FEATURE:
<221> NAME/KEY: MISC_FEATURE
```

```
<222> LOCATION: (39)..(39)
<223> OTHER INFORMATION: Xaa = unknown amino acid

<400> SEQUENCE: 117

Gly Val Phe Asn Tyr Glu Ala Glu Thr Pro Ser Val Ile Pro Ala Ala
1               5                   10                  15

Arg Leu Phe Lys Ser Tyr Val Leu Asp Gly Asp Lys Leu Ile Pro Lys
            20                  25                  30

Val Ala Pro Gln Ala Ile Xaa Lys
        35                  40

<210> SEQ ID NO 118
<211> LENGTH: 44
<212> TYPE: PRT
<213> ORGANISM: Alnus glutinosa

<400> SEQUENCE: 118

Gly Val Phe Asn Tyr Glu Ala Glu Thr Pro Ser Val Ile Pro Ala Ala
1               5                   10                  15

Arg Leu Phe Lys Ala Phe Ile Leu Asp Gly Asp Lys Leu Leu Pro Lys
            20                  25                  30

Val Ala Pro Glu Ala Val Ser Ser Val Glu Asn Ile
        35                  40

<210> SEQ ID NO 119
<211> LENGTH: 110
<212> TYPE: PRT
<213> ORGANISM: Betula pendula

<400> SEQUENCE: 119

Val Gln Cys Met Gln Val Trp Pro Pro Leu Gly Leu Lys Lys Phe Glu
1               5                   10                  15

Thr Leu Ser Tyr Leu Pro Pro Leu Ser Ser Glu Gln Leu Ala Lys Glu
            20                  25                  30

Val Asp Tyr Leu Leu Arg Lys Asn Leu Ile Pro Cys Leu Glu Phe Glu
        35                  40                  45

Leu Glu His Gly Phe Val Tyr Arg Glu His Asn Arg Ser Pro Gly Tyr
    50                  55                  60

Tyr Asp Gly Arg Tyr Trp Thr Met Trp Lys Leu Pro Met Phe Gly Cys
65                  70                  75                  80

Asn Asp Ser Ser Gln Val Leu Lys Glu Leu Glu Cys Lys Lys Ala
                85                  90                  95

Tyr Pro Ser Ala Phe Ile Arg Ile Ile Gly Phe Asp Asp Lys
            100                 105                 110

<210> SEQ ID NO 120
<211> LENGTH: 626
<212> TYPE: PRT
<213> ORGANISM: Arachis hypogaea

<400> SEQUENCE: 120

Met Arg Gly Arg Val Ser Pro Leu Met Leu Leu Leu Gly Ile Leu Val
1               5                   10                  15

Leu Ala Ser Val Ser Ala Thr His Ala Lys Ser Ser Pro Tyr Gln Lys
            20                  25                  30

Lys Thr Glu Asn Pro Cys Ala Gln Arg Cys Leu Gln Ser Cys Gln Gln
            35                  40                  45

Glu Pro Asp Asp Leu Lys Gln Lys Ala Cys Glu Ser Arg Cys Thr Lys
    50                  55                  60
```

```
Leu Glu Tyr Asp Pro Arg Cys Val Tyr Asp Pro Arg His Thr Gly
 65                  70                  75                  80

Thr Thr Asn Gln Arg Ser Pro Pro Gly Glu Arg Thr Arg Gly Arg Gln
                 85                  90                  95

Pro Gly Asp Tyr Asp Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
130                 135                 140

Arg Lys Ile Arg Pro Glu Gly Arg Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
                195                 200                 205

Leu Gln Asn His Arg Ile Val Gln Ile Glu Ala Lys Pro Asn Thr Leu
210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
            245                 250                 255

Asn Leu Asp Glu Gly His Ala Leu Arg Ile Pro Ser Gly Phe Ile Ser
                260                 265                 270

Tyr Ile Leu Asn Arg His Asp Asn Gln Asn Leu Arg Val Ala Lys Ile
                275                 280                 285

Ser Met Pro Val Asn Thr Pro Gly Gln Phe Glu Asp Phe Phe Pro Ala
290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
                340                 345                 350

Trp Ser Thr Arg Ser Ser Glu Asn Asn Glu Gly Val Ile Val Lys Val
                355                 360                 365

Ser Lys Glu His Val Glu Glu Leu Thr Lys His Ala Lys Ser Val Ser
370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
                420                 425                 430

Leu Thr Cys Val Glu Ile Lys Glu Gly Ala Leu Met Leu Pro His Phe
            435                 440                 445

Asn Ser Lys Ala Met Val Ile Val Val Val Asn Lys Gly Thr Gly Asn
            450                 455                 460

Leu Glu Leu Val Ala Val Arg Lys Glu Gln Gln Gln Arg Gly Arg Arg
465                 470                 475                 480
```

```
Glu Glu Glu Glu Asp Glu Glu Glu Glu Gly Ser Asn Arg Glu
            485             490             495
Val Arg Arg Tyr Thr Ala Arg Leu Lys Glu Gly Asp Val Phe Ile Met
        500                 505                 510
Pro Ala Ala His Pro Val Ala Ile Asn Ala Ser Ser Glu Leu His Leu
        515                 520                 525
Leu Gly Phe Gly Ile Asn Ala Glu Asn Asn His Arg Ile Phe Leu Ala
        530                 535                 540
Gly Asp Lys Asp Asn Val Ile Asp Gln Ile Glu Lys Gln Ala Lys Asp
545                 550                 555                 560
Leu Ala Phe Pro Gly Ser Gly Glu Gln Val Glu Lys Leu Ile Lys Asn
                565                 570                 575
Gln Lys Glu Ser His Phe Val Ser Ala Arg Pro Gln Ser Gln Ser Gln
            580                 585                 590
Ser Pro Ser Ser Pro Glu Lys Glu Ser Pro Glu Lys Glu Asp Gln Glu
        595                 600                 605
Glu Glu Asn Gln Gly Gly Lys Gly Pro Leu Leu Ser Ile Leu Lys Ala
        610                 615                 620
Phe Asn
625

<210> SEQ ID NO 121
<211> LENGTH: 392
<212> TYPE: PRT
<213> ORGANISM: Ambrosia artemisiifolia

<400> SEQUENCE: 121

Met Gly Ile Lys His Cys Cys Tyr Ile Leu Tyr Phe Thr Leu Ala Leu
1               5                   10                  15
Val Thr Leu Leu Gln Pro Val Arg Ser Ala Glu Asp Leu Gln Gln Ile
            20                  25                  30
Leu Pro Ser Ala Asn Glu Thr Arg Ser Leu Thr Thr Cys Gly Thr Tyr
        35                  40                  45
Asn Ile Ile Asp Gly Cys Trp Arg Gly Lys Ala Asp Trp Ala Glu Asn
    50                  55                  60
Arg Lys Ala Leu Ala Asp Cys Ala Gln Gly Phe Ala Lys Gly Thr Ile
65                  70                  75                  80
Gly Gly Lys Asp Gly Asp Ile Tyr Thr Val Thr Ser Glu Leu Asp Asp
                85                  90                  95
Asp Val Ala Asn Pro Lys Glu Gly Thr Leu Arg Phe Gly Ala Ala Gln
            100                 105                 110
Asn Arg Pro Leu Trp Ile Ile Phe Ala Arg Asp Met Val Ile Arg Leu
        115                 120                 125
Asp Arg Glu Leu Ala Ile Asn Asn Asp Lys Thr Ile Asp Gly Arg Gly
    130                 135                 140
Ala Lys Val Glu Ile Ile Asn Ala Gly Phe Ala Ile Tyr Asn Val Lys
145                 150                 155                 160
Asn Ile Ile Ile His Asn Ile Met His Asp Ile Val Asn Pro
                165                 170                 175
Gly Gly Leu Ile Lys Ser His Asp Gly Pro Pro Val Pro Arg Lys Gly
            180                 185                 190
Ser Asp Gly Asp Ala Ile Gly Ile Ser Gly Gly Ser Gln Ile Trp Ile
        195                 200                 205
Asp His Cys Ser Leu Ser Lys Ala Val Asp Gly Leu Ile Asp Ala Lys
    210                 215                 220
```

His Gly Ser Thr His Phe Thr Val Ser Asn Cys Leu Phe Thr Gln His
225                 230                 235                 240

Gln Tyr Leu Leu Leu Phe Trp Asp Phe Asp Glu Arg Gly Met Leu Cys
            245                 250                 255

Thr Val Ala Phe Asn Lys Phe Thr Asp Asn Val Asp Gln Arg Met Pro
        260                 265                 270

Asn Leu Arg His Gly Phe Val Gln Val Val Asn Asn Tyr Glu Arg
    275                 280                 285

Trp Gly Ser Tyr Ala Leu Gly Gly Ser Ala Gly Pro Thr Ile Leu Ser
290                 295                 300

Gln Gly Asn Arg Phe Leu Ala Ser Asp Ile Lys Lys Glu Val Val Gly
305                 310                 315                 320

Arg Tyr Gly Glu Ser Ala Met Ser Glu Ser Ile Asn Trp Asn Trp Arg
                325                 330                 335

Ser Tyr Met Asp Val Phe Glu Asn Gly Ala Ile Phe Val Pro Ser Gly
            340                 345                 350

Val Asp Pro Val Leu Thr Pro Glu Gln Asn Ala Gly Met Ile Pro Ala
        355                 360                 365

Glu Pro Gly Glu Ala Val Leu Arg Leu Thr Ser Ala Gly Val Leu
    370                 375                 380

Ser Cys Gln Pro Gly Ala Pro Cys
385                 390

<210> SEQ ID NO 122
<211> LENGTH: 397
<212> TYPE: PRT
<213> ORGANISM: Ambrosia artemisiifolia

<400> SEQUENCE: 122

Met Gly Ile Lys His Cys Cys Tyr Ile Leu Tyr Phe Thr Leu Ala Leu
1               5                   10                  15

Val Thr Leu Val Gln Ala Gly Arg Leu Gly Glu Glu Val Asp Ile Leu
            20                  25                  30

Pro Ser Pro Asn Asp Thr Arg Arg Ser Leu Gln Gly Cys Glu Ala His
        35                  40                  45

Asn Ile Ile Asp Lys Cys Trp Arg Cys Lys Pro Asp Trp Ala Glu Asn
    50                  55                  60

Arg Gln Ala Leu Gly Asn Cys Ala Gln Gly Phe Gly Lys Ala Thr His
65                  70                  75                  80

Gly Gly Lys Trp Gly Asp Ile Tyr Met Val Thr Ser Asp Gln Asp Asp
                85                  90                  95

Asp Val Val Asn Pro Lys Glu Gly Thr Leu Arg Phe Gly Ala Thr Gln
            100                 105                 110

Asp Arg Pro Leu Trp Ile Ile Phe Gln Arg Asp Met Ile Ile Tyr Leu
        115                 120                 125

Gln Gln Glu Met Val Val Thr Ser Asp Lys Thr Ile Asp Gly Arg Gly
    130                 135                 140

Ala Lys Val Glu Leu Val Tyr Gly Gly Ile Thr Leu Met Asn Val Lys
145                 150                 155                 160

Asn Val Ile Ile His Asn Ile Asp Ile His Asp Val Arg Val Leu Pro
                165                 170                 175

Gly Gly Arg Ile Lys Ser Asn Gly Gly Pro Ala Ile Pro Arg His Gln
            180                 185                 190

Ser Asp Gly Asp Ala Ile His Val Thr Gly Ser Ser Asp Ile Trp Ile

```
                195                 200                 205
Asp His Cys Thr Leu Ser Lys Ser Phe Asp Gly Leu Val Asp Val Asn
    210                 215                 220

Trp Gly Ser Thr Gly Val Thr Ile Ser Asn Cys Lys Phe Thr His His
225                 230                 235                 240

Glu Lys Ala Val Leu Leu Gly Ala Ser Asp Thr His Phe Gln Asp Leu
                245                 250                 255

Lys Met His Val Thr Leu Ala Tyr Asn Ile Phe Thr Asn Thr Val His
                260                 265                 270

Glu Arg Met Pro Arg Cys Arg Phe Gly Phe Phe Gln Ile Val Asn Asn
            275                 280                 285

Phe Tyr Asp Arg Trp Asp Lys Tyr Ala Ile Gly Gly Ser Ser Asn Pro
        290                 295                 300

Thr Ile Leu Ser Gln Gly Asn Lys Phe Val Ala Pro Asp Phe Ile Tyr
305                 310                 315                 320

Lys Lys Asn Val Cys Leu Arg Thr Gly Ala Gln Glu Pro Glu Trp Met
                325                 330                 335

Thr Trp Asn Trp Arg Thr Gln Asn Asp Val Leu Glu Asn Gly Ala Ile
                340                 345                 350

Phe Val Ala Ser Gly Ser Asp Pro Val Leu Thr Ala Glu Gln Asn Ala
            355                 360                 365

Gly Met Met Gln Ala Glu Pro Gly Asp Met Val Pro Gln Leu Thr Met
        370                 375                 380

Asn Ala Gly Val Leu Thr Cys Ser Pro Gly Ala Pro Cys
385                 390                 395

<210> SEQ ID NO 123
<211> LENGTH: 397
<212> TYPE: PRT
<213> ORGANISM: Ambrosia artemisiifolia

<400> SEQUENCE: 123

Met Gly Ile Lys Gln Cys Cys Tyr Ile Leu Tyr Phe Thr Leu Ala Leu
1               5                   10                  15

Val Ala Leu Leu Gln Pro Val Arg Ser Ala Glu Gly Val Gly Glu Ile
            20                  25                  30

Leu Pro Ser Val Asn Glu Thr Arg Ser Leu Gln Ala Cys Glu Ala Leu
        35                  40                  45

Asn Ile Ile Asp Lys Cys Trp Arg Gly Lys Ala Asp Trp Glu Asn Asn
    50                  55                  60

Arg Gln Ala Leu Ala Asp Cys Ala Gln Gly Phe Ala Lys Gly Thr Tyr
65                  70                  75                  80

Gly Gly Lys Trp Gly Asp Val Tyr Thr Val Thr Ser Asn Leu Asp Asp
                85                  90                  95

Asp Val Ala Asn Pro Lys Glu Gly Thr Leu Arg Phe Ala Ala Ala Gln
            100                 105                 110

Asn Arg Pro Leu Trp Ile Ile Phe Lys Asn Asp Met Val Ile Asn Leu
        115                 120                 125

Asn Gln Glu Leu Val Val Asn Ser Asp Lys Thr Ile Asp Gly Arg Gly
    130                 135                 140

Val Lys Val Glu Ile Ile Asn Gly Gly Leu Thr Leu Met Asn Val Lys
145                 150                 155                 160

Asn Ile Ile Ile His Asn Ile Asn Ile His Asp Val Lys Val Leu Pro
                165                 170                 175
```

```
Gly Gly Met Ile Lys Ser Asn Asp Gly Pro Pro Ile Leu Arg Gln Ala
            180                 185                 190

Ser Asp Gly Asp Thr Ile Asn Val Ala Gly Ser Ser Gln Ile Trp Ile
        195                 200                 205

Asp His Cys Ser Leu Ser Lys Ser Phe Asp Gly Leu Val Asp Val Thr
    210                 215                 220

Leu Gly Ser Thr His Val Thr Ile Ser Asn Cys Lys Phe Thr Gln Gln
225                 230                 235                 240

Ser Lys Ala Ile Leu Leu Gly Ala Asp Asp Thr His Val Gln Asp Lys
                245                 250                 255

Gly Met Leu Ala Thr Val Ala Phe Asn Met Phe Thr Asp Asn Val Asp
            260                 265                 270

Gln Arg Met Pro Arg Cys Arg Phe Gly Phe Phe Gln Val Val Asn Asn
        275                 280                 285

Asn Tyr Asp Arg Trp Gly Thr Tyr Ala Ile Gly Gly Ser Ser Ala Pro
    290                 295                 300

Thr Ile Leu Cys Gln Gly Asn Arg Phe Leu Ala Pro Asp Asp Gln Ile
305                 310                 315                 320

Lys Lys Asn Val Leu Ala Arg Thr Gly Thr Gly Ala Ala Glu Ser Met
                325                 330                 335

Ala Trp Asn Trp Arg Ser Asp Lys Asp Leu Leu Glu Asn Gly Ala Ile
            340                 345                 350

Phe Val Thr Ser Gly Ser Asp Pro Val Leu Thr Pro Val Gln Ser Ala
        355                 360                 365

Gly Met Ile Pro Ala Glu Pro Gly Glu Ala Ala Ile Lys Leu Thr Ser
    370                 375                 380

Ser Ala Gly Val Phe Ser Cys His Pro Gly Ala Pro Cys
385                 390                 395

<210> SEQ ID NO 124
<211> LENGTH: 398
<212> TYPE: PRT
<213> ORGANISM: Ambrosia artemisiifolia

<400> SEQUENCE: 124

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Val Glu Glu Phe
            20                  25                  30

Leu Pro Ser Ala Asn Glu Thr Arg Arg Ser Leu Lys Ala Cys Glu Ala
        35                  40                  45

His Asn Ile Ile Asp Lys Cys Trp Arg Cys Lys Ala Asp Trp Ala Asn
    50                  55                  60

Asn Arg Gln Ala Leu Ala Asp Cys Ala Gln Gly Phe Ala Lys Gly Thr
65                  70                  75                  80

Tyr Gly Gly Lys His Gly Asp Val Tyr Thr Val Thr Ser Asp Lys Asp
                85                  90                  95

Asp Asp Val Ala Asn Pro Lys Glu Gly Thr Leu Arg Phe Ala Ala Ala
            100                 105                 110

Gln Asn Arg Pro Leu Trp Ile Ile Phe Lys Arg Asn Met Val Ile His
        115                 120                 125

Leu Asn Gln Glu Leu Val Val Asn Ser Asp Lys Thr Ile Asp Gly Arg
    130                 135                 140

Gly Val Lys Val Asn Ile Val Asn Ala Gly Leu Thr Leu Met Asn Val
145                 150                 155                 160
```

```
Lys Asn Ile Ile Ile His Asn Ile Asn Ile His Asp Ile Lys Val Cys
                165                 170                 175

Pro Gly Gly Met Ile Lys Ser Asn Asp Gly Pro Pro Ile Leu Arg Gln
            180                 185                 190

Gln Ser Asp Gly Asp Ala Ile Asn Val Ala Gly Ser Ser Gln Ile Trp
        195                 200                 205

Ile Asp His Cys Ser Leu Ser Lys Ala Ser Asp Gly Leu Leu Asp Ile
    210                 215                 220

Thr Leu Gly Ser Ser His Val Thr Val Ser Asn Cys Lys Phe Thr Gln
225                 230                 235                 240

His Gln Phe Val Leu Leu Leu Gly Ala Asp Asp Thr His Tyr Gln Asp
                245                 250                 255

Lys Gly Met Leu Ala Thr Val Ala Phe Asn Met Phe Thr Asp His Val
            260                 265                 270

Asp Gln Arg Met Pro Arg Cys Arg Phe Gly Phe Phe Gln Val Val Asn
        275                 280                 285

Asn Asn Tyr Asp Arg Trp Gly Thr Tyr Ala Ile Gly Gly Ser Ser Ala
    290                 295                 300

Pro Thr Ile Leu Ser Gln Gly Asn Arg Phe Phe Ala Pro Asp Asp Ile
305                 310                 315                 320

Ile Lys Lys Asn Val Leu Ala Arg Thr Gly Thr Gly Asn Ala Glu Ser
                325                 330                 335

Met Ser Trp Asn Trp Arg Thr Asp Arg Asp Leu Leu Glu Asn Gly Ala
            340                 345                 350

Ile Phe Leu Pro Ser Gly Ser Asp Pro Val Leu Thr Pro Glu Gln Lys
        355                 360                 365

Ala Gly Met Ile Pro Ala Glu Pro Gly Glu Ala Val Leu Arg Leu Thr
    370                 375                 380

Ser Ser Ala Gly Val Leu Ser Cys His Gln Gly Ala Pro Cys
385                 390                 395

<210> SEQ ID NO 125
<211> LENGTH: 396
<212> TYPE: PRT
<213> ORGANISM: Ambrosia artemisiifolia

<400> SEQUENCE: 125

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
            20                  25                  30

Leu Pro Val Asn Glu Thr Arg Arg Leu Thr Thr Ser Gly Ala Tyr Asn
        35                  40                  45

Ile Ile Asp Gly Cys Trp Arg Gly Lys Ala Asp Trp Ala Glu Asn Arg
    50                  55                  60

Lys Ala Leu Ala Asp Cys Ala Gln Gly Phe Gly Lys Gly Thr Val Gly
65                  70                  75                  80

Gly Lys Asp Gly Asp Ile Tyr Thr Val Thr Ser Glu Leu Asp Asp
                85                  90                  95

Val Ala Asn Pro Lys Glu Gly Thr Leu Arg Phe Gly Ala Ala Gln Asn
            100                 105                 110

Arg Pro Leu Trp Ile Ile Phe Glu Arg Asp Met Val Ile Arg Leu Asp
        115                 120                 125

Lys Glu Met Val Val Asn Ser Asp Lys Thr Ile Asp Gly Arg Gly Ala
```

```
            130                 135                 140
Lys Val Glu Ile Ile Asn Ala Gly Phe Thr Leu Asn Gly Val Lys Asn
145                 150                 155                 160

Val Ile Ile His Asn Ile Asn Met His Asp Val Lys Val Asn Pro Gly
                165                 170                 175

Gly Leu Ile Lys Ser Asn Asp Gly Pro Ala Ala Pro Arg Ala Gly Ser
            180                 185                 190

Asp Gly Asp Ala Ile Ser Ile Ser Gly Ser Ser Gln Ile Trp Ile Asp
        195                 200                 205

His Cys Ser Leu Ser Lys Ser Val Asp Gly Leu Val Asp Ala Lys Leu
    210                 215                 220

Gly Thr Thr Arg Leu Thr Val Ser Asn Ser Leu Phe Thr Gln His Gln
225                 230                 235                 240

Phe Val Leu Leu Phe Gly Ala Gly Asp Glu Asn Ile Glu Asp Arg Gly
                245                 250                 255

Met Leu Ala Thr Val Ala Phe Asn Thr Phe Thr Asp Asn Val Asp Gln
            260                 265                 270

Arg Met Pro Arg Cys Arg His Gly Phe Phe Gln Val Val Asn Asn Asn
        275                 280                 285

Tyr Asp Lys Trp Gly Ser Tyr Ala Ile Gly Gly Ser Ala Ser Pro Thr
    290                 295                 300

Ile Leu Ser Gln Gly Asn Arg Phe Cys Ala Pro Asp Glu Arg Ser Lys
305                 310                 315                 320

Lys Asn Val Leu Gly Arg His Gly Glu Ala Ala Ala Glu Ser Met Lys
                325                 330                 335

Trp Asn Trp Arg Thr Asn Lys Asp Val Leu Glu Asn Gly Ala Ile Phe
            340                 345                 350

Val Ala Ser Gly Val Asp Pro Val Leu Thr Pro Glu Gln Ser Ala Gly
        355                 360                 365

Met Ile Pro Ala Glu Pro Gly Glu Ser Ala Leu Ser Leu Thr Ser Ser
    370                 375                 380

Ala Gly Val Leu Ser Cys Gln Pro Gly Ala Pro Cys
385                 390                 395

<210> SEQ ID NO 126
<211> LENGTH: 373
<212> TYPE: PRT
<213> ORGANISM: Cryptomeria japonica

<400> SEQUENCE: 126

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Pro Val Asn Pro Gly Thr Leu Arg Tyr
65                  70                  75                  80

Gly Ala Thr Arg Asp Arg Pro Leu Trp Ile Ile Phe Ser Gly Asn Met
                85                  90                  95

Asn Ile Lys Leu Lys Met Pro Met Tyr Ile Ala Gly Tyr Lys Thr Phe
            100                 105                 110
```

```
Asp Gly Arg Gly Ala Gln Val Tyr Ile Gly Asn Gly Pro Cys Val
            115                 120                 125

Phe Ile Lys Arg Val Ser Asn Val Ile His Gly Leu Tyr Leu Tyr
        130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190

Asp Gly Leu Val Asp Val Thr Leu Thr Ser Thr Gly Val Thr Ile Ser
        195                 200                 205

Asn Asn Leu Phe Phe Asn His His Lys Val Met Ser Leu Gly His Asp
    210                 215                 220

Asp Ala Tyr Ser Asp Asp Lys Ser Met Lys Val Thr Val Ala Phe Asn
225                 230                 235                 240

Gln Phe Gly Pro Asn Cys Gly Gln Arg Met Pro Arg Ala Arg Tyr Gly
                245                 250                 255

Leu Val His Val Ala Asn Asn Asn Tyr Asp Pro Trp Thr Ile Tyr Ala
            260                 265                 270

Ile Gly Gly Ser Ser Asn Pro Thr Ile Leu Ser Glu Gly Asn Ser Phe
        275                 280                 285

Thr Ala Pro Asn Glu Ser Tyr Lys Lys Gln Val Thr Ile Arg Ile Gly
    290                 295                 300

Cys Lys Thr Ser Ser Cys Ser Asn Trp Val Trp Gln Ser Thr Gln
305                 310                 315                 320

Asp Val Phe Tyr Asn Gly Ala Tyr Phe Val Ser Ser Gly Lys Tyr Glu
                325                 330                 335

Gly Gly Asn Ile Tyr Thr Lys Lys Glu Ala Phe Asn Val Glu Asn Gly
            340                 345                 350

Asn Ala Thr Pro His Leu Thr Gln Asn Ala Gly Val Leu Thr Cys Ser
        355                 360                 365

Leu Ser Lys Arg Cys
    370

<210> SEQ ID NO 127
<211> LENGTH: 374
<212> TYPE: PRT
<213> ORGANISM: Cryptomeria japonica

<400> SEQUENCE: 127

Met Asp Ser Pro Cys Leu Val Ala Leu Leu Val Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
            100                 105                 110
```

```
Phe Asp Gly Arg Gly Ala Gln Val Tyr Ile Gly Asn Gly Gly Pro Cys
            115                 120                 125

Val Phe Ile Lys Arg Val Ser Asn Val Ile Ile His Gly Leu His Leu
130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Ser Ser Thr Gly Val Thr Ile
            195                 200                 205

Ser Asn Asn Leu Phe Phe Asn His His Lys Val Met Leu Leu Gly His
210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Asn Tyr Asp Pro Trp Thr Ile Tyr
            260                 265                 270

Ala Ile Gly Gly Ser Ser Asn Pro Thr Ile Leu Ser Glu Gly Asn Ser
            275                 280                 285

Phe Thr Ala Pro Asn Glu Ser Tyr Lys Lys Gln Val Thr Ile Arg Ile
            290                 295                 300

Gly Cys Lys Thr Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
            340                 345                 350

Gly Asn Ala Thr Pro Gln Leu Thr Lys Asn Ala Gly Val Leu Thr Cys
            355                 360                 365

Ser Leu Ser Lys Arg Cys
    370

<210> SEQ ID NO 128
<211> LENGTH: 514
<212> TYPE: PRT
<213> ORGANISM: Cryptomeria japonica

<400> SEQUENCE: 128

Met Ala Met Lys Leu Ile Ala Pro Met Ala Phe Leu Ala Met Gln Leu
1               5                   10                  15

Ile Ile Met Ala Ala Ala Glu Asp Gln Ser Ala Gln Ile Met Leu Asp
            20                  25                  30

Ser Val Val Glu Lys Tyr Leu Arg Ser Asn Arg Ser Leu Arg Lys Val
            35                  40                  45

Glu His Ser Arg His Asp Ala Ile Asn Ile Phe Asn Val Glu Lys Tyr
50                  55                  60

Gly Ala Val Gly Asp Gly Lys His Asp Cys Thr Glu Ala Phe Ser Thr
65                  70                  75                  80

Ala Trp Gln Ala Ala Cys Lys Asn Pro Ser Ala Met Leu Leu Val Pro
                85                  90                  95

Gly Ser Lys Lys Phe Val Val Asn Asn Leu Phe Phe Asn Gly Pro Cys
```

```
                100                 105                 110
Gln Pro His Phe Thr Phe Lys Val Asp Gly Ile Ile Ala Ala Tyr Gln
            115                 120                 125

Asn Pro Ala Ser Trp Lys Asn Arg Ile Trp Leu Gln Phe Ala Lys
        130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Gly Ile Ser Ile
    210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ile Gln Leu Lys Cys
    370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
        435                 440                 445

Met Val Glu Asn Met Arg Ala Tyr Asp Lys Gly Asn Arg Thr Arg Ile
    450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Ile Cys Ser Cys His Gly Lys Ile Tyr
            500                 505                 510

His Pro
```

<210> SEQ ID NO 129
<211> LENGTH: 514
<212> TYPE: PRT
<213> ORGANISM: Cryptomeria japonica

<400> SEQUENCE: 129

```
Met Ala Met Lys Phe Ile Ala Pro Met Ala Phe Val Ala Met Gln Leu
1               5                   10                  15

Ile Ile Met Ala Ala Glu Asp Gln Ser Ala Gln Ile Met Leu Asp
            20                  25                  30

Ser Asp Ile Glu Gln Tyr Leu Arg Ser Asn Arg Ser Leu Arg Lys Val
            35                  40                  45

Glu His Ser Arg His Asp Ala Ile Asn Ile Phe Asn Val Glu Lys Tyr
        50                  55                  60

Gly Ala Val Gly Asp Gly Lys His Asp Cys Thr Glu Ala Phe Ser Thr
65                  70                  75                  80

Ala Trp Gln Ala Ala Cys Lys Lys Pro Ser Ala Met Leu Leu Val Pro
                85                  90                  95

Gly Asn Lys Lys Phe Val Val Asn Asn Leu Phe Phe Asn Gly Pro Cys
            100                 105                 110

Gln Pro His Phe Thr Phe Lys Val Asp Gly Ile Ile Ala Ala Tyr Gln
        115                 120                 125

Asn Pro Ala Ser Trp Lys Asn Asn Arg Ile Trp Leu Gln Phe Ala Lys
    130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Ile Gly Ile Ser Ile
    210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ala Ile Gln Leu Lys Cys
    370                 375                 380
```

```
Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
            405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
            435                 440                 445

Met Val Lys Asn Met Gly Ala Tyr Asp Lys Gly Asn Arg Thr Arg Ile
        450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Met Cys Ser Arg His Gly Lys Ile Tyr
                500                 505                 510

His Pro

<210> SEQ ID NO 130
<211> LENGTH: 373
<212> TYPE: PRT
<213> ORGANISM: Cryptomeria japonica

<400> SEQUENCE: 130

Met Asp Ser Pro Cys Leu Val Ala Leu Leu Val Leu Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Lys Gly Gly Asp Leu Tyr Thr Val
    50                  55                  60

Thr Asn Ser Asp Asp Pro Val Asn Pro Gly Thr Leu Arg Tyr
65              70                  75                  80

Gly Ala Thr Arg Asp Arg Pro Leu Trp Ile Ile Phe Ser Gly Asn Met
                85                  90                  95

Asn Ile Lys Leu Lys Met Pro Met Tyr Ile Ala Gly Tyr Lys Thr Phe
            100                 105                 110

Asp Gly Arg Gly Ala Gln Val Tyr Ile Gly Asn Gly Gly Pro Cys Val
            115                 120                 125

Phe Ile Lys Arg Val Ser Asn Val Ile Ile His Gly Leu His Leu Tyr
130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190

Asp Gly Leu Val Asp Val Thr Leu Ser Ser Thr Gly Val Thr Ile Ser
            195                 200                 205

Asn Asn Leu Phe Phe Asn His His Lys Val Met Leu Leu Gly His Asp
        210                 215                 220

Asp Ala Tyr Ser Asp Asp Lys Ser Met Lys Val Thr Val Ala Phe Asn
225                 230                 235                 240
```

```
Gln Phe Gly Pro Asn Cys Gly Gln Arg Met Pro Arg Ala Arg Tyr Gly
                245                 250                 255

Leu Val His Val Ala Asn Asn Tyr Asp Pro Trp Thr Ile Tyr Ala
            260                 265                 270

Ile Gly Gly Ser Ser Asn Pro Thr Ile Leu Ser Glu Gly Asn Ser Phe
            275                 280                 285

Thr Ala Pro Asn Glu Ser Tyr Lys Lys Gln Val Thr Ile Arg Ile Gly
        290                 295                 300

Cys Lys Thr Ser Ser Ser Cys Ser Asn Trp Val Trp Gln Ser Thr Gln
305                 310                 315                 320

Asp Val Phe Tyr Asn Gly Ala Tyr Phe Val Ser Ser Gly Lys Tyr Glu
                325                 330                 335

Gly Gly Asn Ile Tyr Thr Lys Lys Glu Ala Phe Asn Val Glu Asn Gly
            340                 345                 350

Asn Ala Thr Pro Gln Leu Thr Lys Asn Ala Gly Val Leu Thr Cys Ser
            355                 360                 365

Leu Ser Lys Arg Cys
    370

<210> SEQ ID NO 131
<211> LENGTH: 374
<212> TYPE: PRT
<213> ORGANISM: Cryptomeria japonica

<400> SEQUENCE: 131

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Pro Val Asn Pro Ala Pro Gly Thr Leu Arg
65              70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Gly Pro Cys
        115                 120                 125

Val Phe Ile Lys Arg Val Ser Asn Val Ile Ile His Gly Leu Tyr Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Thr Ser Thr Gly Val Thr Ile
        195                 200                 205

Ser Asn Asn Leu Phe Phe Asn His His Lys Val Met Ser Leu Gly His
    210                 215                 220

Asp Asp Ala Tyr Ser Asp Asp Lys Ser Met Lys Val Thr Val Ala Phe
```

```
            225                 230                 235                 240
Asn Gln Phe Gly Pro Asn Cys Gly Gln Arg Met Pro Arg Ala Arg Tyr
                    245                 250                 255

Gly Leu Val His Val Ala Asn Asn Tyr Asp Pro Trp Thr Ile Tyr
            260                 265                 270

Ala Ile Gly Gly Ser Ser Asn Pro Thr Ile Leu Ser Glu Gly Asn Ser
            275                 280                 285

Phe Thr Ala Pro Asn Glu Ser Tyr Lys Lys Gln Val Thr Ile Arg Ile
        290                 295                 300

Gly Cys Lys Thr Ser Ser Cys Ser Asn Trp Val Trp Gln Ser Thr
305                 310                 315                 320

Gln Asp Val Phe Tyr Asn Gly Ala Tyr Phe Val Ser Gly Lys Tyr
                325                 330                 335

Glu Gly Gly Asn Ile Tyr Thr Lys Lys Glu Ala Phe Asn Val Glu Asn
            340                 345                 350

Gly Asn Ala Thr Pro His Leu Thr Gln Asn Ala Gly Val Leu Thr Cys
            355                 360                 365

Ser Leu Ser Lys Arg Cys
    370

<210> SEQ ID NO 132
<211> LENGTH: 174
<212> TYPE: PRT
<213> ORGANISM: Canis familiaris

<400> SEQUENCE: 132

Met Lys Thr Leu Leu Thr Ile Gly Phe Ser Leu Ile Ala Ile Leu
1               5                   10                  15

Gln Ala Gln Asp Thr Pro Ala Leu Gly Lys Asp Thr Val Ala Val Ser
            20                  25                  30

Gly Lys Trp Tyr Leu Lys Ala Met Thr Ala Asp Gln Glu Val Pro Glu
        35                  40                  45

Lys Pro Asp Ser Val Thr Pro Met Ile Leu Lys Ala Gln Lys Gly Gly
    50                  55                  60

Asn Leu Glu Ala Lys Ile Thr Met Leu Thr Asn Gly Gln Cys Gln Asn
65                  70                  75                  80

Ile Thr Val Val Leu His Lys Thr Ser Glu Pro Gly Lys Tyr Thr Ala
                85                  90                  95

Tyr Glu Gly Gln Arg Val Val Phe Ile Gln Pro Ser Pro Val Arg Asp
            100                 105                 110

His Tyr Ile Leu Tyr Cys Glu Gly Glu Leu His Gly Arg Gln Ile Arg
        115                 120                 125

Met Ala Lys Leu Leu Gly Arg Asp Pro Glu Gln Ser Gln Glu Ala Leu
    130                 135                 140

Glu Asp Phe Arg Glu Phe Ser Arg Ala Lys Gly Leu Asn Gln Glu Ile
145                 150                 155                 160

Leu Glu Leu Ala Gln Ser Glu Thr Cys Ser Pro Gly Gly Gln
                165                 170

<210> SEQ ID NO 133
<211> LENGTH: 24
<212> TYPE: PRT
<213> ORGANISM: Canis familiaris

<400> SEQUENCE: 133

Glu Ala Tyr Lys Ser Glu Ile Ala His Arg Tyr Asn Asp Leu Gly Glu
```

```
            1               5                  10                 15
Glu His Phe Arg Gly Leu Val Leu
                20
```

<210> SEQ ID NO 134
<211> LENGTH: 265
<212> TYPE: PRT
<213> ORGANISM: Canis familiaris

<400> SEQUENCE: 134

```
Leu Ser Ser Ala Lys Glu Arg Phe Lys Cys Ala Ser Leu Gln Lys Phe
1               5                   10                  15

Gly Asp Arg Ala Phe Lys Ala Trp Ser Val Ala Arg Leu Ser Gln Arg
                20                  25                  30

Phe Pro Lys Ala Asp Phe Ala Glu Ile Ser Lys Val Val Thr Asp Leu
            35                  40                  45

Thr Lys Val His Lys Glu Cys Cys His Gly Asp Leu Leu Glu Cys Ala
        50                  55                  60

Asp Asp Arg Ala Asp Leu Ala Lys Tyr Met Cys Glu Asn Gln Asp Ser
65                  70                  75                  80

Ile Ser Thr Lys Leu Lys Glu Cys Cys Asp Lys Pro Val Leu Glu Lys
                85                  90                  95

Ser Gln Cys Leu Ala Glu Val Glu Arg Asp Glu Leu Pro Gly Asp Leu
            100                 105                 110

Pro Ser Leu Ala Ala Asp Phe Val Glu Asp Lys Glu Val Cys Lys Asn
        115                 120                 125

Tyr Gln Glu Ala Lys Asp Val Phe Leu Gly Thr Phe Leu Tyr Glu Tyr
    130                 135                 140

Ser Arg Arg His Pro Glu Tyr Ser Val Ser Leu Leu Leu Arg Leu Ala
145                 150                 155                 160

Lys Glu Tyr Glu Ala Thr Leu Glu Lys Cys Cys Ala Thr Asp Asp Pro
                165                 170                 175

Pro Thr Cys Tyr Ala Lys Val Leu Asp Glu Phe Lys Pro Leu Val Asp
            180                 185                 190

Glu Pro Gln Asn Leu Val Lys Thr Asn Cys Glu Leu Phe Glu Lys Leu
        195                 200                 205

Gly Glu Tyr Gly Phe Gln Asn Ala Leu Leu Val Arg Tyr Thr Lys Lys
    210                 215                 220

Ala Pro Gln Val Ser Thr Pro Thr Leu Val Val Glu Val Ser Arg Lys
225                 230                 235                 240

Leu Gly Lys Val Gly Thr Lys Cys Cys Lys Lys Pro Glu Ser Glu Arg
                245                 250                 255

Met Ser Cys Ala Asp Asp Phe Leu Ser
            260                 265
```

<210> SEQ ID NO 135
<211> LENGTH: 180
<212> TYPE: PRT
<213> ORGANISM: Canis familiaris

<400> SEQUENCE: 135

```
Met Gln Leu Leu Leu Leu Thr Val Gly Leu Ala Leu Ile Cys Gly Leu
1               5                   10                  15

Gln Ala Gln Glu Gly Asn His Glu Glu Pro Gln Gly Gly Leu Glu Glu
                20                  25                  30

Leu Ser Gly Arg Trp His Ser Val Ala Leu Ala Ser Asn Lys Ser Asp
```

```
                 35                  40                  45
Leu Ile Lys Pro Trp Gly His Phe Arg Val Phe Ile His Ser Met Ser
 50                  55                  60

Ala Lys Asp Gly Asn Leu His Gly Asp Ile Leu Ile Pro Gln Asp Gly
 65                  70                  75                  80

Gln Cys Glu Lys Val Ser Leu Thr Ala Phe Lys Thr Ala Thr Ser Asn
                 85                  90                  95

Lys Phe Asp Leu Glu Tyr Trp Gly His Asn Asp Leu Tyr Leu Ala Glu
                100                 105                 110

Val Asp Pro Lys Ser Tyr Leu Ile Leu Tyr Met Ile Asn Gln Tyr Asn
                115                 120                 125

Asp Asp Thr Ser Leu Val Ala His Leu Met Val Arg Asp Leu Ser Arg
            130                 135                 140

Gln Gln Asp Phe Leu Pro Ala Phe Glu Ser Val Cys Glu Asp Ile Gly
145                 150                 155                 160

Leu His Lys Asp Gln Ile Val Val Leu Ser Asp Asp Arg Cys Gln
                165                 170                 175

Gly Ser Arg Asp
            180
```

<210> SEQ ID NO 136
<211> LENGTH: 187
<212> TYPE: PRT
<213> ORGANISM: Equus caballus

<400> SEQUENCE: 136

```
Met Lys Leu Leu Leu Leu Cys Leu Gly Leu Ile Leu Val Cys Ala Gln
  1               5                  10                  15

Gln Glu Glu Asn Ser Asp Val Ala Ile Arg Asn Phe Asp Ile Ser Lys
                 20                  25                  30

Ile Ser Gly Glu Trp Tyr Ser Ile Phe Leu Ala Ser Asp Val Lys Glu
             35                  40                  45

Lys Ile Glu Glu Asn Gly Ser Met Arg Val Phe Val Asp Val Ile Arg
 50                  55                  60

Ala Leu Asp Asn Ser Ser Leu Tyr Ala Glu Tyr Gln Thr Lys Val Asn
 65                  70                  75                  80

Gly Glu Cys Thr Glu Phe Pro Met Val Phe Asp Lys Thr Glu Glu Asp
                 85                  90                  95

Gly Val Tyr Ser Leu Asn Tyr Asp Gly Tyr Asn Val Phe Arg Ile Ser
                100                 105                 110

Glu Phe Glu Asn Asp Glu His Ile Ile Leu Tyr Leu Val Asn Phe Asp
                115                 120                 125

Lys Asp Arg Pro Phe Gln Leu Phe Glu Phe Tyr Ala Arg Glu Pro Asp
            130                 135                 140

Val Ser Pro Glu Ile Lys Glu Glu Phe Val Lys Ile Val Gln Lys Arg
145                 150                 155                 160

Gly Ile Val Lys Glu Asn Ile Ile Asp Leu Thr Lys Ile Asp Arg Cys
                165                 170                 175

Phe Gln Leu Arg Gly Asn Gly Val Ala Gln Ala
            180                 185
```

<210> SEQ ID NO 137
<211> LENGTH: 29
<212> TYPE: PRT
<213> ORGANISM: Equus caballus
<220> FEATURE:

```
<221> NAME/KEY: MISC_FEATURE
<222> LOCATION: (3)..(3)
<223> OTHER INFORMATION: Xaa = unknown amino acid
<220> FEATURE:
<221> NAME/KEY: MISC_FEATURE
<222> LOCATION: (28)..(28)
<223> OTHER INFORMATION: Xaa = unknown amino acid

<400> SEQUENCE: 137

Ser Gln Xaa Pro Gln Ser Glu Thr Asp Tyr Ser Gln Leu Ser Gly Glu
1               5                   10                  15

Trp Asn Thr Ile Tyr Gly Ala Ala Ser Asn Ile Xaa Lys
                20                  25

<210> SEQ ID NO 138
<211> LENGTH: 211
<212> TYPE: PRT
<213> ORGANISM: Euroglyphus maynei

<400> SEQUENCE: 138

Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
                20                  25                  30

Gly Ser Cys Trp Ala Phe Ser Gly Val Ala Ser Thr Glu Ser Ala Tyr
            35                  40                  45

Leu Ala Tyr Arg Asn Met Ser Leu Asp Leu Ala Glu Gln Glu Leu Val
        50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
                100                 105                 110

Gly Leu Lys Asn Tyr Cys Gln Ile Ser Pro Pro Asp Ser Asn Lys Ile
            115                 120                 125

Arg Gln Ala Leu Thr Gln Thr His Thr Ala Val Ala Val Ile Ile Gly
        130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
                180                 185                 190

Trp Asp Thr Thr Trp Gly Asp Asn Gly Tyr Gly Tyr Phe Ala Ala Asn
            195                 200                 205

Ile Asn Leu
    210

<210> SEQ ID NO 139
<211> LENGTH: 211
<212> TYPE: PRT
<213> ORGANISM: Euroglyphus maynei

<400> SEQUENCE: 139

Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
                20                  25                  30
```

```
Gly Ser Cys Trp Ala Phe Ser Gly Val Ala Ser Thr Glu Ser Ala Tyr
            35                  40                  45

Leu Ala Tyr Arg Asn Met Ser Leu Asp Leu Ala Glu Gln Glu Leu Val
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
                100                 105                 110

Gly Leu Lys Asn Tyr Cys Gln Ile Ser Pro Pro Asp Ser Asn Lys Ile
                115                 120                 125

Arg Gln Ala Leu Thr Gln Thr His Thr Ala Val Ala Val Ile Ile Gly
            130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
            195                 200                 205

Ile Asn Leu
    210

<210> SEQ ID NO 140
<211> LENGTH: 211
<212> TYPE: PRT
<213> ORGANISM: Euroglyphus maynei

<400> SEQUENCE: 140

Glu Thr Asn Ala Cys Ser Ile Asn Gly Asn Ala Pro Ala Glu Ile Asp
1               5                   10                  15

Leu Arg Gln Met Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
            35                  40                  45

Leu Ala Tyr Arg Asn Gln Ser Leu Asp Leu Ala Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
                85                  90                  95

Tyr Val Ala Arg Glu Gln Ser Cys Arg Arg Pro Asn Ala Gln Arg Phe
                100                 105                 110

Gly Ile Ser Asn Tyr Cys Gln Ile Tyr Pro Pro Asn Ala Asn Lys Ile
                115                 120                 125

Arg Glu Ala Leu Ala Gln Thr His Ser Ala Ile Ala Val Ile Ile Gly
            130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
                165                 170                 175

Gly Tyr Ser Asn Ala Gln Gly Val Asp Tyr Trp Ile Val Arg Asn Ser
```

```
            180                 185                 190
Trp Asp Thr Asn Trp Gly Asp Asn Gly Tyr Gly Tyr Phe Ala Ala Asn
        195                 200                 205

Ile Asp Leu
    210

<210> SEQ ID NO 141
<211> LENGTH: 212
<212> TYPE: PRT
<213> ORGANISM: Euroglyphus maynei

<400> SEQUENCE: 141

Glu Thr Ser Ala Cys Arg Ile Asn Ser Val Asn Val Pro Ser Glu Leu
1               5                   10                  15

Asp Leu Arg Ser Leu Arg Thr Val Thr Pro Ile Arg Met Gln Gly Gly
            20                  25                  30

Cys Gly Ser Cys Trp Ala Phe Ser Gly Val Ala Ala Thr Glu Ser Ala
        35                  40                  45

Tyr Leu Ala Tyr Arg Asn Thr Ser Leu Asp Leu Ser Glu Gln Glu Leu
    50                  55                  60

Val Asp Cys Ala Ser Gln His Gly Cys His Gly Asp Thr Ile Pro Arg
65                  70                  75                  80

Gly Ile Glu Tyr Ile Gln Gln Asn Gly Val Val Glu Glu Arg Ser Tyr
                85                  90                  95

Pro Tyr Val Ala Arg Glu Gln Gln Cys Arg Arg Pro Asn Ser Gln His
            100                 105                 110

Tyr Gly Ile Ser Asn Tyr Cys Gln Ile Tyr Pro Pro Asp Val Lys Gln
        115                 120                 125

Ile Arg Glu Ala Leu Thr Gln Thr His Thr Ala Ile Ala Val Ile Ile
    130                 135                 140

Gly Ile Lys Asp Leu Arg Ala Phe Gln His Tyr Asp Gly Arg Thr Ile
145                 150                 155                 160

Ile Gln His Asp Asn Gly Tyr Gln Pro Asn Tyr His Ala Val Asn Ile
                165                 170                 175

Val Gly Tyr Gly Ser Thr Gln Gly Val Asp Tyr Trp Ile Val Arg Asn
            180                 185                 190

Ser Trp Asp Thr Thr Trp Gly Asp Ser Gly Tyr Gly Tyr Phe Gln Ala
        195                 200                 205

Gly Asn Asn Leu
    210

<210> SEQ ID NO 142
<211> LENGTH: 307
<212> TYPE: PRT
<213> ORGANISM: Poa pratensis

<400> SEQUENCE: 142

Met Ala Val Gln Lys Tyr Thr Val Ala Leu Phe Leu Val Ala Leu Val
1               5                   10                  15

Val Gly Pro Ala Ala Ser Tyr Ala Ala Asp Leu Ser Tyr Gly Ala Pro
            20                  25                  30

Ala Thr Pro Ala Ala Pro Ala Gly Tyr Thr Pro Ala Ala Pro Ala
        35                  40                  45

Gly Ala Ala Pro Lys Ala Thr Thr Asp Glu Gln Lys Met Ile Glu Lys
    50                  55                  60

Ile Asn Val Gly Phe Lys Ala Ala Val Ala Ala Ala Gly Gly Val Pro
```

```
                65                  70                  75                  80
Ala Ala Asn Lys Tyr Lys Thr Phe Val Ala Thr Phe Gly Ala Ala Ser
                85                  90                  95

Asn Lys Ala Phe Ala Glu Ala Leu Ser Thr Glu Pro Lys Gly Ala Ala
                100                 105                 110

Val Asp Ser Ser Lys Ala Ala Leu Thr Ser Lys Leu Asp Ala Ala Tyr
                115                 120                 125

Lys Leu Ala Tyr Lys Ser Ala Glu Gly Ala Thr Pro Glu Ala Lys Tyr
                130                 135                 140

Asp Asp Tyr Val Ala Thr Leu Ser Glu Ala Leu Arg Ile Ile Ala Gly
145                 150                 155                 160

Thr Leu Glu Val His Gly Val Lys Pro Ala Ala Glu Val Lys Ala
                165                 170                 175

Thr Pro Ala Gly Glu Leu Gln Val Ile Asp Lys Val Asp Ala Ala Phe
                180                 185                 190

Lys Val Ala Ala Thr Ala Ala Asn Ala Ala Pro Ala Asn Asp Lys Phe
                195                 200                 205

Thr Val Phe Glu Ala Ala Phe Asn Asp Ala Ile Lys Ala Ser Thr Gly
                210                 215                 220

Gly Ala Tyr Gln Ser Tyr Lys Phe Ile Pro Ala Leu Glu Ala Ala Val
225                 230                 235                 240

Lys Gln Ser Tyr Ala Ala Thr Val Ala Thr Ala Pro Val Lys Tyr
                245                 250                 255

Thr Val Phe Glu Thr Ala Leu Lys Lys Ala Ile Thr Ala Met Ser Gln
                260                 265                 270

Ala Gln Lys Ala Ala Lys Pro Ala Ala Ala Thr Gly Thr Ala Thr
                275                 280                 285

Ala Ala Val Gly Ala Ala Thr Gly Ala Ala Thr Ala Ala Gly Gly
                290                 295                 300

Tyr Lys Val
305

<210> SEQ ID NO 143
<211> LENGTH: 333
<212> TYPE: PRT
<213> ORGANISM: Poa pratensis

<400> SEQUENCE: 143

Met Ala Val His Gln Tyr Thr Val Ala Leu Phe Leu Ala Val Ala Leu
1               5                   10                  15

Val Ala Gly Pro Ala Ala Ser Tyr Ala Ala Asp Val Gly Tyr Gly Ala
                20                  25                  30

Pro Ala Thr Leu Ala Thr Pro Ala Thr Pro Ala Ala Pro Ala Ala Gly
                35                  40                  45

Tyr Thr Pro Ala Ala Pro Ala Gly Ala Ala Pro Lys Ala Thr Thr Asp
                50                  55                  60

Glu Gln Lys Leu Ile Glu Lys Ile Asn Ala Gly Phe Lys Ala Ala Val
65                  70                  75                  80

Ala Ala Ala Ala Gly Val Pro Ala Val Asp Lys Tyr Lys Thr Phe Val
                85                  90                  95

Ala Thr Phe Gly Thr Ala Ser Asn Lys Ala Phe Ala Glu Ala Leu Ser
                100                 105                 110

Thr Glu Pro Lys Gly Ala Ala Ala Ser Ser Asn Ala Val Leu Thr
                115                 120                 125
```

```
Ser Lys Leu Asp Ala Ala Tyr Lys Leu Ala Tyr Lys Ser Ala Glu Gly
    130                 135                 140

Ala Thr Pro Glu Ala Lys Tyr Asp Ala Tyr Val Ala Thr Leu Ser Glu
145                 150                 155                 160

Ala Leu Arg Ile Ile Ala Gly Thr Leu Glu Val His Ala Val Lys Pro
                165                 170                 175

Ala Gly Glu Glu Val Lys Ala Ile Pro Ala Gly Glu Leu Gln Val Ile
            180                 185                 190

Asp Lys Val Asp Ala Ala Phe Lys Val Ala Ala Thr Ala Ala Asn Ala
        195                 200                 205

Ala Pro Ala Asn Asp Lys Phe Thr Val Phe Glu Ala Ala Phe Asn Asp
210                 215                 220

Ala Ile Lys Ala Ser Thr Gly Gly Ala Tyr Gln Ser Tyr Lys Phe Ile
225                 230                 235                 240

Pro Ala Leu Glu Ala Ala Val Lys Gln Ser Tyr Ala Ala Thr Val Ala
                245                 250                 255

Thr Ala Pro Ala Val Lys Tyr Thr Val Phe Glu Thr Ala Leu Lys Lys
            260                 265                 270

Ala Ile Thr Ala Met Ser Gln Ala Gln Lys Ala Ala Lys Pro Ala Ala
        275                 280                 285

Ala Val Thr Ala Thr Ala Thr Gly Ala Val Gly Ala Ala Thr Gly Ala
290                 295                 300

Val Gly Ala Ala Thr Gly Ala Ala Thr Ala Ala Ala Gly Gly Tyr Lys
305                 310                 315                 320

Thr Gly Ala Ala Thr Pro Thr Ala Gly Gly Tyr Lys Val
                325                 330

<210> SEQ ID NO 144
<211> LENGTH: 373
<212> TYPE: PRT
<213> ORGANISM: Poa pratensis

<400> SEQUENCE: 144

Met Asp Lys Ala Asn Gly Ala Tyr Lys Thr Ala Leu Lys Ala Ala Ser
1               5                   10                  15

Ala Val Ala Pro Ala Glu Lys Phe Pro Val Phe Gln Ala Thr Phe Asp
                20                  25                  30

Lys Asn Leu Lys Glu Gly Leu Ser Gly Pro Asp Ala Val Gly Phe Ala
            35                  40                  45

Lys Lys Leu Asp Ala Phe Ile Gln Thr Ser Tyr Leu Ser Thr Lys Ala
        50                  55                  60

Ala Glu Pro Lys Glu Lys Phe Asp Leu Phe Val Leu Ser Leu Thr Glu
65                  70                  75                  80

Val Leu Arg Phe Met Ala Gly Ala Val Lys Ala Pro Ala Ser Lys
                85                  90                  95

Phe Pro Ala Lys Pro Ala Pro Lys Val Ala Ala Tyr Thr Pro Ala Ala
                100                 105                 110

Pro Ala Gly Ala Ala Pro Lys Ala Thr Thr Asp Glu Gln Lys Leu Ile
            115                 120                 125

Glu Lys Ile Asn Val Gly Phe Lys Ala Ala Val Ala Ala Ala Ala Gly
        130                 135                 140

Val Pro Ala Ala Ser Lys Tyr Lys Thr Phe Val Ala Thr Phe Gly Ala
145                 150                 155                 160

Ala Ser Asn Lys Ala Phe Ala Glu Ala Leu Ser Thr Glu Pro Lys Gly
                165                 170                 175
```

```
Ala Ala Val Ala Ser Ser Lys Ala Val Leu Thr Ser Lys Leu Asp Ala
            180                 185                 190

Ala Tyr Lys Leu Ala Tyr Lys Ser Ala Glu Gly Ala Thr Pro Glu Ala
            195                 200                 205

Lys Tyr Asp Ala Tyr Val Ala Thr Leu Ser Glu Ala Leu Arg Ile Ile
    210                 215                 220

Ala Gly Thr Leu Glu Val His Gly Val Lys Pro Ala Ala Glu Glu Val
225                 230                 235                 240

Lys Ala Ile Pro Ala Gly Glu Leu Gln Val Ile Asp Lys Val Asp Ala
                245                 250                 255

Ala Phe Lys Val Ala Ala Thr Ala Ala Asn Ala Ala Pro Ala Asn Asp
            260                 265                 270

Lys Phe Thr Val Phe Glu Ala Ala Phe Asn Asp Ala Ile Lys Ala Ser
            275                 280                 285

Thr Gly Gly Ala Tyr Gln Ser Tyr Lys Phe Ile Pro Ala Leu Glu Ala
            290                 295                 300

Ala Val Lys Gln Ser Tyr Ala Ala Thr Val Ala Thr Ala Pro Ala Val
305                 310                 315                 320

Lys Tyr Thr Val Phe Glu Thr Ala Leu Lys Lys Ala Ile Thr Ala Met
                325                 330                 335

Ser Gln Ala Gln Lys Ala Ala Lys Pro Ala Ala Ala Val Thr Gly Thr
            340                 345                 350

Ala Thr Ser Ala Val Gly Ala Ala Thr Gly Ala Ala Thr Ala Ala Ala
            355                 360                 365

Gly Gly Tyr Lys Val
    370

<210> SEQ ID NO 145
<211> LENGTH: 685
<212> TYPE: PRT
<213> ORGANISM: Periplaneta americana

<400> SEQUENCE: 145

Met Lys Thr Ala Leu Val Phe Ala Ala Val Ala Phe Val Ala Ala
1               5                   10                  15

Arg Phe Pro Asp His Lys Asp Tyr Lys Gln Leu Ala Asp Lys Gln Phe
            20                  25                  30

Leu Ala Lys Gln Arg Asp Val Leu Arg Leu Phe His Arg Val His Gln
            35                  40                  45

His Asn Ile Leu Asn Asp Gln Val Glu Val Gly Ile Pro Met Thr Ser
    50                  55                  60

Lys Gln Thr Ser Ala Thr Thr Val Pro Pro Ser Gly Glu Ala Val His
65                  70                  75                  80

Gly Val Leu Gln Glu Gly His Ala Arg Pro Arg Gly Glu Pro Phe Ser
            85                  90                  95

Val Asn Tyr Glu Lys His Arg Glu Gln Ala Ile Met Leu Tyr Asp Leu
            100                 105                 110

Leu Tyr Phe Ala Asn Asp Tyr Asp Thr Phe Tyr Lys Thr Ala Cys Trp
            115                 120                 125

Ala Arg Asp Arg Val Asn Glu Gly Met Phe Met Tyr Ser Phe Ser Ile
            130                 135                 140

Ala Val Phe His Arg Asp Asp Met Gln Gly Val Met Leu Pro Pro Pro
145                 150                 155                 160

Tyr Glu Val Tyr Pro Tyr Leu Phe Val Asp His Asp Val Ile His Met
```

```
                165                 170                 175
Ala Gln Lys Tyr Trp Met Lys Asn Ala Gly Ser Gly Glu His His Ser
            180                 185                 190

His Val Ile Pro Val Asn Phe Thr Leu Arg Thr Gln Asp His Leu Leu
        195                 200                 205

Ala Tyr Phe Thr Ser Asp Val Asn Leu Asn Ala Phe Asn Thr Tyr Tyr
210                 215                 220

Arg Tyr Tyr Tyr Pro Ser Trp Tyr Asn Thr Thr Leu Tyr Gly His Asn
225                 230                 235                 240

Ile Asp Arg Arg Gly Glu Gln Phe Tyr Tyr Thr Tyr Lys Gln Ile Tyr
                245                 250                 255

Ala Arg Tyr Phe Leu Glu Arg Leu Ser Asn Asp Leu Pro Asp Val Tyr
            260                 265                 270

Pro Phe Tyr Tyr Ser Lys Pro Val Lys Ser Ala Tyr Asn Pro Asn Leu
        275                 280                 285

Arg Tyr His Asn Gly Glu Glu Met Pro Val Arg Pro Ser Asn Met Tyr
    290                 295                 300

Val Thr Asn Phe Asp Leu Tyr Tyr Ile Ala Asp Ile Lys Asn Tyr Glu
305                 310                 315                 320

Lys Arg Val Glu Asp Ala Ile Asp Phe Gly Tyr Ala Phe Asp Glu His
                325                 330                 335

Met Lys Pro His Ser Leu Tyr His Asp Val His Gly Met Glu Tyr Leu
            340                 345                 350

Ala Asp Met Ile Glu Gly Asn Met Asp Ser Pro Asn Phe Tyr Phe Tyr
        355                 360                 365

Gly Ser Ile Tyr His Met Tyr His Ser Met Ile Gly His Ile Val Asp
    370                 375                 380

Pro Tyr His Lys Met Gly Leu Ala Pro Ser Leu Glu His Pro Glu Thr
385                 390                 395                 400

Val Leu Arg Asp Pro Val Phe Tyr Gln Leu Trp Lys Arg Val Asp His
                405                 410                 415

Leu Phe Gln Lys Tyr Lys Asn Arg Leu Pro Arg Tyr Thr His Asp Glu
            420                 425                 430

Leu Ala Phe Glu Gly Val Lys Val Glu Asn Val Asp Val Gly Lys Leu
        435                 440                 445

Tyr Thr Tyr Phe Glu Gln Tyr Asp Met Ser Leu Asp Met Ala Val Tyr
    450                 455                 460

Val Asn Asn Val Asp Gln Ile Ser Asn Val Asp Val Gln Leu Ala Val
465                 470                 475                 480

Arg Leu Asn His Lys Pro Phe Thr Tyr Asn Ile Glu Val Ser Ser Asp
                485                 490                 495

Lys Ala Gln Asp Val Tyr Val Ala Val Phe Leu Gly Pro Lys Tyr Asp
            500                 505                 510

Tyr Leu Gly Arg Glu Tyr Asp Leu Asn Asp Arg His Tyr Phe Val
        515                 520                 525

Glu Met Asp Arg Phe Pro Tyr His Val Gly Ala Gly Lys Thr Val Ile
    530                 535                 540

Glu Arg Asn Ser His Asp Ser Asn Ile Ile Ala Pro Glu Arg Asp Ser
545                 550                 555                 560

Tyr Arg Thr Phe Tyr Lys Val Gln Glu Ala Tyr Glu Gly Lys Ser
                565                 570                 575

Gln Tyr Tyr Val Asp Lys Gly His Asn Tyr Cys Gly Tyr Pro Glu Asn
            580                 585                 590
```

```
Leu Leu Ile Pro Lys Gly Lys Gly Gln Ala Tyr Thr Phe Tyr
        595                 600                 605

Val Ile Val Thr Pro Tyr Val Lys Gln Asp Glu His Asp Phe Glu Pro
610                 615                 620

Tyr Asn Tyr Lys Ala Phe Ser Tyr Cys Gly Val Gly Ser Glu Arg Lys
625                 630                 635                 640

Tyr Pro Asp Asn Lys Pro Leu Gly Tyr Pro Phe Asp Arg Lys Ile Tyr
                645                 650                 655

Ser Asn Asp Phe Tyr Thr Pro Asn Met Tyr Phe Lys Asp Val Ile Ile
                660                 665                 670

Phe His Lys Lys Tyr Asp Glu Val Gly Val Gln Gly His
                675                 680                 685

<210> SEQ ID NO 146
<211> LENGTH: 446
<212> TYPE: PRT
<213> ORGANISM: Periplaneta americana

<400> SEQUENCE: 146

Ile Asn Glu Ile His Ser Ile Ile Gly Leu Pro Pro Phe Val Pro Pro
1               5                   10                  15

Ser Arg Arg His Ala Arg Arg Gly Val Gly Ile Asn Gly Leu Ile Asp
                20                  25                  30

Asp Val Ile Ala Ile Leu Pro Val Asp Glu Leu Lys Ala Leu Phe Gln
            35                  40                  45

Glu Lys Leu Glu Thr Ser Pro Asp Phe Lys Ala Leu Tyr Asp Ala Ile
50                  55                  60

Arg Ser Pro Glu Phe Gln Ser Ile Ile Ser Thr Leu Asn Ala Met Gln
65                  70                  75                  80

Arg Ser Glu His His Gln Asn Leu Arg Asp Lys Gly Val Asp Val Asp
                85                  90                  95

His Phe Ile Gln Leu Ile Arg Ala Leu Phe Gly Leu Ser Arg Ala Ala
            100                 105                 110

Arg Asn Leu Gln Asp Asp Leu Asn Asp Phe Leu His Ser Leu Glu Pro
        115                 120                 125

Ile Ser Pro Arg His Arg His Gly Leu Pro Arg Gln Arg Arg Arg Ser
    130                 135                 140

Ala Arg Val Ser Ala Tyr Leu His Ala Asp Asp Phe His Lys Ile Ile
145                 150                 155                 160

Thr Thr Ile Glu Ala Leu Pro Glu Phe Ala Asn Phe Tyr Asn Phe Leu
                165                 170                 175

Lys Glu His Gly Leu Asp Val Val Asp Tyr Ile Asn Glu Ile His Ser
            180                 185                 190

Ile Ile Gly Leu Pro Pro Phe Val Pro Pro Ser Arg Arg His Ala Arg
        195                 200                 205

Arg Gly Val Gly Ile Asn Gly Leu Ile Asp Asp Val Ile Ala Ile Leu
    210                 215                 220

Pro Val Asp Glu Leu Lys Ala Leu Phe Gln Glu Lys Leu Glu Thr Ser
225                 230                 235                 240

Pro Asp Phe Lys Ala Leu Tyr Asp Ala Ile Arg Ser Pro Glu Phe Gln
                245                 250                 255

Ser Ile Ile Ser Thr Leu Asn Ala Met Pro Glu Tyr Gln Glu Leu Leu
            260                 265                 270

Gln Asn Leu Arg Asp Lys Gly Val Asp Val Asp His Phe Ile Arg Val
```

```
                    275                 280                 285
Asp Gln Gly Thr Leu Arg Thr Leu Ser Ser Gly Gln Arg Asn Leu Gln
290                 295                 300

Asp Asp Leu Asn Asp Phe Leu Ala Leu Ile Pro Thr Asp Gln Ile Leu
305                 310                 315                 320

Ala Ile Ala Met Asp Tyr Leu Ala Asn Asp Ala Glu Val Gln Glu Leu
                325                 330                 335

Val Ala Tyr Leu Gln Ser Asp Asp Phe His Lys Ile Ile Thr Thr Ile
            340                 345                 350

Glu Ala Leu Pro Glu Phe Ala Asn Phe Tyr Asn Phe Leu Lys Glu His
                355                 360                 365

Gly Leu Asp Val Val Asp Tyr Ile Asn Glu Ile His Ser Ile Ile Gly
            370                 375                 380

Leu Pro Pro Phe Val Pro Pro Ser Gln Arg His Ala Arg Arg Gly Val
385                 390                 395                 400

Gly Ile Asn Gly Leu Ile Asp Asp Val Ile Ala Ile Leu Pro Val Asp
                405                 410                 415

Glu Leu Lys Ala Leu Phe Gln Glu Lys Leu Glu Thr Ser Pro Asp Phe
            420                 425                 430

Lys Ala Leu Tyr Asp Ala Ile Asp Leu Arg Ser Ser Arg Ala
                435                 440                 445

<210> SEQ ID NO 147
<211> LENGTH: 352
<212> TYPE: PRT
<213> ORGANISM: Blattella germanica

<400> SEQUENCE: 147

Met Ile Gly Leu Lys Leu Val Thr Val Leu Phe Ala Val Ala Thr Ile
1               5                   10                  15

Thr His Ala Ala Glu Leu Gln Arg Val Pro Leu Tyr Lys Leu Val His
                20                  25                  30

Val Phe Ile Asn Thr Gln Tyr Ala Gly Ile Thr Lys Ile Gly Asn Gln
            35                  40                  45

Asn Phe Leu Thr Val Phe Asp Ser Thr Ser Cys Asn Val Val Val Ala
        50                  55                  60

Ser Gln Glu Cys Val Gly Gly Ala Cys Val Cys Pro Asn Leu Gln Lys
65                  70                  75                  80

Tyr Glu Lys Leu Lys Pro Lys Tyr Ile Ser Asp Gly Asn Val Gln Val
                85                  90                  95

Lys Phe Phe Asp Thr Gly Ser Ala Val Gly Arg Gly Ile Glu Asp Ser
                100                 105                 110

Leu Thr Ile Ser Asn Leu Thr Thr Ser Gln Gln Asp Ile Val Leu Ala
            115                 120                 125

Asp Glu Leu Ser Gln Glu Val Cys Ile Leu Ser Ala Asp Val Val Val
130                 135                 140

Gly Ile Ala Ala Pro Gly Cys Pro Asn Ala Leu Lys Gly Lys Thr Val
145                 150                 155                 160

Leu Glu Asn Phe Val Glu Glu Asn Leu Ile Ala Pro Val Phe Ser Ile
                165                 170                 175

His His Ala Arg Phe Gln Asp Gly Glu His Phe Gly Glu Ile Ile Phe
            180                 185                 190

Gly Gly Ser Asp Trp Lys Tyr Val Asp Gly Glu Phe Thr Tyr Val Pro
            195                 200                 205
```

```
Leu Val Gly Asp Asp Ser Trp Lys Phe Arg Leu Asp Gly Val Lys Ile
            210                 215                 220

Gly Asp Thr Thr Val Ala Pro Ala Gly Thr Gln Ala Ile Ile Asp Thr
225                 230                 235                 240

Ser Lys Ala Ile Ile Val Gly Pro Lys Ala Tyr Val Asn Pro Ile Asn
                245                 250                 255

Glu Ala Ile Gly Cys Val Val Glu Lys Thr Thr Thr Arg Arg Ile Cys
                260                 265                 270

Lys Leu Asp Cys Ser Lys Ile Pro Ser Leu Pro Asp Val Thr Phe Val
                275                 280                 285

Ile Asn Gly Arg Asn Phe Asn Ile Ser Ser Gln Tyr Tyr Ile Gln Gln
290                 295                 300

Asn Gly Asn Leu Cys Tyr Ser Gly Phe Gln Pro Cys Gly His Ser Asp
305                 310                 315                 320

His Phe Phe Ile Gly Asp Phe Val Asp His Tyr Tyr Ser Glu Phe
                325                 330                 335

Asn Trp Glu Asn Lys Thr Met Gly Phe Gly Arg Ser Val Glu Ser Val
                340                 345                 350
```

<210> SEQ ID NO 148
<211> LENGTH: 182
<212> TYPE: PRT
<213> ORGANISM: Blattella germanica

<400> SEQUENCE: 148

```
Ala Val Leu Ala Leu Cys Ala Thr Asp Thr Leu Ala Asn Glu Asp Cys
1               5                   10                  15

Phe Arg His Glu Ser Leu Val Pro Asn Leu Asp Tyr Glu Arg Phe Arg
                20                  25                  30

Gly Ser Trp Ile Ile Ala Ala Gly Thr Ser Glu Ala Leu Thr Gln Tyr
            35                  40                  45

Lys Cys Trp Ile Asp Arg Phe Ser Tyr Asp Asp Ala Leu Val Ser Lys
50                  55                  60

Tyr Thr Asp Ser Gln Gly Lys Asn Arg Thr Thr Ile Arg Gly Arg Thr
65                  70                  75                  80

Lys Phe Glu Gly Asn Lys Phe Thr Ile Asp Tyr Asn Asp Lys Gly Lys
                85                  90                  95

Ala Phe Ser Ala Pro Tyr Ser Val Leu Ala Thr Asp Tyr Glu Asn Tyr
            100                 105                 110

Ala Ile Val Glu Gly Cys Pro Ala Ala Ala Asn Gly His Val Ile Tyr
        115                 120                 125

Val Gln Ile Arg Phe Ser Val Arg Arg Phe His Pro Lys Leu Gly Asp
130                 135                 140

Lys Glu Met Ile Gln His Tyr Thr Leu Asp Gln Val Asn Gln His Lys
145                 150                 155                 160

Lys Ala Ile Glu Glu Asp Leu Lys His Phe Asn Leu Lys Tyr Glu Asp
                165                 170                 175

Leu His Ser Thr Cys His
            180
```

<210> SEQ ID NO 149
<211> LENGTH: 200
<212> TYPE: PRT
<213> ORGANISM: Blattella germanica

<400> SEQUENCE: 149

```
Tyr Lys Leu Thr Tyr Cys Pro Val Lys Ala Leu Gly Glu Pro Ile Arg
1               5                   10                  15

Phe Leu Leu Ser Tyr Gly Glu Lys Asp Phe Glu Asp Tyr Arg Phe Gln
                20                  25                  30

Glu Gly Asp Trp Pro Asn Leu Lys Pro Ser Met Pro Phe Gly Lys Thr
            35                  40                  45

Pro Val Leu Glu Ile Asp Gly Lys Gln Thr His Gln Ser Val Ala Ile
        50                  55                  60

Ser Arg Tyr Leu Gly Lys Gln Phe Gly Leu Ser Gly Lys Asp Asp Trp
65                  70                  75                  80

Glu Asn Leu Glu Ile Asp Met Ile Val Asp Thr Ile Ser Asp Phe Arg
                85                  90                  95

Ala Ala Ile Ala Asn Tyr His Tyr Asp Ala Asp Glu Asn Ser Lys Gln
            100                 105                 110

Lys Lys Trp Asp Pro Leu Lys Lys Glu Thr Ile Pro Tyr Tyr Thr Lys
            115                 120                 125

Lys Phe Asp Glu Val Val Lys Ala Asn Gly Gly Tyr Leu Ala Ala Gly
        130                 135                 140

Lys Leu Thr Trp Ala Asp Phe Tyr Phe Val Ala Ile Leu Asp Tyr Leu
145                 150                 155                 160

Asn His Met Ala Lys Glu Asp Leu Val Ala Asn Gln Pro Asn Leu Lys
                165                 170                 175

Ala Leu Arg Glu Lys Val Leu Gly Leu Pro Ala Ile Lys Ala Trp Val
            180                 185                 190

Ala Lys Arg Pro Pro Thr Asp Leu
            195                 200

<210> SEQ ID NO 150
<211> LENGTH: 18
<212> TYPE: PRT
<213> ORGANISM: Artificial
<220> FEATURE:
<223> OTHER INFORMATION: synthetic peptide

<400> SEQUENCE: 150

Lys Lys Gly Glu Ala Ala Ile Lys Leu Thr Ser Ser Ala Gly Val Leu
1               5                   10                  15

Ser Lys
```